United States Patent [19]

Loots et al.

[11] Patent Number: 4,849,414

[45] Date of Patent: Jul. 18, 1989

[54] SUBSTITUTED AMINOALKANOYLAMINOALKYL PHOSPHONATE ANGIOTENSIN CONVERTING ENZYME INHIBITORS

[75] Inventors: Melanie J. Loots, Pennington; Donald S. Karanewsky, East Windsor, both of N.J.

[73] Assignee: E. R. Squibb & Sons, Inc., Princeton, N.J.

[21] Appl. No.: 52,100

[22] Filed: May 20, 1987

Related U.S. Application Data

[63] Continuation-in-part of Ser. No. 873,035, Jun. 11, 1986, abandoned.

[51] Int. Cl.$^4$ .................. A61K 31/40; A61K 31/535; C07D 207/09; C07D 295/00
[52] U.S. Cl. ........................................ 514/63; 514/85; 514/89; 514/90; 514/91; 514/94; 548/413; 548/406; 544/57; 544/337
[58] Field of Search ................. 548/413, 406; 514/63, 514/91, 85, 89, 90, 94, 98; 544/57, 337

[56] References Cited

U.S. PATENT DOCUMENTS

| | | |
|---|---|---|
| 4,452,790 | 6/1984 | Karanewsky et al. ............. 424/200 |
| 4,555,506 | 11/1985 | Karanewsky et al. ............. 514/91 |
| 4,616,005 | 10/1986 | Karanewsky et al. ............. 514/80 |
| 4,634,689 | 1/1987 | Witkowski et al. ............. 540/542 |
| 4,670,422 | 6/1987 | Karanewsky et al. ............. 514/63 |
| 4,716,155 | 12/1987 | Karanewsky et al. ............. 514/89 |

OTHER PUBLICATIONS

Almquist et al., "Synthesis and Biological Activity..." J. Med. Chem., vol. 28, pp. 1062–1066 (1985).
Almquist et al., "Synthesis and Biological Activity..." J. Med. Chem., vol. 28, pp. 1067–1071 (1985).

Primary Examiner—Mary C. Lee
Assistant Examiner—E. Brendan Magrab
Attorney, Agent, or Firm—Stephen B. Davis

[57] ABSTRACT

Compounds of the formula

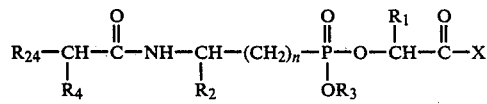

wherein X is various amino or imino acids and esters are disclosed. These compounds are useful as anti-hypertensive agents due to their angiotensin converting enzyme inhibition activity and depending upon the definition of X may also be useful as analgesics due to their enkephalinase inhibition activity.

27 Claims, No Drawings

SUBSTITUTED AMINOALKANOYLAMINOALKYL PHOSPHONATE ANGIOTENSIN CONVERTING ENZYME INHIBITORS

RELATED APPLICATION

This application is a continuation-in-part of U.S. Ser. No. 873,035 filed on June 11, 1986, now abandoned.

BACKGROUND OF THE INVENTION

Karanewsky et al. in U.S. Pat. No. 4,452,790 disclose angiotensin converting enzyme inhibitors of the formula

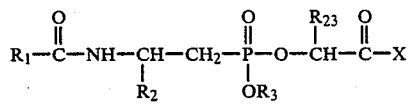

wherein $R_1$ is alkyl, substituted alkylene, or

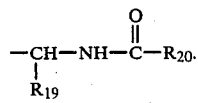

Karanewsky et al. in U.S. Pat. No. 4,555,506 disclose angiotensin converting enzyme inhibitors of formula

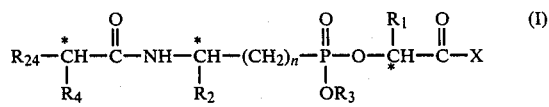

wherein $R_1$ is hydrogen, alkyl, substituted alkyl, aryl, aralkyl, or heteroalkylene.

SUMMARY OF THE INVENTION

This invention is directed to new substituted aminoalkanoylaminoalkyl phosphonate substituted amino or imino acids of formula I and salts thereof

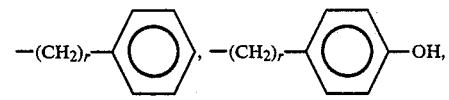  (I)

$R_1$ and $R_4$ are independently selected from hydrogen, lower alkyl, —(CH$_2$)$_r$—Cl, —(CH$_2$)$_r$—Br, —(CH$_2$)$_r$—F, CF$_3$,

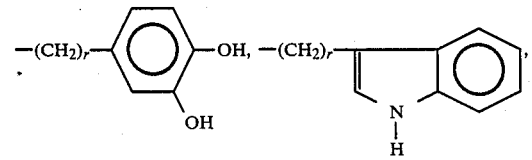

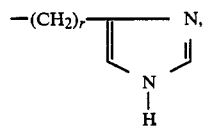

—(CH$_2$)$_r$-cycloalkyl, —(CH$_2$)$_r$—NH$_2$, —(CH$_2$)$_r$—SH, —(CH$_2$)$_r$—S-lower alkyl,

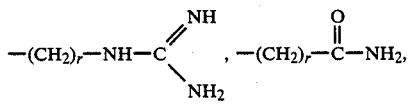

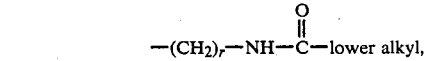

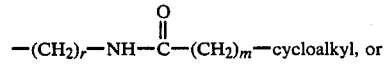

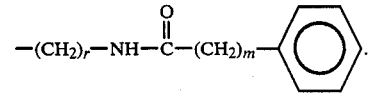

n is zero or one.
$R_2$ is lower alkyl,

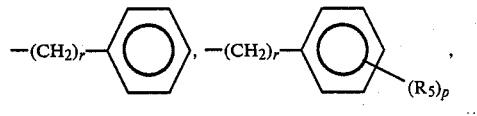

—(CH$_2$)$_r$-cycloalkyl, or —(CH$_2$)$_r$—NH$_2$.
$R_3$ is hydrogen, lower alkyl, alkali metal salt ion, alkaline earth metal salt ion, or

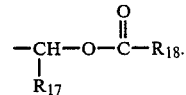

$R_{24}$ is NH$_2$,

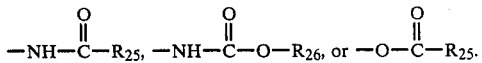

$R_{25}$ is hydrogen, lower alkyl,

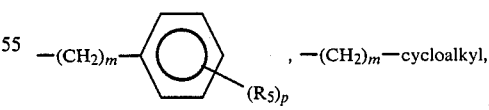

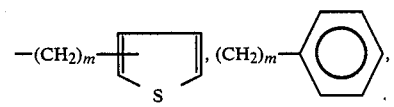

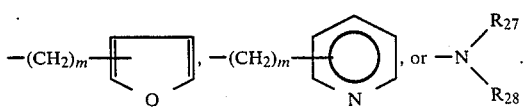

$R_{26}$ is lower alkyl, $-(CH_2)_q$-cycloalkyl,

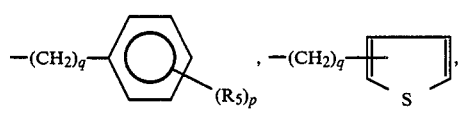

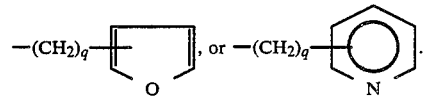

$R_{27}$ is hydrogen, lower alkyl, $-(CH_2)_m$-cycloalkyl

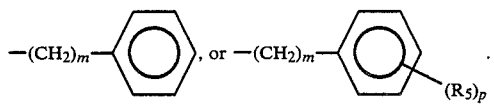

$R_{28}$ is lower alkyl, $-(CH_2)_m$-cycloalkyl,

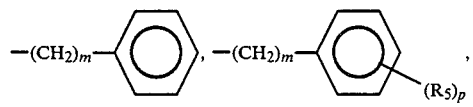

$R_{27}$ and $R_{28}$ taken together with the N atom to which they are attached complete a heterocyclic ring of the formula

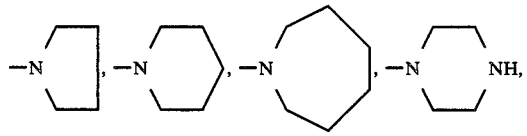

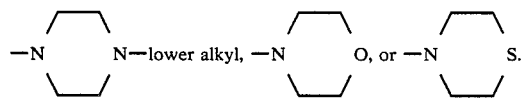

m is zero or an integer from 1 to 4.
r is an integer from 1 to 7.
q is an integer from 1 to 4.
x is an amino or imino acid or ester of the formula

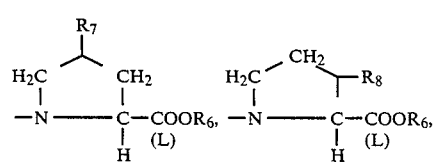

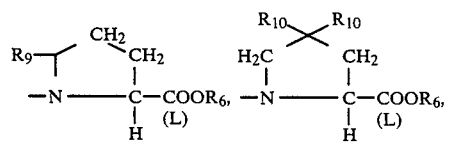

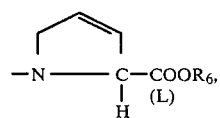

-continued

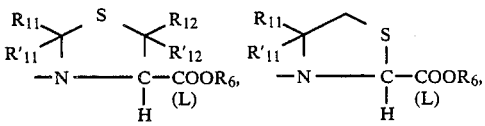

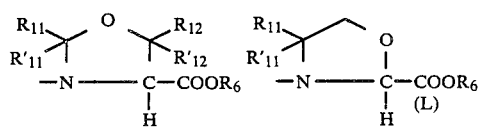

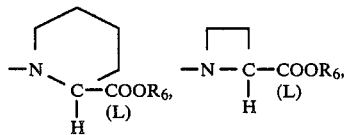

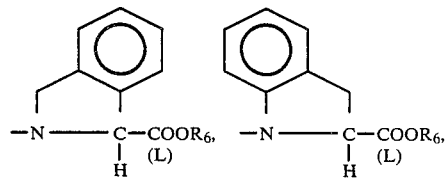

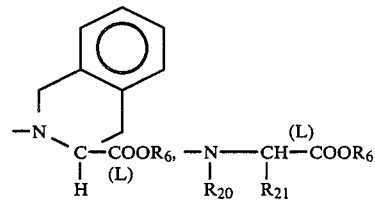

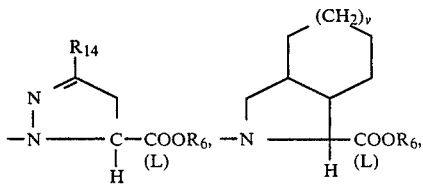

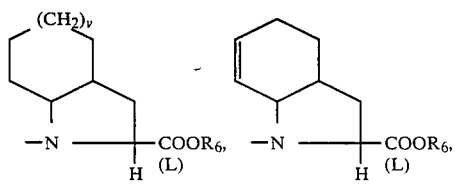

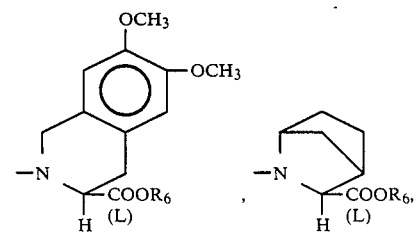

-continued

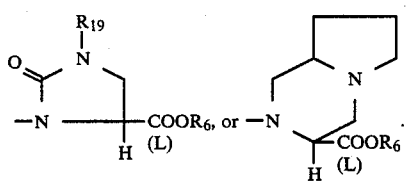

$R_7$ is hydrogen, lower alkyl, halogen, hydroxy,

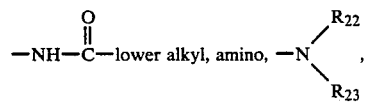

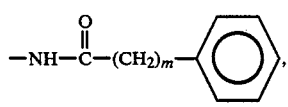

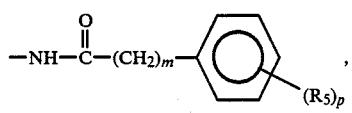

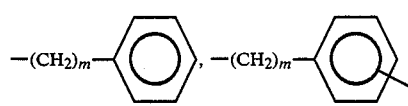

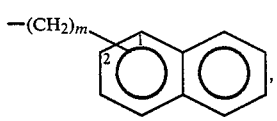

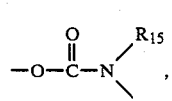

a 1- or 2-naphthyl of the formula

a substituted 1- or 2-naphthyl of the formula

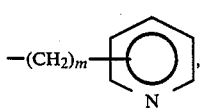

—(CH$_2$)$_m$-cycloalkyl,

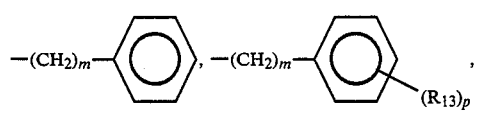

—O-lower alkyl,

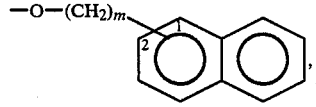

a 1- or 2- naphthyloxy of the formula

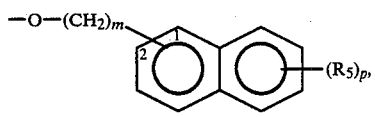

a substituted 1- or 2-naphthyloxy of the formula

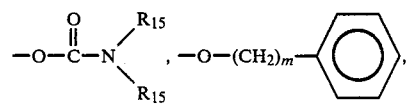

—S-lower alkyl,

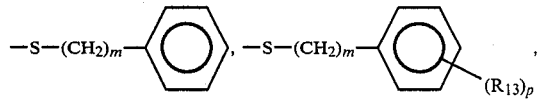

a 1- or 2-naphthylthio of the formula

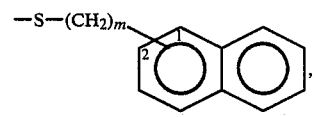

or a substituted 1- or 2-naphthylthio of the formula

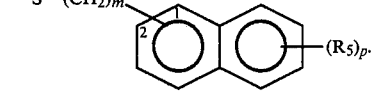

$R_8$ is lower alkyl, halogen

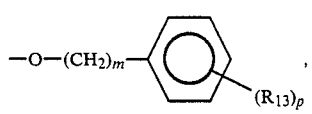

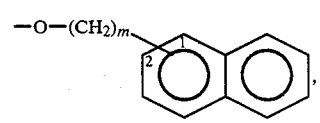

—O-lower alkyl, a 1- or 2-naphthyloxy of the formula a substituted 1- or 2-naphthyloxy of the formula

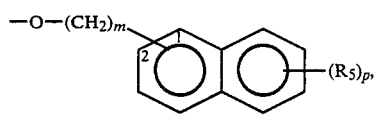

—S-lower alkyl,

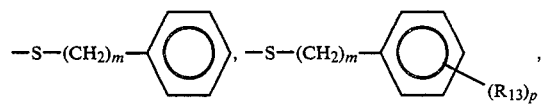

a 1- or 2-naphthylthio of the formula

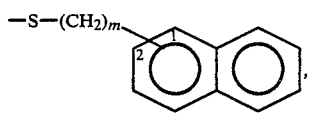

or a substituted 1- or 2-naphthylthio of the formula

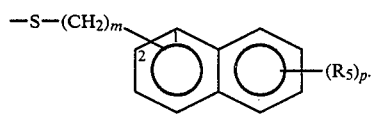

$R_9$ is lower alkyl, keto,

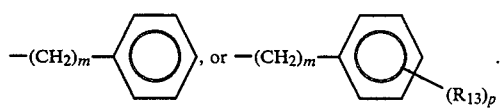

$R_{10}$ is halogen or Y—$R_{16}$.

$R_{11}$, $R'_{11}$, $R_{12}$ and $R'_{12}$ are independently selected from hydrogen and lower alkyl or $R'_{11}$, $R_{12}$ and $R'_{12}$ are hydrogen and $R_{11}$ is

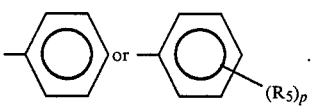

$R_{13}$ is lower alkyl of 1 to 4 carbons, lower alkoxy of 1 to 4 carbons, lower alkylthio of 1 to 4 carbons, chloro, bromo, fluoro, trifluoromethyl, hydroxy, phenyl, phenoxy, phenylthio, or phenylmethyl.

$R_5$ is lower alkyl of 1 to 4 carbons, lower alkoxy of 1 to 4 carbons, lower alkylthio of 1 to 4 carbons, chloro, bromo, fluoro, trifluoromethyl or hydroxy.

p is one, two or three provided that p is more than one only if $R_{13}$ or $R_5$ is methyl, methoxy, chloro, bromo, or fluoro.

$R_{14}$ is hydrogen, lower alkyl,

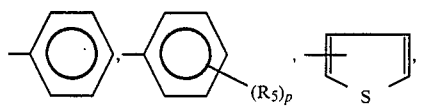

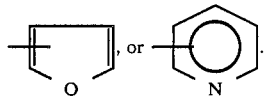

$R_{15}$ is hydrogen or lower alkyl of 1 to 4 carbons.
Y is oxygen or sulfur.
$R_{16}$ is lower alkyl of 1 to 4 carbons,

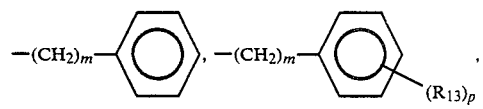

or the $R_{16}$ groups join to complete an unsubstituted 5- or 6-membered ring or said ring in which one or more of the carbons has a lower alkyl of 1 to 4 carbons or a di(lower alkyl of 1 to 4 carbons) substituent.

$R_{17}$ is hydrogen, lower alkyl, cycloalkyl, or phenyl.

$R_{18}$ is hydrogen, lower alkyl, lower alkoxy, or phenyl.

n is zero, one, or two.

$R_{19}$ is lower alkyl or

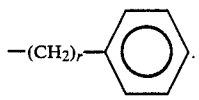

$R_{20}$ is hydrogen, lower alkyl,

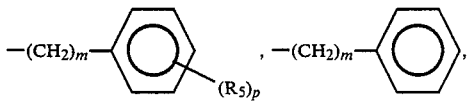

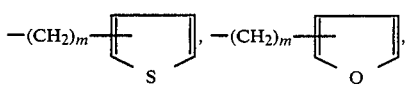

or —$(CH_2)_m$-cycloalkyl.

$R_{21}$ is hydrogen, lower alkyl,

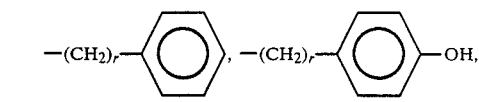

—$(CH_2)_r$—OH,

-continued $$-(CH_2)_r-\underset{\underset{H}{N}}{\overset{N}{\diagup\!\!\!\diagdown}}$$

$-(CH_2)_r-NH_2$, $-(CH_2)_r-SH$, $-(CH_2)_r-S$-lower alkyl, $$-(CH_2)_r-NH-\underset{NH_2}{\overset{NH}{C}}, \text{ or } -(CH_2)_r-\overset{O}{\underset{\|}{C}}-NH_2.$$

$R_{22}$ is lower alkyl, benzyl, or phenethyl.
$R_{23}$ is hydrogen, lower alkyl, benzyl, or phenethyl.
$R_6$ is hydrogen, lower alkyl, benzyl, benzhydryl, alkali metal salt ion, alkaline earth metal salt ion, $$-\underset{R_{17}}{\overset{}{CH}}-O-\overset{O}{\underset{\|}{C}}-R_{18},$$

or $-(CH_2)_2Si(CH_3)_3$.

DETAILED DESCRIPTION OF THE INVENTION

This invention in its broadest aspects relates to the amino and imino acid and ester compounds of formula I and to compositions and the method of using such compounds as pharmaceutical agents.

The term lower alkyl used in defining various symbols refers to straight or branched chain radicals having up to seven carbons. The preferred lower alkyl groups are up to four carbons with methyl and ethyl most preferred. Similarly the terms lower alkoxy and lower alkylthio refer to such lower alkyl groups attached to an oxygen or sulfur.

The term cycloalkyl refers to saturated hydrocarbon rings of 3 to 7 carbon atoms with cyclobutyl, cyclopentyl, and cyclohexyl being most preferred.

The term halogen refers to chloro, bromo and fluoro.

The symbols $-(CH_2)_q-\!\!\!\diagup\!\!\!\diagdown\!\!\!_S$, $-(CH_2)_q-\!\!\!\diagup\!\!\!\diagdown\!\!\!_O$, and $-(CH_2)_q-\!\!\!\diagup\!\!\!\diagdown\!\!\!_N$ represent that the alkylene bridge is attached to an available carbon atom.

The compounds of formula I can be prepared as follows. When $R_{24}$ is $$-NH-\overset{O}{\underset{\|}{C}}-R_{25},$$

the phosphinyl compound of the formula $$\underset{R_2}{\overset{O}{\underset{\|}{H_2N-CH-(CH_2)_n-\overset{}{P}-O-\underset{OR_3}{\overset{R_1}{CH}}-\overset{O}{\underset{\|}{C}}-X}}} \quad (II)$$

wherein $R_3$ is an ester group such as methyl and $R_6$ in the definition of X is an ester group such as methyl, ethyl, etc., is coupled with the acyl α-amino acid of the formula $$R_{25}-\overset{O}{\underset{\|}{C}}-NH-\underset{R_4}{\overset{}{CH}}-\overset{O}{\underset{\|}{C}}-OH \quad (III)$$

in the presence of triethylamine. This reaction is performed in the presence of a coupling agent such as dicyclohexylcarbodiimide or carbonyldiimidazole or by converting the acid of formula III to an activated form such as a mixed anhydride, for example, by employing pivaloyl chloride, an activated ester such as p-nitrophenol, or an acid chloride. Removal of the $R_3$ and $R_6$ ester groups by conventional means yields the desired diacid products of formula I.

The phosphinyl compound of formula II wherein n is zero can be prepared by coupling a phosphonous acid of the formula $$\text{Prot-NH}-\underset{R_2}{\overset{}{CH}}-\overset{O}{\underset{H}{\overset{\|}{P}}}-OH \quad (IV)$$

to the hydroxyalkanoyl amino or imino acid ester of the formula $$HO-\underset{}{\overset{R_1}{CH}}-\overset{O}{\underset{\|}{C}}-X \quad (V)$$

wherein $R_6$ in the definition of X is an easily removable ester protecting group such as benzyl and Prot is an amino protecting group such as benzyloxycarbonyl. This reaction is preferably carried out in the presence of a coupling agent such as dicyclohexylcarbodiimide and dimethylaminopyridine. The resulting phosphonous monoester is oxidized with sodium metaperiodate to give the phosphinyl intermediate of the formula $$\text{Prot-NH}-\underset{R_2}{\overset{}{CH}}-\overset{O}{\underset{OH}{\overset{\|}{P}}}-O-\underset{}{\overset{R_1}{CH}}-\overset{O}{\underset{\|}{C}}-X. \quad (VI)$$

The intermediate for formula VI can then be treated to remove the $R_6$ ester group, i.e., by the use of lithium hydroxide when $R_6$ is methyl or benzyl. This diacid can then be converted to the dimethyl ester, i.e., $R_3$ and $R_6$ are both methyl, by treatment with diazomethane and the Prot group removed, for example, by hydrogenation when Prot is benzyloxycarbonyl to give the material of formula II.

The phosphinyl compound of formula II wherein n is one can be prepared by coupling an acid chloride ester of the formula

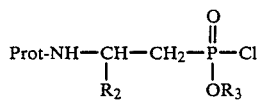 (VII)

to the hydroxyalkanoyl amino or imino acid ester of formula V wherein $R_6$ in the definition of X is an ester group such as ethyl and Prot is an amino protecting group such as benzyloxycarbonyl. Removal of the Prot group such as by hydrogenation gives the material of formula II.

The acid chloride of formula VII can be prepared according to the procedure described by Karanewsky et al. in U.S. Pat. No. 4,555,506. For example, an amine of the formula

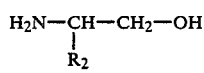 (VIII)

is reacted with p-toluenesulfonyl chloride in the presence of triethylamine to give

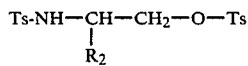 (IX)

wherein Ts is tolylsulfonyl, i.e.,

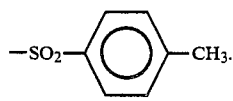

The protected amine of formula IX is then reacted with diethyl phosphate sodium salt, i.e.,

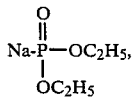

followed by treatment with hydrogen bromide (48%) to give the phosphonic acid of the formula

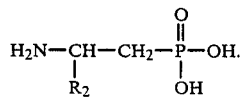 (X)

The phosphonic acid of formula X is reacted with benzyloxycarbonyl chloride in the presence of aqueous sodium hydroxide to give

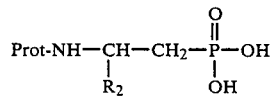 (XI)

wherein Prot is benzyloxycarbonyl. Treatment with the alcohol of the formula $R_3$—OH (XII)

in the presence of dicyclohexylcarbodiimide and dimethylaminopyridine or the halide of the formula $R_3$—halo (XIII)

wherein halo is Br or Cl gives the ester of the formula

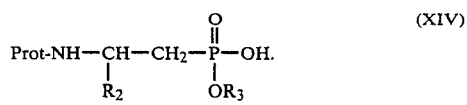 (XIV)

Treatment of the ester of formula XIV with phosphorus pentachloride or thionyl chloride gives the acid chloride of formula VII.

The compounds of formula I wherein $R_{24}$ is

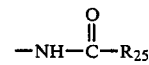

can also be prepared by coupling a phosphonic acid of the formula

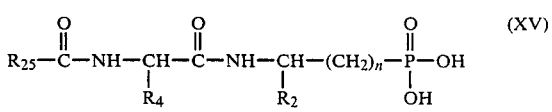 (XV)

to the hydroxyalkanoyl amino or imino acid ester of formula V. Preferably, this reaction is performed in the presence of a coupling agent such as dicyclohexylcarbodiimide or carbonyldiimidazole or by converting the acid of formula XV to an activated form.

The phosphonic acid of formula XV can be prepared by coupling the phosphonic acid dimethyl ester of the formula

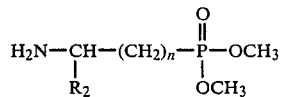 (XVI)

with the acyl α-amino acid of formula III in the presence of triethylamine. The reaction is carried out in the presence of a coupling agent or by converting the acid of formula III to an activated form as described previously. The resulting dimethyl ester is converted to the phosphonic acid of formula XV by treatment with trimethylsilyl bromide in dichloromethane.

The phosphonic acid dimethyl ester of formula XVI when n is one can be prepared by treating the acid of formula XI with diazomethane followed by hydrogenation to remove the benzyloxycarbonyl protecting group.

The phosphonic acid dimethyl ester of formula XVI when n is zero can be prepared by treating the phosphonous acid of formula IV with sodium metaperiodate to give the phosphonic acid

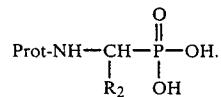 (XVII)

The acid of formula XVII is converted to the dimethyl ester by treatment with diazomethane and then the benzyloxycarbonyl group is removed by hydrogenation.

The compound of formula I wherein $R_{24}$ is

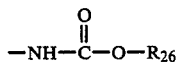

can be prepared by coupling the α-amino acid of the formula

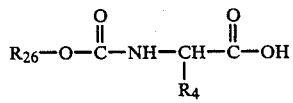

to the phosphinyl compound of formula II in the presence of triethylamine. Preferably, the acid of formula XVIII is first converted to an activated form as described previously. Removal of the $R_3$ and $R_6$ ester groups by conventional means gives the desired product.

When $R_{26}$ is benzyl, hydrogenation gives the compound of formula I wherein $R_{24}$ is $NH_2$. Similarly, when $R_{26}$ is $-C(CH_3)_3$ treatment with trifluoroacetic acid yields the compound wherein $R_{24}$ is $NH_2$.

The hydroxyalkanoyl amino or imino acid ester of formula V can be prepared by treating the carboxylic acid of the formula

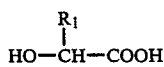

with the amino or imino acid ester of the formula

wherein $R_6$ in definition of X is an easily removable ester protecting group such as benzyl. Preferably, the hydrochloride salt of the ester of formula XX is employed and the reaction is performed in the presence of triethylamine and dicyclohexylcarbodiimide.

When the compounds of formula I contain a reactive sulfur atom within the amino acid portion of the molecule, i.e., X is

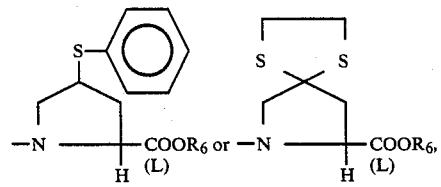

for example, then the above described procedures are somewhat altered to avoid the use of hydrogenation to remove the N-protecting groups.

For example, in this case, the phosphinyl compound of formula II could be prepared by treating the phosphonic acid of the formula

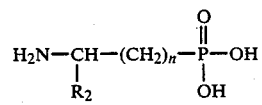

with 2-(trimethylsilyl)ethyl p-nitrophenyl carbonate to give

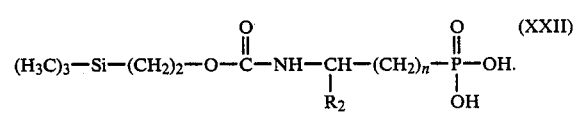

This N-protected compound is treated successively with the alcohol of formula XII in the presence of dicyclohexylcarbodiimide and phosphorus pentachloride to give the acid chloride of the formula

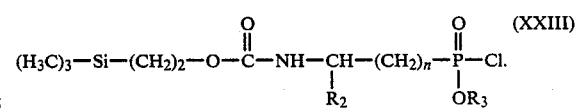

The acid chloride of formula XXIII is coupled to the hydroxyalkanoyl amino acid ester of formula V, wherein X contains a reactive sulfur atom, in the presence of triethylamine and dimethylaminopyridine to give

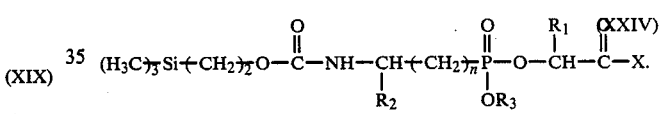

Removal of the trimethylsilylethoxycarbonyl protecting group by treatment with tetraethylammonium fluoride gives the desired phosphinyl compound of formula II.

The compounds of formula I wherein $R_{24}$ is

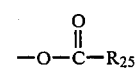

can be prepared by coupling the phosphinyl compound of formula II with the acid of the formula

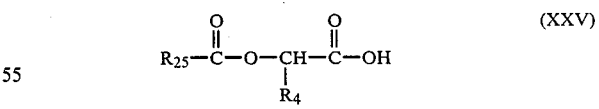

in the presence of triethylamine. This reaction is performed in the presence of a coupling agent such as dicyclohexylcarbodiimide or carbonyldiimidazole or by converting the acid of formula XXV to an activated form such as a mixed anhydride, for example, by employing pivaloyl chloride, an activated ester such as p-nitrophenol, or an acid chloride. Removal of the $R_3$ and $R_6$ ester groups by conventional means yields the desired diacid products of formula I.

The compound of formula I wherein $R_1$ or $R_4$ is

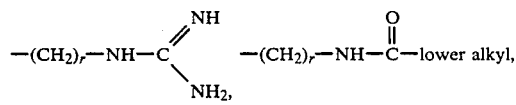

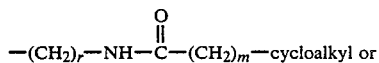

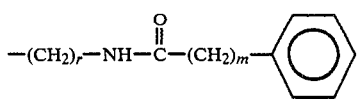

can be prepared by reacting the compound of formula I wherein $R_1$ or $R_4$ is $-(CH_2)_r-NH_2$ with 2-methyl-2-thiopseudourea or the appropriate acylating agent as the final step in the synthesis.

In the above reactions if any or all of $R_1$, $R_2$, $R_4$ and $R_{21}$ are

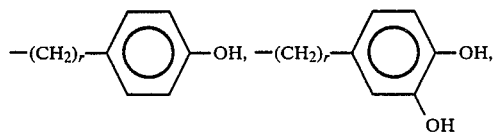

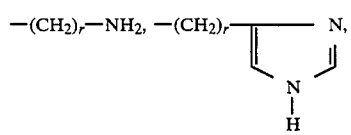

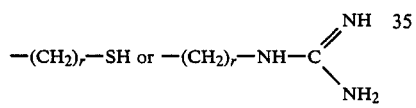

then the hydroxyl, amino, imidazolyl, mercaptan, or guanidinyl function should be protected during the coupling reaction. Suitable protecting groups include benzyloxycarbonyl, t-butoxycarbonyl, trifluoroacetyl, benzyl, benzhydryl, trityl, phthalidyl, etc., and nitro in the case of guanidinyl. The protecting group is removed by hydrogenation, treatment with acid, or other known methods following completion of the reaction.

The ester products of formula I wherein

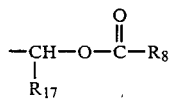

can be obtained by employing the hydroxyalkanoyl amino or imino acid of formula V in the above reactions with the ester group already in place.

The ester products of formula I wherein $R_6$ is

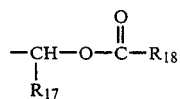

can also be obtained by treating the product of formula I wherein $R_6$ is hydrogen with a molar equivalent of the compound of the formula

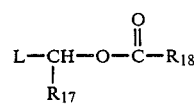

(XXVI)

wherein L is leaving group such as chlorine, bromine, tolylsulfonyloxy, etc. The diester products wherein $R_3$ and $R_6$ are the same and are both

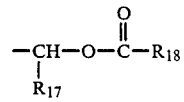

can be obtained by treating the product of formula I wherein $R_3$ and $R_6$ are both hydrogen with two or more equivalents of the compound of formula XXVI.

The ester products of formula I wherein $R_3$ is lower alkyl or

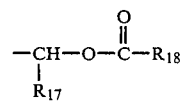

and $R_6$ is hydrogen can be obtained by treating the product of formula I wherein $R_3$ is hydrogen or an alkali metal salt and $R_6$ is benzyl or benzhydryl with the compound of the formula $$L-R_3 \quad (XXVII)$$

wherein L is as defined in formula XXVI and $R_3$ is as defined above. Removal of the $R_6$ ester group such as by hydrogenation yields the desired monoester products.

Preferred compounds of this invention with respect to the amino or imino acid part of the structure are those wherein

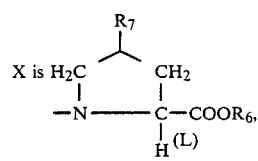

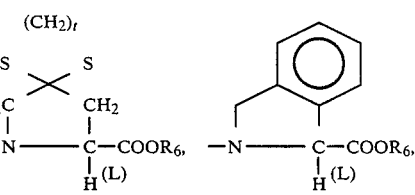

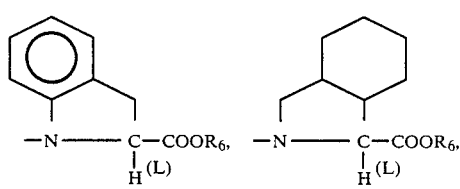

-continued

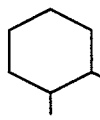 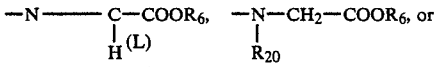

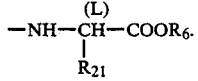

$R_7$ is hydrogen, hydroxy, chloro, fluoro, lower alkyl of 1 to 4 carbons, cyclohexyl, amino, —O-lower alkyl wherein lower alkyl is of 1 to 4 carbons, —S-lower alkyl wherein lower alkyl is of 1 to 4 carbons,

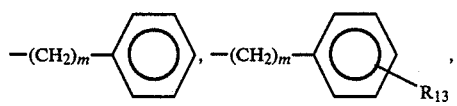

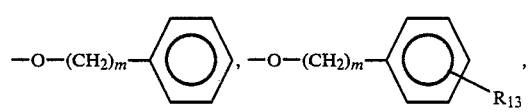

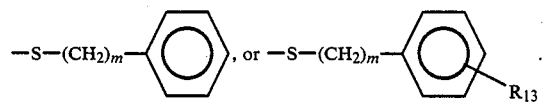

m is zero, one or two.
$R_{13}$ is methyl, methoxy, chloro, fluoro, bromo, methylthio, or hydroxy.
t is 2 or 3.
$R_{21}$ is hydrogen, straight or branched chain lower alkyl of 1 to 4 carbons,

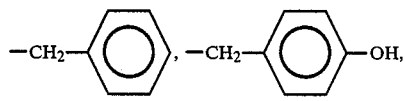

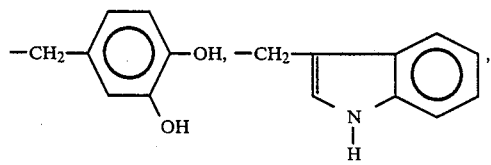

—(CH$_2$)$_4$—NH$_2$,

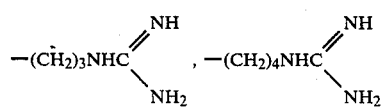

—CH$_2$—SH, —CH$_2$—S—CH$_3$,

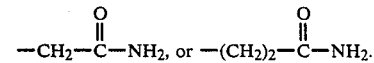

$R_{20}$ is

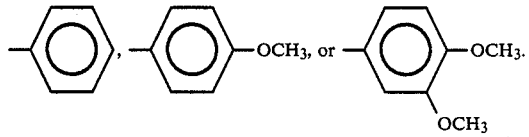

$R_6$ is hydrogen, sodium ion, potassium ion, calcium ion, lithium ion, or

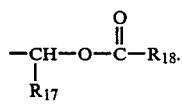

$R_{17}$ is hydrogen, straight or branched chain lower alkyl of 1 to 4 carbons, cyclohexyl, or phenyl.
$R_{18}$ is hydrogen or straight or branched chain lower alkyl of 1 to 4 carbons.
Most preferred are those wherein:

X is 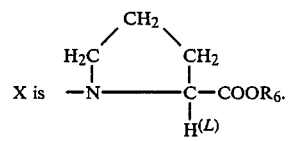

$R_6$ is hydrogen, sodium ion, potassium ion, calcium ion, or lithium ion.
Preferred compounds of this invention with respect to the phosphonate part of the structures are those wherein:
$R_1$ is straight or branched chain lower alkyl of 1 to 4 carbons, —(CH$_2$)$_r$—NH$_2$, or

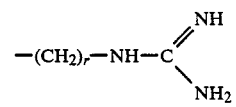

$R_2$ is straight or branched chain lower alkyl of 1 to 4 carbons,

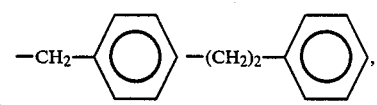

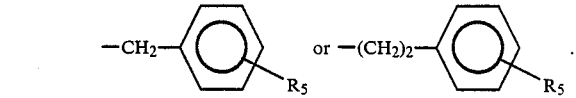

$R_3$ is hydrogen, sodium ion, potassium ion, calcium ion, lithium ion, or

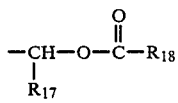

R₄ is hydrogen, straight or branched chain lower alkyl of 1 to 4 carbons, —(CH₂)ᵣ—NH₂,

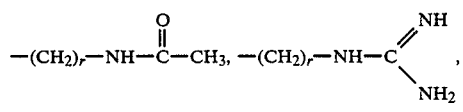

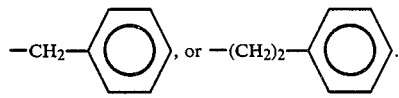

R₂₄ is —NH₂, —NH—C(=O)—R₂₅,

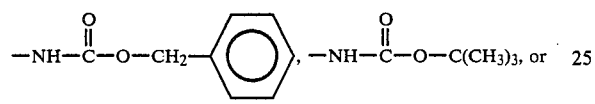

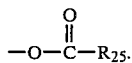

R₂₅ is —(CH₂)ₘ-cyclopropyl, —(CH₂)ₘ-cyclobutyl, —(CH₂)ₘ-cyclopentyl, —(CH₂)ₘ-cyclohexyl,

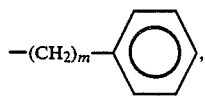

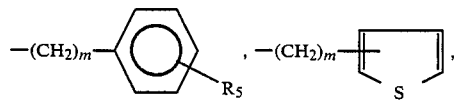

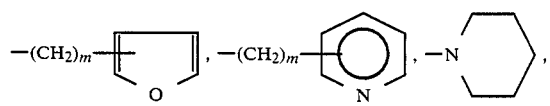

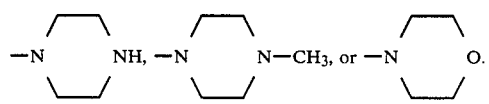

r is an integer from 3 to 5.
m is zero, one or two.
R₅ is methyl, methoxy, methylthio, chloro, bromo, fluoro, or hydroxy.
R₁₇ is hydrogen, straight or branched chain lower alkyl of 1 to 4 carbons, cyclohexyl, or phenyl.
R₁₈ is hydrogen or straight or branched chain lower alkyl of 1 to 4 carbons.
Most preferred are those wherein:
n is zero.
R₁ is —CH₃ or —(CH₂)₄—NH₂.
R₂ is methyl, n-butyl, or benzyl.
R₃ is hydrogen, sodium ion, potassium ion, calcium ion, or lithium ion.

R₄ is methyl, n-butyl, —(CH₂)₄—NH₂,

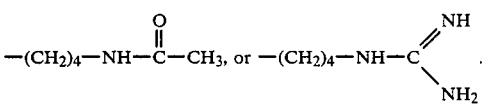

R₂₄ is —NH₂,

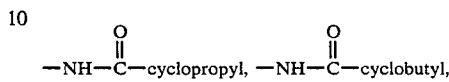

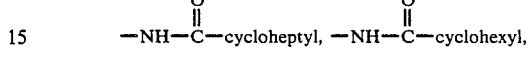

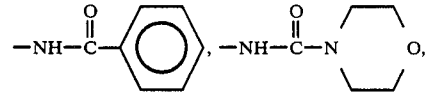

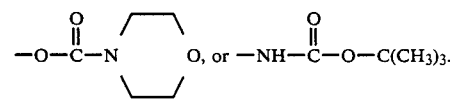

The compounds of formula I wherein at least one of R₃ and R₆ is hydrogen form salts with a variety of inorganic or organic bases. The nontoxic, pharmaceutically acceptable salts are preferred, although other salts are also useful in isolating or purifying the product. Such pharmaceutically acceptable salts include alkali metal salts such as sodium, potassium or lithium, alkaline earth metal salts such as calcium or magnesium, and salts derived from amino acids such as arginine, lysine, etc. The salts are obtained by reacting the acid form of the compound with an equivalent of the base supplying the desired ion in a medium in which the salt precipitates or in aqueous medium and then lyophilizing.

As shown above, the amino or imino acid or ester portion of the molecule of the products of formula I as represented by X is in the L-configuration. Also, the products of formula I wherein R₁ and R₄ are other than hydrogen contain three asymmetric centers in the phosphonate portion of the molecule as represented by the * in formula I. Additional asymmetric centers are present in the ester products when R₁₇ is other than hydrogen. Thus, the compounds of formula I can exist in diastereomeric forms or in mixtures thereof. The above described processes can utilize racemates, enantiomers or diastereomers as starting materials. When diastereomeric products are prepared, they can be separated by conventional chromatographic or fractional crystallization methods.

The products of formula I wherein the imino acid ring is monosubstituted give rise to cis-trans isomerism. The configuration of the final product will depend upon the configuration of the R₇, R₈ and R₉ substituent in the starting material of formula V.

The compounds of formula I, and the pharmaceutically acceptable salts thereof, are hypotensive agents. They inhibit the conversion of the decapeptide angiotensin I to angiotensin II and, therefore, are useful in reducing or relieving angiotensin related hypertension. The action of the enzyme renin on angiotensinogen, a pseudoglobulin in blood plasma, produces angiotensin I. Angiotensin I is converted by angiotensin coverting enzyme (ACE) to angiotensin II. The latter is an active pressor substance which has been implicated as the causative agent in several forms of hypertension in various mammalian species, e.g., humans. The compounds of this invention intervene in the angiotensinogen → (renin) → angiotensin I → angiotensin II sequence by inhibiting angiotensin converting enzyme and reducing or eliminating the formation of the pressor substance angiotensin II. Thus by the administration of a composition containing one (or a combination) of the compounds of this invention, angiotensin dependent hypertension in a species of mammal (e.g., humans) suffering therefrom is alleviated. A single dose, or preferably two to four divided daily doses, provided on a basis of about 0.1 to 100 mg., preferably about 1 to 50 mg., per kg. of body weight per day is appropriate to reduce blood pressure. The substance is preferably administered orally but parenteral routes such as the subcutaneous, intramuscular, intravenous or intraperitoneal routes can also be employed.

The compounds of this invention can also be formulated in combination with a diuretic for the treatment of hypertension. A combination product comprising a compound of this invention and a diuretic can be administered in an effective amount which comprises a total daily dosage of about 30 to 600 mg., preferably about 30 to 330 mg. of a compound of this invention, and about 15 to 300 mg., preferably about 15 to 200 mg. of the diuretic, to a mammalian species in need thereof. Exemplary of the diuretics contemplated for use in combination of this invention are the thiazide diuretics, e.g., chlorothiazide, hydrochlorothiazide, flumethiazide, hydroflumethiazide, bendroflumethiazide, methyclothiazide, trichloromethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration, or in sterile solutions or suspensions for parenteral administration. About 10 to 500 mg. of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The compounds of formula I wherein X is

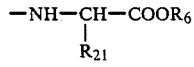

also possess enkephalinase inhibition activity and are useful as analgesic agents. Thus, by the administration of a composition containing one or a combination of such compounds of formula I or a pharmaceutically acceptable salt thereof, pain is alleviated in the mammalian host. A single dose, or preferably two to four divided daily doses, provided on a basis of about 0.1 to about 100 mg. per kilogram of body weight per day, preferably about 1 to about 50 mg. per kilogram per day, produces the desired analgesic activity. The composition is preferably administered orally but parenteral routes such as subcutaneous can also be employed.

The following examples are illustrative of the invention. Temperatures are given in degrees centigrade.

HP-20 refers to a porous crosslinked polystyrene-divinyl benzene polymer resin.

EXAMPLE 1

1-[(S)-2-[[[1-[[(S)-6-Amino-2-[(cyclobutylcarbonyl)amino]-1-oxohexyl]amino]pentyl]hydroxyphosphinyl]oxy]-1-oxopropyl]-L-proline (a) [1-[(Diphenylmethyl)amino]pentyl]phosphinic acid A solution of 50% aqueous hypophosphorous acid (55 g., 0.296 mole) in dioxane (100 ml.) is added all at once to a solution of diphenylmethylamine (0.296 mole) in dioxane (100 ml.) with vigorous stirring. The salt crystallizes within minutes from the resulting warm solution. After refrigeration, 65.7 g. of diphenylmethylamine, phosphinate is recovered by filtration; m.p. 171°–173°.

A mixture of diphenylmethylamine, phosphinate (6.25 g., 24 mmole) and valeraldehyde (20 ml., 190 mmole, freshly distilled) is warmed at 65°–70° for 15 minutes. The resulting semisolid mass is diluted to a volume of 75 ml. with ethanol. The solid that separates from solution is collected by filtration and washed with ether to give 3.8 g. of [1-[(diphenylmethyl)amino]pentyl]phosphinic acid; m.p. 203°–205° (turbid melt).

(b) (1-Aminopentyl)phosphinic acid

A mixture of [1-[(diphenylmethyl)amino]pentyl]phosphinic acid (5 g., 15 mmole), anisole (5 ml.) and trifluoroacetic acid (50 ml.) is refluxed for one hour under argon. It is then partitioned between water (100 ml.) and ether (100 ml.). The aqueous layer is filtered and concentrated in vacuo, chasing traces of solvent several times with ethanol. This gives a white solid which is triturated with acetonitrile and dried overnight in vacuo to give 1.49 g. of (1-aminopentyl)phosphinic acid.

(c) [1-[[(Phenylmethoxy)carbonyl]amino]pentyl]phosphinic acid

The pH of a solution of (1-aminopentyl) phosphinic acid (1.95 g., 12.9 mmole) in water (50 ml.) is adjusted to 9.5 by the addition of 2.5 N sodium hydroxide. After cooling to 0°, benzyl chloroformate (1.95 ml., 2.2 g., 12.9 mmole) is added in small portions with additional sodium hydroxide to maintain a pH of 9.5. The mixture is stirred for 2 hours at 0° at pH 9.5. The reaction mixture is then extracted with ether. It is then acidified with concentrated hydrochloric acid to pH 2, and then extracted with ethyl acetate. The combined ethyl acetate extracts are dried over sodium sulfate and concentrated in vacuo to give 2.93 g. of [1-[[(phenylmethoxy) carbonyl]amino]pentyl]phosphinic acid.

(d) 1-[(S)-2-Hydroxy-1-oxopropyl]-L-proline, phenylmethyl ester

A mixture of sodium lactate (1.7 g., 15.0 mmole), diphenylphosphorylazide (3.6 ml., 1.1 eq.), and dry dimethylformamide (30 ml.) at 0° (ice-bath) in an argon atmosphere is treated with triethylamine (2.1 ml., 1.0 eq.) and L-proline, phenylmethyl ester, monohydrochloride salt (3.6 g., 15.0 mmole). After 24 hours, the reaction mixture is partitioned between ethyl acetate and water. The aqueous phase is back extracted, the organic extracts are combined, washed with 5% potassium bisulfate, brine, and evaporated. The residue (5 g.)

is chromatographed on silica (130 g.) eluting with (1:1, ethyl acetate/hexane) to give 2.5 g. of 1-[(S)-2-hydroxy-1-oxopropyl]-L-proline, phenylmethyl ester as a white crystalline solid after evaporation; m.p. 86°–88° (isopropyl ether). TLC (silica gel; ethyl acetate) $R_f$=0.4.

Anal. calc'd. for $C_{15}H_{19}NO_4$: C, 64.97; H, 6.91; N, 5.05. Found: C, 64.70; H, 6.85; N, 5.02.

(e)

1-[(S)-2-[[Hydroxy[1-[[(phenylmethoxy)carbonyl]amino]pentyl]phosphinyl]oxy]-1-oxopropyl]-L-proline, phenylmethyl ester 1-[(S)-2-Hydroxy-1-oxopropyl]-L-proline, phenylmethyl ester (2.55 g., 9.2 mmole) and [1-[[(phenylmethoxy)carbonyl]amino]pentyl]phosphinic acid (3.93., 13.8 mmole) are suspended in dry tetrahydrofuran (50 ml.) under argon. Dicyclohexylcarbodiimide (2.84 g., 13.8 mmole) and dimethylaminopyridine (470 mg., 3.8 mmole) are added. This mixture is stirred for 6 hours under argon. An additional amount of dicyclohexylcarbodiimide (2 g.) is added and the reaction is stirred overnight.

The reaction mixture is filtered to remove dicyclohexyl urea. Ethyl acetate is added, and the resulting solution is washed with 5% potassium bisulfate, saturated sodium bicarbonate, and brine. It is filtered again to remove dicyclohexyl urea and concentrated in vacuo to a yellow oil. This oil is chromatographed on silica eluting with hexane:acetate (3:2). Fractions 9–21 (50 ml. each) are concentrated in vacuo to give 3.61 g. of a clear, colorless oil.

This oil is dissolved in dioxane (50 ml.). A solution of sodium metaperiodate (2.5 g., 11.7 mmole) in water (30 ml.) is added. The mixture is stirred for 4 hours at room temperature. The reaction is then partitioned between ethyl acetate and water acidified with 5% potassium bisulfate. The ethyl acetate layer is washed with dilute bisulfite solution to decolorize and then washed with brine. It is dried over sodium sulfate and concentrated to an oil.

This crude oil is dissolved in a minimum amount of ethyl acetate, and a solution of adamantaneamine (1.4 g., 9.2 mmole) in ether (50 ml.) is added. The solid that precipitates is repeatedly triturated with hexanes, and then partitioned between ethyl acetate and 1N hydrochloric acid. The ethyl acetate layer is washed with brine, dried over sodium sulfate, and concentrated in vacuo to give 600 mg. of product.

The ether-ethyl acetate supernatant and the hexane washings from the above trituration are combined and concentrated to an oil which is dissolved in saturated sodium bicarbonate (500 ml.). The bicarbonate solution is washed repeatedly with ether to remove non-polar impurities. An oily layer forms between the ether and bicarbonate layers. This layer and the bicarbonate layer are acidified and extracted with ethyl acetate. The ethyl acetate solution is washed with brine, dried over sodium sulfate, filtered, and concentrated to give 1.2 g. of clear oil. This is combined with the product obtained previously to give 1.8 g. of 1-[(S)-2-[[hydroxy[1-[[(phenylmethoxy)carbonyl]amino]pentyl]phosphinyl]oxy]-1-oxopropyl]-L-proline, phenylmethyl ester.

(f)

1-[(S)-2-[[(1-Aminopentyl)hydroxyphosphinyl]oxy]-1-oxopropyl]-L-proline

The phenylmethyl ester product from part (e) (1.8 g., 3.2 mmole) is dissolved in methanol (50 ml.). 10% Palladium hydroxide on carbon catalyst (280 mg.) is added. The mixture is stirred for 6 hours under atmospheric hydrogen. The methanol solution is filtered through Celite and concentrated in vacuo to give 780 mg. of white solid 1-[(S)-2-[[(1-aminopentyl)hydroxyphosphinyl]oxy]-1-oxopropyl]-L-proline.

(g)

$N^2$-(Cyclobutylcarbonyl)-$N^6$-[(phenylmethoxy)carbonyl]-L-lysine $N^6$-[(Phenylmethoxy)carbonyl]-L-lysine (4.73 g., 16.9 mmole) is suspended in acetonitrile (50 ml.). Bis(trimethylsilyl)trifluoroacetamide (18.5 ml., 17.92 g., 69.9 mmole) is added and the mixture is stirred for 45 minutes under argon (the mixture becomes homogeneous). After cooling to 5°, a solution of cyclobutane carboxylic acid chloride (2.02 g., 17 mmole) in tetrahydrofuran (10 ml.) is added dropwise over 15 minutes. The reaction mixture is stirred for 2 hours and TLC (silica gel; isopropanol:ammonia:water, 7:2:1) shows formation of product ($R_f$=0.62).

The reaction mixture is partitioned between ethyl acetate and water. The ethyl acetate layer is concentrated to an oil which is dissolved in saturated bicarbonate solution and washed with ethyl acetate. The aqueous layer is acidified to pH 2 with concentrated hydrochloric acid, and extracted with ethyl acetate. The ethyl acetate extract is dried over sodium sulfate and concentrated in vacuo to give 5.46 g. of $N^2$-(cyclobutylcarbonyl)-$N^6$-[(phenylmethoxy)carbonyl]-L-lysine.

Anal. calc'd. for $C_{19}H_{26}N_2O_5 \cdot 0.8$ $H_2O$: C, 60.47; H, 7.37; N, 7.42. Found: C, 60.47; H, 6.91; N, 7.82.

(h)

1-[(S)-2-[[[1-[[(S)-2-[(Cyclobutylcarbonyl)amino]-6-[[(phenylmethoxy)carbonyl]amino]-1-oxohexyl]amino]pentyl]hydroxyphosphinyl]oxy]-1-oxopropyl]-L-proline 1-[(S)-2-[[(1-Aminopentyl)hydroxyphosphinyl]oxy]-1-oxopropyl]-L-proline (304 mg., 0.9 mmole) is persilylated by stirring under argon with bis(trimethylsilyl)trifluoroacetamide (1.6 ml., 1.55 g., 6 mmole) in acetonitrile (3 ml.) until homogeneous (1 hour).

$N^2$-(Cyclobutylcarbonyl)-$N^6$-[(phenylmethoxy)carbonyl]-L-lysine (362 mg., 1 mmole) is dissolved in tetrahydrofuran (1 ml.) with N-methylmorpholine (2 mmole) under argon and cooled to −20°. Isobutyl chloroformate is added and a white precipitate appears. The mixture is stirred for 20 minutes at −20°. The solution of persilyated phospinyl L-proline is added all at once. The temperature of the solution rises to 0°. It is rapidly cooled to −20° and stirred for one hour at this temperature and then one hour at room temperature.

The reaction mixture is partitioned between ethyl acetate and 5% potassium bisulfate. The ethyl acetate layer is washed with brine, dried over sodium sulfate, and concentrated in vacuo to give 670 mg. of white solid mixture of 1-[(S)-2-[[[1-[[(S)-2-[(cyclobutylcarbonyl)amino]-6-[[(phenylmethoxy)carbonyl]amino]-1-oxohexyl]amino]pentyl]hydroxyphosphinyl]oxy]-1-oxopropyl]-L-proline; TLC (silica gel; isopropanol:ammonia: water, 7:2:1) $R_f$=0.51, and recovered $N^2$-(cyclobutylcarbonyl)-$N^6$-[(phenylmethoxy)carbonyl]-L-lysine ($R_f$=0.71).

(i)
1-[(S)-2-[[[1-[[(S)-6-Amino-2-[(cyclobutylcarbonyl)amino]-1-oxohexyl]amino]pentyl]hydroxyphosphinyl]oxy]-1-oxopropyl]-L-proline The mixture obtained as the product in part (h) is dissolved in methanol (25 ml.). 10% Palladium on carbon catalyst (70 mg.) is added, and the mixture is stirred for 2 hours under atmospheric pressure hydrogen. The methanol solution is filtered through Celite and concentrated to a white glass. This material is chromatographed (HP-20) using a 1:1 gradient from water to acetonitrile. Fractions containing the desired product are rechromatographed (HP-20) using a gradient from water to 7:3 water:acetonitrile to remove traces of impurities. Fractions containing the desired product are combined, filtered, and lyophilized to give 140 mg. of solid 1-[(S)-2-[[[1-[[(S)-6-amino-2-[(cyclobutylcarbonyl)amino]-1-oxohexyl]-amino]pentyl]hydroxyphosphinyl]oxy]-1-oxopropyl]-L-proline; forms glass at 100°, melts at 215°; $[\alpha]_D = -47.4°$ (c=0.5, methanol). TLC (silica gel; isopropanol:ammonia:water) $R_f=0.33$.

Anal. cal'd. for $C_{24}H_{43}N_4O_8P \cdot 2.75\ H_2O$: C, 48.36; H, 8.20; N, 9.40; P, 5.20. Found: C, 48.32; H, 8.04; N, 9.45; P, 4.90.

EXAMPLE 2

1-[(S)-6-Amino-2-[[[1-[[(S)-6-Amino-2-[(cyclobutylcarbonyl)amino]-1-oxohexyl]amino]-2-phenylethyl]hydroxyphosphinyl]oxy]-1-oxohexyl]-L-proline (a)
[2-Phenyl-1-[[(phenylmethoxy)carbonyl]amino]-ethyl]-phophinic acid (1-Amino-2-phenylethyl)phosphinic acid (1 g., 5.4 mmole) is suspended in water (25 ml.) at 0° and the pH is adjusted to 9.5 with concentrated sodium hydroxide solution. Benzyl chloroformate (0.9 ml., 1.08 g., 6.3 mmole) is added while the pH is maintained at 9.5 by the addition of sodium hydroxide. After the pH stabilizes, the mixture is stirred for 3 hours at room temperature. The basic solution is washed with ether and then acidified. The white solid precipitate is collected on a frit to give [2-phenyl-1-[[(phenylmethoxy)carbonyl]amino]ethyl]-phosphinic acid. TLC (silica gel; isopropanol:ammonia:water, 7:2:1) $R_f=0.75$.

(b)
[2-Phenyl-1-[[(phenylmethoxy)carbonyl]amino]-ethyl]-phosphonic acid

The crude phosphinic acid product from part (a) is dissolved in water (5 ml.) with dioxane (5 ml.) and treated with sodium periodate (1.4 g., 6.5 mmole). After stirring overnight, the reaction mixture is partitioned between ethyl acetate and acidic water. The ethyl acetate solution is washed with dilute acidic bisulfite and brine, and dried over sodium sulfate. It is filtered and concentrated to give 1.28 g. of [2-phenyl-1-[[(phenylmethoxy)carbonyl]-amino]ethyl]phosphonic acid as a clear oil. TLC (silica gel; isopropanol:ammonia:water, 7:2:1) $R_f=0.30$.

(c)
[2-Phenyl-1-[[(phenylmethoxy)carbonyl]amino]-ethyl]-phosphonic acid, dimethyl ester The phosphonic acid product from part (b) (1 g., 2.98 mmole) is suspended in ethyl acetate (100 ml.). A solution of diazomethane (prepared from 2 g. of N-methyl-N'-nitro-N-nitrosoguanidine, 25 ml. of ether, and 6 ml. of 40% potassium hydroxide) is added gradually until all of the suspended solid is dissolved and the yellow diazomethane color persists. A few drops of acetic acid are added to destroy excess diazomethane. The ethyl acetate solution is washed with saturated bicarbonate and brine, dried over sodium sulfate, filtered, and concentrated to give 1.0 g. of [2-phenyl-1-[[(phenylmethoxy)-carbonyl]amino]ethyl]phosphonic acid, dimethyl ester as an oil. TLC (silica gel; hexane:acetone, 1:1) $R_f=0.18$.

(d) (1-Amino-2-phenylethyl)phosphonic acid, dimethyl ester

The dimethyl ester product from part (c) (1 g., 2.8 mmole) is dissolved in methanol (100 ml.) and stirred under atmospheric hydrogen with 20% palladium hydroxide on carbon catalyst (120 mg.) for 4 hours. The mixture is filtered and concentrated in vacuo to give 622 mg. of (1-amino-2-phenylethyl)phosphonic acid, dimethyl ester. TLC (silica gel; isopropanol:ammonia:water, 7:2:1) $R_f=0.76$.

(e)
[1-[[$N^2$-(Cyclobutylcarbonyl)-$N^6$-[(phenylmethoxy)carbonyl]-L-lysyl]amino]-2-phenylethyl]phosphonic acid, dimethyl ester $N^2$-(Cyclobutylcarbonyl)-$N^6$-[(phenylmethoxy)carbonyl]-L-lysine (977 mg., 2.7 mmole) [prepared as set forth in Example 1(g)] is dissolved in dry tetrahydrofuran (15 ml.) under argon and cooled to 0°. Triethylamine (0.45 ml., 0.32 g., 3.2 mmole) is added followed by trimethylacetyl chloride (0.38 ml., 0.37 g., 3.1 mmole) and dimethylaminopyridine (140 mg., 1.1 mmole). The resulting white suspension is stirred for one hour at 0°. A solution of (1-amino-2-phenylethyl)phosphonic acid, dimethyl ester (622 mg., 2.7 mmole) in dichloromethane (15 ml.) is then added. The reaction mixture is warmed to room temperature and stirred for 72 hours. It is then partitioned between ethyl acetate and 5% potassium bisulfate. The ethyl acetate layer is washed with 5% potassium bisulfate, saturated bicarbonate, and brine, and dried over sodium sulfate. It is then concentrated to an oil (1.5 g.) which is chromatographed on silica gel (150 ml. of LPS-1) eluting with acetone:hexane (1:1). The product containing fractions are combined and concentrated to give 1.04 g. of [1-[[$N^2$-(cyclobutylcarbonyl)-$N^6$-[(phenylmethoxy)-carbonyl]-L-lysyl]amino]-2-phenylethyl]phosphonic acid, dimethyl ester as a clear oil. TLC (silica gel; acetone:hexane, 1:1) $R_f=0.14$.

(f)
[1[[$N^2$-(Cyclobutylcarbonyl)-$N^6$-[(phenylmethoxy)carbonyl]-L-lysyl]amino]-2-phenylethyl]phosphonic acid The dimethyl ester product from part (e) (1.04 g., 1.81 mmole) is dissolved in dichloromethane (10 ml.) and treated with trimethysilylbromide (0.52 ml., 605 mg., 3.96 mmole). The mixture is stirred under argon overnight then concentrated in vacuo. Dioxane (15 ml.) and water (5 ml.) are added and the resulting mixture is stirred for 15 minutes and then concentrated. Residual water is chased three times with acetonitrile (20 ml.) giving 1.06 g. of [1-[[$N^2$-(cyclobutylcarbonyl)-$N^6$-[(phenylmethoxy)carbonyl]-L-lysyl]-2-phenylethyl]-phosphonic acid as an organe-yellow foam. TLC (silica gel; isopropanol:ammonia:water, 7:2:1) $R_f=0.42$.

(g) (S)-6-Amino-2-hydroxyhexanoic acid

An aqueous solution of L-lysine, monohydrochloride (18.3 g., 0.1 mole) is passed through an AG 3-X4A (100–200 mesh) ion exchange column (OH form, 500 ml. bed volume) eluting with water. The ninhydrin positive fractions are combined, acidified with 2M (4N) sulfuric acid (100 ml., 0.2 mole) and evaporated to dryness.

The crude L-lysine, disulfuric acid salt is taken up in 10% sulfuric acid (250 ml.) and treated dropwise with a solution of sodium nitrite (25.9 g., 0.36 mole) in water (100 ml.) at 45°–50° (bath temperature) over a period of 2 hours. When the addition is complete, the mixture is stirred at 45°–50° for an additional 4.5 hours, the excess nitrous acid is decomposed with urea and the mixture is poured onto an AG-50-X8 ion exchange column (H+ form, 200 ml. bed volume). The column is eluted with water and then aqueous ammonia (concentrated ammonia-water, 1:3) to elute the product. The ninhydrin positive fractions are combined and evaporated to give a pink semi-solid which is recrystallized from water-ethanol to give 8.20 g. of (S)-6-amino-2-hydroxyhexanoic acid as white crystals; m.p. 197°–199°; $[\alpha]^{22} = -12.2°$ (c=1.2, water). TLC(silica gel; isopropanol:concentrated ammonia:water, 7:2:1) $R_f=0.16$ (contains trace of lysine, $R_f=0.12$).

(h) (S)-6-[[(Phenylmethoxy)carbonyl]amino]-2-hydroxyhexanoic acid

A solution of (S)-6-amino-2-hydroxyhexanoic acid (7.5 g., 51.0 mmole) in 1N sodium hydroxide solution (50 ml.) at 0° (ice-bath) is adjusted to pH 10.0 with concentrated hydrochloric acid and treated with benzyl chloroformate (8.4 ml., 95%, 55.9 mmole) in approximately 1 ml. portions at 15 minute intervals. Throughout the reaction, the pH is maintained at pH 9.8–10.2 by the addition of 1N sodium hydroxide solution. When the addition is complete and the pH stabilized, the mixture is stirred at pH 10, 0° for an additional 45 minutes, and then washed with one portion of ethyl ether. The aqueous solution is acidified to pH 1 with concentrated hydrochloric acid and extracted with ethyl acetate. The ethyl acetate extract is washed with saturated sodium chloride solution, dried over sodium sulfate, and evaporated. The residue is crystallized from isopropyl ether to give 13.5 g. of crude product as a white solid. Recrystallization of the crude product from ethyl acetate-hexane gives 11.48 g. of (S)-6-[[(phenylmethoxy)carbonyl]amino]-2-hydroxyhexanoic acid as a white crystalline solid; m.p. 79–81°; $[\alpha]^{22} = +4.5°$, $[\alpha]_{365} = +26.8°$ (c=1.1, chloroform). TLC (silica gel; acetic acid:methanol:methylene chloride, 1:1:20) $R_f=0.19$.

(i) 1-[(S)-6-[[(Phenylmethoxy)carbonyl]amino]b 2-hydroxy-1-oxohexyl]-L-proline, phenylmethyl ester A mixture of (S)-6-[[(phenylmethoxy)carbonyl]amino]-2-hydroxyhexanoic acid (1.4 g., 5.0 mmole), L-proline, phenylmethyl ester, monohydrochloride (1.33 g., 5.5 mmole), and triethylamine (0.76 ml., 5.5 mmole) in dry tetrahydrofuran (15 ml.) at 0° (ice-bath) is treated with 1-hydroxybenzotriazole hydrate (0.71 g., 5.26 mmole) and dicyclohexylcarbodiimide (1.08 g., 5.23 mmole). The solution is stirred at 0° for 3 hours, then allowed to warm to room temperature and stirred for an additional one hour. The mixture is filtered, diluted with ethyl acetate, and washed successively with 5% potassium bisulfate, saturated sodium bicarbonate, and saturated sodium chloride, dried over sodium sulfate, and evaporated. The residue is taken up in carbon tetrachloride, filtered to remove the last traces of dicyclohexyl urea, and evaporated. The crude product is purified by flash chromatography on silica gel (35 g., Whatman LPS-1) eluting with ethyl acetate-hexane (2:1) to give 2.24 g. of 1-[(S)-6-[[(phenylmethoxy)carbonyl]amino]-2-hydroxy-1-oxohexyl]-L-proline, phenylmethyl ester as a colorless, very viscous oil. TLC (silica gel; methanol:methylene chloride, 5:95) $R_f=0.36$.

(j) 1-[(S)-6-[[(Phenylmethoxy)carbonyl]amino]-2-[[[1-[[(S)-6-[[(phenylmethoxy)carbonyl]amino]-2-[(cyclobutylcarbonyl)amino]-1-oxohexyl]amino]-2-phenylethyl]hydroxyphosphinyl]oxy]-1-oxohexyl]-L-proline, phenylmethyl ester

[1-[[N²-(Cyclobutylcarbonyl)-N⁶-[(phenylmethoxy)carbonyl]-L-lysyl]amino]-2-phenylethyl]phosphonic acid (500 mg., 0.91 mmole) is dissolved in pyridine (10 ml.) with 1-[(S)-6-[[(phenylmethoxy)carbonyl]amino]-2-hydroxy-1-oxohexyl]-L-proline, phenylmethyl ester (426 mg., 0.91 mmole). Dicyclohexylcarbodiimide (224 mg., 1.09 mmoles) is added and the mixture is stirred at room temperature overnight. It is then concentrated in vacuo and partitioned between ethyl acetate and 5% potassium bisulfate after filtering to remove dicyclohexyl urea. The ethyl acetate layer is washed with brine, dried over sodium sulfate, and concentrated to give 1-[(S)-6-[[(phenylmethoxy)carbonyl]amino]-2-[[[1-[[(S)-6-[[(phenylmethoxy)carbonyl]amino]-2-[(cyclobutylcarbonyl)amino]-1-oxohexyl]amino]-2-phenylethyl]hydroxyphosphinyl]oxy]-1-oxohexyl]-L-proline, phenylmethyl ester as a crude oil. TLC (silica gel; dichloromethane:methanol:acetic acid, 20:1:1) $R_f=0.33$.

(k) 1-[(S)-6-Amino-2-[[[1-[[(S)-6-amino-2-[(cyclobutylcarbonyl)amino]-1-oxohexyl]amino]-2-phenylethyl]hydroxyphosphinyl]oxy]-1-oxohexyl]-L-proline The phenylmethyl ester product from part (j) is dissolved in methanol (50 ml.) and stirred under atmospheric hydrogen with 20% palladium hydroxide on carbon catalyst (120 mg.) overnight. The solution is filtered through Celite and concentrated to an oil. This oil is chromatographed (HP-20) eluting with a 1:1 acetonitrile:water gradient. The product containing fractions are combined and concentrated to a glass. This glass is dissolved in water, filtered (millipore), frozen and lyophilized to give 253 mg. of solid 1-[(S)-6-amino-2-[[[1-[[(S)-6-amino-2-[(cyclobutylcarbonyl)amino]-1-oxohexyl]amino]-2-phenylethyl]hydroxyphosphinyl]oxy]-1-oxohexyl]-L-proline; forms a glass at 200°; $[\alpha]_D = -18.5$ (c=1.0, methanol). TLC (silica gel; isopropanol:ammonia:water, 7:2:1) $R_f=0.17$ and 0.21.

Anal. calc'd. for $C_{30}H_{48}N_5O_8P \cdot 4.4 H_2O$ C, 50.29; H, 7.99; N, 9.78; P, 4.32. Found: C, 50.29; H, 7.89; N, 9.59; P, 4.10.

EXAMPLE 3

1-[(S)-2-[[[1-[[(S)-6-Amino-2-[(cyclobutylcarbonyl)amino]-1-oxohexyl]amino]-2-phenylethyl]hydroxyphosphinyl]oxy]-1-oxopropyl]-L-proline (a)

1-[(S)-2-[[Hydroxy[2-phenyl-1-[[(phenylmethoxy)carbonyl]amino]ethyl]phosphinyl]oxy]-1-oxopropyl]-L-proline, phenylmethyl ester A mixture of [2-phenyl-1-[[(phenylmethoxy)carbonyl]amino]ethyl]phosphinic acid (3.19 g., 10 mmole) [prepared as described in Example 2 (a)] and 1-[(S)-2-hydroxy-1-oxopropyl]-L-proline, phenylmethyl ester (2.7 g., 10 mmole) in dichloromethane (30 ml.) is treated with dicyclohexylcarbodiimide (2.2 g., 11 mmole) and dimethylaminopyridine (350 mg.) under argon. After stirring for 4 hours at room temperature, an additional amount of dicyclohexylcarbodiimide (1.5 g.) and dimethylaminopyridine (100 mg.) are added. The reaction mixture is stirred for an additional 2 hours and then filtered to remove dicyclohexyl urea. Ethyl acetate is added, and the resulting solution is washed with 5% potassium bisulfate, saturated sodium bicarbonate, and brine. It is filtered again to remove dicyclohexyl urea and concentrated in vacuo to an oil.

This oil is dissolved in dioxane (15 ml.). A solution of sodium metaperiodate (2.34 g.) in water (15 ml.) is added. The mixture is stirred for 4 hours at room temperature. The reaction is partitioned between ethyl acetate and acidified water. The ethyl acetate layer is washed with dilute bisulfite solution to decolorize and then brine. It is dried over sodium sulfate and concentrated to an oil.

This crude oil is dissolved in a minimum amount of ethyl acetate, and a solution of adamantanamine (1.8 g.) in ether (50 ml.) is added. The solid that precipitates is repeatedly triturated with hexanes, and then partitioned between ethyl acetate and 1N hydrochloric acid. The ethyl acetate layer is washed with brine, dried over sodium sulfate, and concentrated in vacuo to give the desired product. Additional product is recovered from the ether-ethyl acetate supernatant and the hexane washings to give a total of 4.12 g. of 1-[(S)-2-[[hydroxy[2-phenyl-1-[[(phenylmethoxy)carbonyl]amino]ethyl]phosphinyl]oxy]-1-oxopropyl]-L-proline, phenylmethyl ester.

(b)

1-[(S)-2-[[Hydroxy[2-phenyl-1-[[(phenylmethoxy)carbonyl]amino]ethyl]phosphinyl]oxy]-1-oxopropyl]-L-proline The phenylmethyl ester product from part (a) (4.12 g., 6.9 mmole) is dissolved in dioxane (15 ml.) and 1N lithium hydroxide (15 ml.). Ethanol (several ml.) is added to solubilize the salts, and the reaction mixture is stirred overnight at room temperature under argon. The reaction mixture is diluted with water and washed with ether and ethyl acetate. This aqueous solution is acidified and extracted with ethyl acetate. This ethyl acetate solution is washed with brine, dried over sodium sulfate, and concentrated to give 1-[(S)-2-[[hydroxy[2-phenyl-1-[[(phenylmethoxy)carbonyl]amino]ethyl]phosphinyl]oxy]-1-oxopropyl]-L-proline as a viscous white oil.

(c)

1-[(S)-2-[[Methoxy[2-phenyl-1-[[(phenylmethoxy)carbonyl]amino]ethyl]phosphinyl]oxy]-1-oxopropyl]-L-proline, methyl ester The L-proline product from part (b) is dissolved in ethyl acetate (25 ml.) and treated with diazomethane in ether. A few drops of acetic acid are added to destroy excess diazomethane. The reaction mixture is concentrated to give 1.74 g. of a clear oil. This oil is chromatographed on silica gel (LPS-1, 200 mg.) eluting with ethyl acetate to give 1.36 g. of 1-[(S)-2-[[methoxy-[2-phenyl-1-[[(phenylmethoxy)carbonyl]amino]ethyl]phosphinyl]oxy]-1-oxopropyl]-L-proline, methyl ester as a clear oil.

(d)

1-[(S)-2-[[(1-Amino-2-phenylethyl)methoxyphosphinyl]oxy]-1-oxopropyl]-L-proline, methyl ester The methyl ester product from part (c) (1.36 g., 2.6 mmole) is dissolved in methanol (30 ml.) and hydrogenated at atmospheric pressure with 20% palladium hydroxide on carbon catalyst (226 mg.). The solution is filtered through Celite and concentrated to give 720 mg. of 1-[(S)-2-[[(1-amino-2-phenylethyl)methoxyphosphinyl]oxy]-1-oxopropyl]-L-proline, methyl ester.

(e)

1-[(S)-2-[[[1-[[(S)-6-[[(Phenylmethoxy)carbonyl]amino]-2-[(cyclobutylcarbonyl)amino]-1-oxohexyl]amino]-2-phenylethyl]methoxyphosphinyl]oxy]-1-oxopropyl]-L-proline, methyl ester $N^2$-(Cyclobutylcarbonyl)-$N^6$-[(phenylmethoxy)carbonyl]-L-lysine (340 mg., 0.94 mmole) [prepared as set forth in Example 1 (g)] is dissolved in tetrahydrofuran (5 ml.), and the solution is cooled to 0° under argon. Triethylamine (0.32 ml., 0.23 g., 2.3 mmole) and trimethylacetyl chloride (0.13 ml., 0.12 g., 1 mmole) are added and the resulting white suspension is stirred for one hour at 0°. A solution of 1-[(S)-2-[[(1-amino-2-phenylethyl)methoxyphosphinyl]oxy]-1-oxopropyl]-L-proline, methyl ester (360 mg., 0.94 mmole) is added, and the mixture is warmed to room temperature and it is stirred for 72 hours. The reaction mixture is then partitioned between 5% potassium bisulfate and ethyl acetate. The ethyl acetate solution is washed with half-saturated bicarbonate and brine, dried over sodium sulfate, and concentrated to give 750 mg. of a clear oil. This oil is chromatographed on silica gel (LPS-1) eluting with acetone:hexane (9:1) to give 480 mg. of 1-[(S)-2-[[[1-[[(S)-6-[[(phenylmethoxy)carbonyl]amino]-2-[(cyclobutylcarbonyl)amino]-1-oxohexyl]amino]-2-phenylethyl]methoxyphosphinyl]oxy]-1-oxopropyl]-L-proline, methyl ester.

(f)

1-[(S)-2-[[[1-[[(S)-6-[[(Phenylmethoxy)carbonyl]amino]-2-[(cyclobutylcarbonyl)amino]-1-oxohexyl]amino]-2-phenylethyl]hydroxphosphinyl]oxy]-1-oxopropyl]-L-proline, methyl ester The methyl ester product from part (e) (480 mg., 0.6 mmole) is dissolved in acetone (6 ml.) in a pressure tube. Trimethylamine is bubbled in to saturate the solution. The tube is capped tightly and heated to 95° overnight. The solution is concentrated to an oil which is partitioned between ethyl acetate and 5% potassium bisulfate. The ethyl acetate layer is washed with brine, dried over sodium sulfate, and concentrated to give 432 mg.

of 1-[(S)-2-[[[1-[[(S)-6-[[(phenylmethoxy)carbonyl]amino]-2-[(cyclobutylcarbonyl)amino]-1-oxohexyl]amino]-2-phenylethyl]hydroxyphosphinyl]oxy]-1-oxopropyl]-L-proline, methyl ester as a clear glass.

(g)

1-[(S)-2-[[[1-[[(S)-6-[[(Phenylmehtoxy)-carbonyl]amino]-2-[(cyclobutylcarbonyl)amino]-1-oxohexyl]amino]-2-phenylethyl]hydroxyphosphinyl]oxy]-1-oxopropyl]-L-proline The methyl ester product from part (f) (432 mg., 0.59 mmole) is dissolved in dioxane (2 ml.) with 1N lithium hydroxide (1.2 ml.) and stirred overnight. The reaction mixture is concentrated and partitioned between ethyl acetate and dilute potassium bisulfate. The ethyl acetate layer is concentrated to give 310 mg. of 1-[(S)-2-[[[1-[[(S)-6-[[(phenylmethoxy)carbonyl]amino]-2-[(cyclobutylcarbonyl)amino]-1-oxohexyl]amino]-2-phenylethyl]hydroxyphosphinyl]oxy]-1-oxopropyl]-L-proline.

(h)

1-[(S)-2-[[[1-[[(S)-6-Amino-2-[(cyclobutylcarbonyl)amino]-1-oxohexyl]amino]-2-phenylethyl]-hydroxyphosphinyl]oxy]-1-oxopropyl]-L-proline The L-proline product from part (g) (310 mg., 0.45 mmole) is dissolved in methanol (50 ml.) and hydrogenated at atmospheric pressure with 20% palladium hydroxide on carbon catalyst (50 ml.) overnight. The solution is filtered through Celite, concentrated, redissolved in water, filtered through a polycarbonate membrane (Millipore), frozen, and lyophilized to give 210 mg. of white solid 1-[(S)-2-[[[1-[[(S)-6-amino-2-[(cyclobutylcarbonyl)amino]-1-oxohexyl]amino]-2-phenylethyl]hydroxyphosphinyl]oxy]-1-oxopropyl]-L-proline; forms glass, shrinks at 170°; $[\alpha]_D = -43.4°$ (c=1.0, methanol). TLC (silica gel; isopropanol:ammonia:water, 7:2:1) $R_f = 0.41$.

Anal. calc'd. for $C_{27}H_{41}N_4O_8P \cdot 1.85\ H_2O$: C, 52.82; H, 7.34; N, 9.13; P, 5.04. Found: C, 52.82; H, 7.06; N, 8.89; P, 5.0.

EXAMPLE 4

1-[(S)-2-[[[1-[[(S)-6-Amino-2[(cyclohexylcarbonyl)amino]-1-oxohexyl]amino]pentyl]hydroxyphosphinyl]oxy]-1-oxopropyl]-L-proline, (isomer A)

(a)

1-[(S)-2-[[Hydroxy[1-[[(phenylmethoxy)carbonyl]amino]pentyl]phosphinyl]oxy]-1-oxopropyl]-L-proline 1-[(S)-2-[[Hydroxy[1-[[(phenylmethoxy)carbonyl]amino]pentyl]phosphinyl]oxy]-1-oxopropyl]-L-proline, phenylmethyl ester (5.5 g., 9.8 mmole) [prepared as set forth in Example 1(e)] is dissolved in a mixture of 1N lithium hydroxide (20 ml.) and dioxane (20 ml.) and stirred overnight under argon. The reaction mixture is concentrated in vacuo, and the residue is partitioned between water and ether. The aqueous layer is washed thoroughly with ether and once with ethyl acetate. This ethyl acetate solution is washed with brine, dried over sodium sulfate, and concentrated to give to give 3.3 g. of 1-[(S)-2-[[hydroxy[1-[[(phenylmethoxy)carbonyl]amino]pentyl]phosphinyl]oxy]-1-oxopropyl]-L-proline as a clear oil.

(b)

1-[(S)-2-[[Methoxy[1-[[(phenylmethoxy)carbonyl]amino]pentyl]phosphinyl]oxy]-1-oxopropyl]-L-proline, methyl ester The diacid product from part (a) (3.3 g., 7 mmole) is dissolved in ethyl acetate (50 ml.) and treated with diazomethane (made from 7 g. of N-methyl-N'-nitro-N-nitrosoguanidine, 21 ml. of 40% potassium hydroxide, and 90 ml. of ether) until esterification is complete. The solution is concentrated and the product is chromatographed (silica gel, LPS-1) eluting with ethyl acetate. The product containing fractions are combined and concentrated to give 2.23 g. of 1-[(S)-2-[[methoxy[1-[[(phenylmethoxy)carbonyl]amino]pentyl]phosphinyl]oxy]-1-oxopropyl]-L-proline, methyl ester.

(c)

1-[(S)-2-[[[(1-Amino)pentyl]methoxyphosphinyl]oxy]-1-oxopropyl]-L-proline, methyl ester The methyl ester product form part (b) (1.02 g., 2.06 mmole) is dissolved in methanol (25 ml.) at room temperature under argon. The solution is hydrogenated at atmospheric pressure with 20% palladium hydroxide on carbon catalyst for 2.5 hours. The mixture is then filtered through Celite to remove the catalyst and the volatiles are evaporated to give 712 mg. of 1-[(S)-2-[[[(1-amino)pentyl]methoxyphosphinyl]oxy]-1-oxopropyl]-L-proline, methyl ester.

(d)

$N^2$-(Cyclohexylcarbonyl)-$N^6$-[(phenylmethoxy)carbonyl]-L-lysine $N^6$-[(Phenylmethoxy)carbonyl]-L-lysine (3.54 g., 12.65 mmole) is dissolved in acetonitrile (37 ml.) at room temperature under argon. Bis(trimethylsilyl)trifluoroacetamide (14 ml.) is added and the resulting mixture is stirred for 1.5 hours. The mixture is cooled to 0° and a solution of cyclohexane carboxylic acid chloride (1.7 ml., 12.65 mmole) in tetrahydrofuran is added dropwise over 15 minutes. The reaction mixture is warmed to room temperature and is stirred for 4 hours. The mixture is partitioned between ethyl acetate and water and the organic layer is dried over sodium sulfate. The volatiles are evaporated and the residue is crystallized from hexane and dried in vacuo to give 4.525 g. of $N^2$-(cyclohexylcarbonyl)-$N^6$-[(phenylmethoxy)carbonyl]-L-lysine.

(e)

1-[(S)-2-[[[1-[[(S)-6-[[(Phenylmethoxy)carbonyl]amino]-2-[(cyclohexylcarbonyl)amino]-1-oxohexyl]amino]pentyl]methoxyphosphinyl]oxy]-1-oxopropyl]-L-proline, methyl ester $N^2$-(Cyclohexylcarbonyl)-$N^6$-[(phenylmethoxy)carbonyl]-L-lysine (281 mg., 0.72 mmole) is dissolved in tetrahydrofuran (4 ml.) at room temperature under argon. The mixture is cooled to 0° and treated with triethylamine (0.25 ml., 1.76 mmole) and pivaloyl chloride (0.10 ml.). After one hour at 0°, the reaction mixture is treated with a solution of 1-[(S)-2-[[[(1-amino)pentyl]methoxyphosphinyl]oxy]-1-oxopropyl]-L-proline, methyl ester (335 mg., 0.72 mmole) in tetrahydrofuran (4 ml.) and warmed to room temperature. After stirring overnight, the reaction mixture is partitioned between ethyl acetate and 5% potassium bisulfate. The organic layer is washed with sodium bicarbonate and brine, dried over sodium sulfate, and filtered. Evaporation of the volatiles followed by purification of the residue by column chromatography (silica gel, LPS-1) eluting with 10% hexaneacetone gives 357 mg. of 1-[(S)-2-[[[1-[[(S)-6-[[(phenylmethoxy)carbonyl]amino]-2-[(cyclohexylcarbonyl)amino]-1-oxohexyl]amino]pentyl]methoxyphosphinyl]oxy]-1-oxopropyl]-L-proline, methyl ester.

(f) 1-[(S)-2-[[[1-[[(S)-6-[[(Phenylmethoxy)carbonyl]amino]-2-[(cyclohexylcarbonyl)amino]-1-oxohexyl]amino]pentyl]hydroxyphosphinyl]oxy]-1-oxopropyl]-L-proline, methyl ester Trimethylamine is bubbled into a solution of the methyl ester product from part (e) (357 mg., 0.41 mmole) in acetone (6 ml.) until the mixture becomes saturated (about 20 minutes). The reaction mixture is placed into a sealed tube, heated to 95°, and kept at that temperature for 6 hours. The mixture is allowed to cool to room temperature overnight. The mixture is then partitioned between ethyl acetate and 5% potassium bisulfate. The organic layer is washed with brine, dried over sodium sulfate, filtered, and the volatiles evaporated to give 347 mg. of 1-[(S)-2-[[[1-[[(S)-6-[[(phenylmethoxy)carbonyl]amino]-2-[(cyclohexylcarbonyl)amino]-1-oxohexyl]amino]pentyl]hydroxyphosphinyl]oxy]-1-oxopropyl]-L-proline, methyl ester.

(g) 1-[(S)-2-[[[1-[[(S)-6-[[(Phenylmethoxy)carbonyl]amino]-2-[(cyclohexylcarbonyl)amino]-1-oxohexyl]amino]pentyl]hydroxyphosphinyl]oxy]-1-oxopropyl]-L-proline 1N Lithium hydroxide (2 ml.) is added to a solution of the methyl ester product from part (f) (347 mg., 0.41 mmole) in dioxane (2 ml.) at room temperature under argon. The resulting mixture is stirred overnight, partitioned between ethyl acetate and 5% potassium bisulfate, dried over sodium sulfate, and filtered. The volatiles are evaporated to give 272 mg. of 1-[(S)-2-[[[1-[[(S)-6-[[(phenylmethoxy)carbonyl]amino]-2-[(cyclohexylcarbonyl)amino]-1-oxohexyl]amino]pentyl]hydroxyphosphinyl]oxy]-1-oxopropyl]-L-proline.

(h) 1-[(S)-2-[[[1-[[(S)-6-Amino-2-[(cyclohexylcarbonyl)amino]-1-oxohexyl]amino]pentyl]hydroxyphosphinyl]oxy]-1-oxopropyl]-L-proline, (isomer A)

The L-proline product from part (g) (272 mg., 0.32 mmole) is dissolved in methanol (7 ml.) at room temperature under argon. The solution is hydrogenated at room temperature and atmospheric pressure with 20% palladium hydroxide on carbon catalyst (50 mg.) for 2.5 hours. The mixture is filtered through Celite to remove catalyst and the crude material is purified by column chromatography on HP-20 eluting with a water-(1:1) acetonitrile/water gradient to give 80 mg. of 1-[(S)-2-[[[1-[[(S)-6-amino-2-[(cyclohexylcarbonyl)amino]-1-oxohexyl]amino]pentyl]hydroxyphosphinyl]oxy]-1-oxopropyl]-L-proline, (isomer A) as a solid; m.p. 162°–170° (dec.); $[\alpha]_D = -52.0°$ (c=0.4, water). TLC (silica gel; isopropanol:ammonia:water, 7:2:1) $R_f = 0.33$.

Anal. Calc'd. for $C_{26}H_{47}N_4O_8P \cdot 1.75\ H_2O$: C, 51.52; H, 8.40; N, 9.24; P, 5.11. Found: C, 51.52; H, 8.15; N, 9.25; P, 5.10.

EXAMPLE 5

1-[(S)-2-[[[1-[[(S)-6-Amino-2-[(cyclohexylcarbonyl)amino]-1-oxohexyl]amino]pentyl]hydroxyphosphinyl]oxy]-1-oxopropyl]-L-proline, (isomer B)

The column chromatography of Example 4 (h) gives 53 mg. of 1-[(S)-2-[[[1-[[(S)-6-amino-2-[(cyclohexylcarbonyl)amino]-1-oxohexyl]amino]pentyl]hydroxyphosphinyl]oxy]-1-oxopropyl]-L-proline, (isomer B) as a solid; m.p. 165°–170° (dec.); $[\alpha]_D = -38.3°$ (c=0.35, water). TLC (silica gel; isopropanol:ammonia:water, 7:2:1) $R_f = 0.29$.

Anal. calc'd. for $C_{26}H_{47}N_4O_8P \cdot 1.7\ H_2O$: C, 51.59; H, 8.39; N, 9.26; P, 5.12. Found: C, 51.59; H, 8.05; N, 9.24; P, 5.30.

EXAMPLE 6

1-[(S)-2-[[[1-[[2-[(Cyclobutylcarbonyl)amino]-1-oxopropyl]amino]pentyl]hydroxyphosphinyl]oxy]-1-oxopropyl]-L-proline, dilithium salt (a) N-(Cyclobutylcarbonyl)-L-alanine, methyl ester L-Alanine, methyl ester, hydrochloride (1.77 g., 12.65 mmole) is suspended in dichloromethane (30 ml.) at room temperature under argon. The mixture is cooled to 0°. Triethylamine (3.53 ml., 25.3 mmole) is added, followed by the dropwise addition of cyclobutane carboxylic acid chloride (1.50 g., 12.65 mmole). The mixture is diluted with dichloromethane and washed with 5% potassium bisulfate, saturated aqueous sodium bicarbonate, and brine. The organic layer is dried over sodium sulfate, filtered, and the volatiles are evaporated to give 2.14 g. of N-(cyclobutylcarbonyl)-L-alanine, methyl ester.

(b) N-(Cyclobutylcarbonyl)-L-alanine

1N Lithium hydroxide (23.1 ml., 23.1 mmole) is added to a solution of N-(cyclobutylcarbonyl)-L-alanine, methyl ester (2.13 g., 11.55 mmole) in dioxane (90 ml.) at room temperature under argon. After standing for 2.5 hours, the dioxane is evaporated and the resulting mixture is partitioned between ethyl acetate and 5% potassium bisulfate. The organic layer is dried over sodium sulfate and filtered. The volatiles are evaporated to yield 1.53 g. of N-(cyclobutylcarbonyl)-L-alanine.

(c) 1-[(S)-2-[[[1-[[2-[(Cyclobutylcarbonyl)amino]-1-oxopropyl]amino]pentyl]methoxyphosphinyl]oxy]-1-oxopropyl]-L-proline, methyl ester Following the procedure of Example 4 part (e), 1-[(S)-2-[[[(1-amino)pentyl]methoxyphosphinyl]oxy]-1-oxopropyl]-L-proline, methyl ester (355 mg., 0.72 mmole), N-(cyclobutylcarbonyl)-L-alanine (123 mg., 0.72 mmole), triethylamine (0.25 ml., 1.76 mmole) and pivaloyl chloride (0.10 ml.) are reacted in tetrahydrofuran (8 ml.) to give 171 mg. of 1-[(S)-2-[[[1-[[2-[(cyclobutylcarbonyl)amino]-1-oxopropyl]amino]pentyl]methoxyphosphinyl]oxy]-1-oxopropyl]-L-proline, methyl ester.

(d) 1-[(S)-2-[[[1-[[2-[(Cyclobutylcarbonyl)amino]-1-oxopropyl]amino]pentyl]hydroxyphosphinyl]oxy]-1-oxopropyl]-L-proline, methyl ester The methyl ester product from part (c) (171 mg., 0.26 mmole) in acetone (6 ml.) is treated with trimethylamine according to the procedure of Example 4 part (f) to give 162 mg. of 1-[(S)-2-[[[1-[[2-[(cyclobutylcarbonyl)amino]-1-oxopropyl]amino]pentyl]hydroxyphosphinyl]oxy]-1-oxopropyl]-L-proline, methyl ester.

(e)

1-[(S)-2-[[[1-[[2-[(Cyclobutylcarbonyl)amino]-1-oxopropyl]amino]pentyl]hydroxyphosphinyl]oxy]-1-oxopropyl]-L-proline, dilithium salt 1N Lithium hydroxide (2 ml., 2.0 mmole) is added to a solution of the methyl ester product from part (d) (161 mg., 0.26 mmole) in dioxane (2 ml.) at room temperature under argon. The resulting mixture is stirred overnight. Evaporation of the volatiles followed by column chromatography (HP-20) eluting with water-1:1 acetonitrile/water gradient gives upon lyophilization 80 mg. of 1-[(S)-2-[[[1-[[2-[(cyclobutylcarbonyl)amino]-1-oxopropyl]amino]pentyl]hydroxyphosphinyl]oxy]-1-oxopropyl]-L-proline, dilithium salt as a solid; m.p. 160°–170° (dec.); $[\alpha]_D = -49.7°$ (c=0.33, water). TLC (silica gel; isopropanol:ammonia:water, 7:2:1) $R_f=0.51$.

Anal calc'd. for: $C_{21}H_{34}N_3O_8P \cdot 2$ Li$\cdot 1.79$ $H_2O$: C, 47.30; H, 7.10; N, 7.88; P, 5.80. Found: C, 47.30; H, 6.94; N, 7.75; P, 5.70.

EXAMPLE 7

1-[(S)-2-[[[1-[[(S)-2-[(Cyclobutylcarbonyl)amino]-1-oxohexyl]amino]pentyl]hydroxyphosphinyl]oxy]-1-oxopropyl]-L-proline, dilithium salt (a) N-(Cyclobutylcarbonyl)-L-norleucine, methyl ester L-Norleucine, methyl ester, hydrochloride (2.3 g., 12.65 mmole) is suspended in dichloromethane (30 ml.) at room temperature under argon. The mixture is cooled to 0°. Triethylamine (3.53 ml., 25.3 mmole) is added, followed by the dropwise addition of cyclobutane carboxylic acid chloride (1.5 g., 12.65 mmole). The mixture is diluted with dichloromethane and washed with 5% potassium bisulfate, saturated aqueous sodium bicarbonate, and brine. The organic layer is dried over sodium sulfate, filtered, and the volatiles are evaporated to give 2.53 g. of N-(cyclobutylcarbonyl)-L-norleucine, methyl ester.

(b) N-(Cyclobutylcarbonyl)-L-norleucine

A solution of N-(cyclobutylcarbonyl)-L-norleucine, methyl ester (2.53 g., 11.15 mmole) in dioxane (85 ml.) is treated with 1N lithium hydroxide (22.3 ml., 22.3 mmole) at room temperature under argon. After stirring for 2.5 hours, the dioxane is evaporated, and the resulting residue is partitioned between 5% potassium bisulfate and ethyl acetate. The organic layer is dried over sodium sulfate, filtered and the volatiles are evaporated to give 2.75 g. of N-(cyclobutylcarbonyl)-L-norleucine.

(c)

1-[(S)-2-[[[1-[[2-[(Cyclobutylcarbonyl)amino]-1-oxohexyl]amino]pentyl]methoxyphosphinyl]oxy]-1-oxopropyl]-L-proline, methyl ester Following the procedure of Example 4 part (e), 1-[(S)-2-[[[(1-amino)pentyl]methoxyphosphinyl]oxy]-1-oxopropyl]-L-proline, methyl ester (372 mg., 0.75 mmole), N-(cyclobutylcarbonyl)-L-norleucine (160 mg., 0.75 mmole), triethylamine (0.26 ml., 1.83 mmole), and pivaloyl chloride (0.11 ml.) are reacted in tetrahydrofuran (8 ml.) to give 250 mg. of 1-[(S)-2-[[[1-[[2-[(cyclobutylcarbonyl)amino]-1-oxohexyl]amino]pentyl]methoxyphosphinyl]oxy]-1-oxopropyl]-L-proline, methyl ester.

(d)

1-[(S)-2-[[[1-[[2-[(Cyclobutylcarbonyl)amino]-1-oxohexyl]amino]pentyl]hydroxyphosphinyl]oxy]-1-oxopropyl]-L-proline, methyl ester The methyl ester product from part (c) (250 mg., 0.36 mmole) in acetone (6 ml.) is treated with trimethylamine according to the procedure of Example 4 part (f) to give 230 mg. of 1-[(S)-2-[[[1-[[2-[(cyclobutylcarbonyl)amino]-1-oxohexyl]amino]pentyl]hydroxyphosphinyl]oxy]-1-oxopropyl]-L-proline, methyl ester.

(e)

1-[(S)-2-[[[1-[[(S)-2-[(Cyclobutylcarbonyl)amino]-1-oxohexyl]amino]pentyl]hydroxyphosphinyl]oxy]-1-oxopropyl]-L-proline, dilithium salt A solution of the methyl ester product from part (d) (230 mg., 0.34 mmole) in dioxane (3 ml.) is treated with 1N lithium hydroxide (3 ml., 3.0 mmole). The resulting mixture is stirred at room temperature overnight. The dioxane is evaporated and the resulting crude material is purified by column chromatography (HP-20) eluting with water-(1:1) acetonitrile/water gradient to yield upon lyophilization 144 mg. of 1-[(S)-2-[[[1-[[(S)-2-[(cyclobutylcarbonyl)amino]-1-oxohexyl]amino]pentyl]hydroxyphosphinyl]oxy]-1-oxopropyl]-L-proline, dilithium salt as a solid; m.p. 158°–168° (dec.); $[\alpha]_D = -51.3°$ (c=0.47, water). TLC (silica gel; isopropanol:ammonia:water, 7:2:1) $R_f=0.61$.

Anal. calc'd. for $C_{24}H_{40}N_3O_8P \cdot 2Li \cdot 2.6$ $H_2O$: C, 48.84; H, 7.72; N, 7.12; P, 5.2. Found: C, 48.84; H, 7.37; N, 6.73; P, 5.1.

EXAMPLE 8

1-[(S)-6-Amino-2-[[[1-[[(S)-6-amino-2-[(cyclobutylcarbonyl)amino]-1-oxohexyl]amino]pentyl]hydroxyphosphinyl]oxy]-1-oxohexyl]-L-proline (a)

(S)-2-Hydroxy-6-[[(phenylmethoxy)carbonyl]amino]hexanoic acid

L-lysine, monohydrochloride (130 g.) is dissolved in 2N lithium hydroxide (360 ml.) solution in a 2-liter, 3-necked, round bottom flask, equipped with an overhead stirrer, addition funnel and thermometer. Benzaldehyde (76.4 ml.) is added dropwise to this vigorously stirring solution at a temperature of about 5°. The reaction mixture turns cloudy at first and then becomes a thick mass of white precipitate. The rest of the benzaldehyde is added along with toluene (300 ml.) to improve the difficult stirring. The reaction mixture is stirred at about 5° for three hours. The mixture is filtered in a coarse sintered glass funnel. The solid is washed with ice cold water (50 ml.), ice cold ethanol (2×115 ml.), and then extensively with anhydrous ether. The product is dried in vacuo over 16 hours to give (S)-2-amino-6-[(benzylidene)amino]hexanoic acid as a white powder; m.p. 196°–200°.

This hexanoic acid (50 g., 0.2136 mole) is dissolved in water (350 ml.) and concentrated sulfuric acid (30 ml.) in a 1-liter, 3-necked, round bottom flask, equipped with a thermometer, overhead stirrer, addition funnel, and a condenser. This mixture is heated at 80° and a sodium nitrite solution (44 g. in 150 ml. of water) is added dropwise over a period of 4 hours. The reaction is stirred at 80° for sixteen hours and then cooled to room temperature. The reaction mixture is washed twice with ethyl acetate (200 ml.) and the pH is adjusted to 10 to 11 by the addition of 40% sodium hydroxide solution at 0°. [(Phenylmethoxy)carbonyl]chloride (33.4 ml.) is added portionwise and the reaction is kept at pH 10 for about 1.5 to 2 hours by adding sodium hydroxide solution. The reaction mixture is washed twice with ethyl acetate (200 ml.), the aqueous layer is acidified with concentrated hydrochloric acid until the pH is from about 1 to 2, and then it is extracted three times with ethyl acetate (200 ml.). The organic layers are combined, dried (MgSO$_4$), filtered, and evaporated to remove the solvent. The residue is crystallized with ethyl acetate/hexane (approximately 1:1) to give 32.5 g. of product. Recrystallization of the mother liquor yields another 1.96 g. of product for a total of 35.46 g. of (S)-2-hydroxy-6-[[(phenylmethoxy)carbonyl]amino]hexanoic acid; m.p. 79°–81°; $[\alpha]_D = +3.9°$, $[\alpha]_{365} = +23.7$ (c=1, chloroform). TLC (silica gel; methylene chloride:methanol:acetic acid, 17:1.5:1.5) $R_f = 0.53$.

Anal. calc'd. for $C_{14}H_{19}NO_5$: C, 59.77; H, 6.80; N, 4.97. Found: C, 59.71; H, 6.75; N, 5.02.

(b) (S)-2-Hydroxy-6-[(trifluoroacetyl)amino]hexanoic acid (S)-2-Hydroxy-6-[[(phenylmethoxy)carbonyl]amino]hexanoic acid (20 g., 72.2 mmole) is dissolved in methanol (100 ml.) in a Parr bottle. Water (50 ml.) is added gradually. The solution is degassed by bubbling argon through it and it is then hydrogenated on a Parr Shaker in the presence of 20% palladium hydroxide on carbon catalyst (1.5 g.). After the reaction is completed, the catalyst is filtered off and the solution is concentrated in vacuo to give 10.62 g. of beige solid (S)-(6-amino-2-hydroxy)hexanoic acid.

This (S)-(6-amino-2-hydroxy)hexanoic acid (5 g., 34 mmole) is mixed with methyltrifluoroacetate (17.1 ml.) at room temperature under argon. The mixture is treated with 1,1,3,3-tetramethyl guanidine and becomes warm. It is cooled back to room temperature with an ice bath and then stirred at room temperature for about 60 hours.

Water (25 ml.) is added and the solution is saturated with salt and acidified to pH of 1. The product is extracted into ethyl acetate and then concentrated to an oil. This oil is dissolved in water and the aqueous solution is washed with methylene chloride to remove nonpolar impurities. The aqueous solution is then concentrated to an oil, dissolved in ethyl acetate, and washed with 1N hydrochloric acid to remove residual tetramethyl guanidine. Concentration of the ethyl acetate solution gives 7 g. of (S)-2-hydroxy-6-[(trifluoroacetyl)amino]hexanoic acid. TLC (silica gel; isopropanol:ammonia:water, 7:2:1) $R_f = 0.64$.

Anal. calc'd. for $C_8H_{12}F_3NO_4$: C, 39.51; H, 4.98; N, 5.76; F, 23.44. Found: C, 38.17; H, 4.71; N, 5.32; F, 22.67.

(c) (S)-1-[2-Hydroxy-1-oxo-6-[(trifluoroacetyl)amino]hexyl]-L-proline, ethyl ester (S)-2-Hydroxy-6-[(trifluoroacetyl)amino]hexanoic acid (1.36 g., 5.58 mmole) and L-proline, ethyl ester, monohydrochloride (1 g., 5.58 mmole) are suspended together in tetrahydrofuran (10 ml.). The mixture is cooled to 0°, and triethylamine (0.93 ml., 675 mg., 6.68 mmole), 1-hydroxybenzotriazole hydrate (800 mg., 5.92 mmole) and dicyclohexylcarbodiimide (1.6 g., 7.76 mmole) are added. The reaction is stirred for 3 hours at 0° and then 2 hours at room temperature. It is then filtered and partitioned between ethyl acetate and 5% potassium bisulfate. The ethyl acetate layer is washed with bicarbonate and brine, and dried over sodium sulfate. It is then concentrated to an oil which is chromatographed (silica gel, LPS-1) eluting with ethyl acetate: hexane (2:1). The product containing fractions are combined to give 1.35 g. of (S)-1-[2-hydroxy-1-oxo-6-[(trifluoroacetyl)amino]hexyl]-L-proline, ethyl ester.

(d) 1-[(S)-6-[(Trifluoroacetyl)amino]-2-[[[1-[[(phenylmethoxy)carbonyl]amino]pentyl]hydroxyphosphinyl]oxy]-1-oxohexyl]-L-proline, ethyl ester (S)-1-[2-Hydroxy-1-oxo-6-[(trifluoroacetyl)amino]hexyl]-L-proline, ethyl ester (1.35 g., 3.7 mmole) and [1-[[(phenylmethoxy)carbonyl]amino]pentyl]phosphinic acid (1.16 g., 4.07 mmole) [prepared as set forth in Example 1(c)] are suspended in dichloromethane (10 ml.) under argon. Dicyclohexylcarbodiimide (991 mg., 4.81 mmole) and dimethylaminopyridine (50 mg.) are added, and the reaction mixture is stirred for 2 hours at room temperature. It is filtered and then partitioned between ethyl acetate and 5% potassium bisulfate. The ethyl acetate layer is washed with saturated bicarbonate and brine. It is then concentrated in vacuo. The resulting oil is dissolved in dioxane (10 ml.) and a solution of sodium periodate (980 mg., 4.6 mmole) in water (10 ml.) is added and the mixture is stirred overnight. It is then partitioned between ethyl acetate and 5% potassium bisulfate. The ethyl acetate layer is washed with dilute bisulfite to decolorize, then with brine. It is dried over sodium sulfate and concentrated to give 2.02 g. of 1-[(S)-6-[(trifluoroacetyl)amino]-2-[[[1-[[(phenylmethoxy)carbonyl]amino]pentyl]hydroxyphosphinyl]oxy]-1-oxohexyl]-L-proline, ethyl ester as a yellow oil.

(e) 1-[(S)-6-[(Trifluoroacetyl)amino]-2-[[[1-[[(phenylmethoxy)carbonyl]amino]pentyl]methoxyphosphinyl]oxy]-1-oxohexyl]-L-proline, ethyl ester The ethyl ester product from part (d) (2.02 g., 2.97 mmole) is dissolved in ethyl acetate (50 ml.) and treated with diazomethane (prepared from 2 g. of N-methyl-N'-nitro-N-nitrosoguanidine, 6 ml. of 40% potassium hydroxide in 25 ml. of ether). The solution is concentrated in vacuo and chromatographed (silica gel, LPS-1) eluting with ethyl acetate. The product containing fractions are combined to give 1.75 g. of 1-[(S)-6-[(trifluoroacetyl)amino]-2-[[[1-[[(phenylmethoxy)carbonyl]amino]pentyl]methoxyphosphinyl]oxy]-1-oxohexyl]-L-proline, ethyl ester as a clear oil.

(f) 1-[(S)-6-[(Trifluoroacetyl)amino]-2-[[[(1-amino)pentyl]methoxyphosphinyl]oxy]-1-oxohexyl]-L-proline, ethyl ester The ethyl ester product from part (e) (1.75 g., 2.63 mmole) is dissolved in methanol (75 ml.) at room temperature under argon. The solution is hydrogenated with 20% palladium hydroxide on carbon catalyst (300 mg.) at room temperature and atmospheric pressure for 3 hours. The reaction is filtered through Celite to remove the catalyst, and the volatiles are evaporated to give 1.7 g. of 1-(S)-6-[(Trifluoroacetyl)amino]-2-[[[(1-amino)pentyl]methoxyphosphinyl]oxy]-1-oxohexyl]-L-proline, ethyl ester.

(g)
1-[(S)-6-[(Trifluoroacetyl)amino]-2-[[[1-[[(S)-6-[[(phenylmethoxy)carbonyl]amino]-2-[(cyclobutylcarbonyl)amino]-1-oxohexyl]amino]pentyl]methoxyphosphinyl]oxy]-1-oxohexyl]-L-proline, ethyl ester Following the procedure of Example 4 part (e), 1-[(S)-6-[(trifluoroacetyl)amino]-2-[[[(1-amino)pentyl]methoxyphosphinyl]oxy]-1-oxohexyl]-L-proline, ethyl ester (1.7 g., 2.63 mmole), $N^2$-(cyclobutylcarbonyl)-$N^6$-[(phenylmethoxy)carbonyl]-L-lysine (952 mg., 2.63 mmole) [prepared as set forth in Example 1(g)], triethylamine (0.91 ml., 6.44 mmole), and pivaloyl chloride (0.37 ml.) are reacted in tetrahydrofuran (30 ml.) to give 1.03 g. of 1-[(S)-6-[(trifluoroacetyl)amino]-2-[[[1-[[(S)-6-[[(phenylmethoxy)carbonyl]amino]-2-[(cyclobutylcarbonyl)amino]-1-oxohexyl]amino]pentyl]methoxyphosphinyl]oxy]-1-oxohexyl]-L-proline, ethyl ester.

(h)
1-[(S)-6-[(Trifluoroacetyl)amino]-2-[[[1-[[(S)-6-[[(phenylmethoxy)carbonyl]amino]-2-[(cyclobutylcarbonyl)amino]-1-oxohexyl]amino]pentyl]hydroxyphosphinyl]oxy]-1-oxohexyl]-L-proline, ethyl ester The ethyl ester product from part (g) (1.03 g., 1.17 mmole) in acetone (6 ml.) is treated with trimethylamine according to the procedure of Example 4 part (f) to give 1.17 g. of 1-[(S)-6-[(trifluoroacetyl)amino]-2-[[[1-[[(S)-6-[[(phenylmethoxy)carbonyl]amino]-2-[(cyclobutylcarbonyl)amino]-1-oxohexyl]amino]pentyl]hydroxyphosphinyl]oxy]-1-oxohexyl]-L-proline, ethyl ester.

(i)
1-[(S)-6-Amino-2-[[[1-[[(S)-6-[[(phenylmethoxy)carbonyl]amino]-2-[(cyclobutylcarbonyl)amino]-1-oxohexyl]amino]pentyl]hydroxyphosphinyl]oxy]-1-oxohexyl]-L-proline A solution of the ethyl ester product from part (h) (1.17 g., 1.17 mmole) in dioxane (10 ml.) is treated with 1N lithium hydroxide (10 ml.) at room temperature under argon. The resulting mixture is stirred at room temperature overnight. The mixture is partitioned between ethyl acetate and 5% potassium bisulfate, dried over sodium sulfate, and filtered. The volatiles are evaporated to give 1.0 g. of 1-[(S)-6-amino-2-[[[1-[[(S)-6-[[(phenylmethoxy)carbonyl]amino]-2-[(cyclobutylcarbonyl)amino]-1-oxohexyl]amino]pentyl]hydroxyphosphinyl]oxy]-1-oxohexyl]-L-proline.

(j)
1-[(S)-6-Amino-2-[[[1-[[(S)-6-amino-2-[(cyclobutylcarbonyl)amino]-1-oxohexyl]amino]pentyl]hydroxyphosphinyl]oxy]-1-oxohexyl]-L-proline The L-proline product from part (i) (1.17 g., 1.17 mmole) is dissolved in methanol (30 ml.) under argon. Hydrogenation of this solution with 20% palladium hydroxide on carbon catalyst (200 mg.) at room temperature is completed in 3 hours. The reaction mixture is filtered to remove the catalyst and purified by column chromatography (HP-20) eluting with water-1:1 acetonitrile/water gradient to give upon lyophilization 380 mg. of solid 1-[(S)-6-amino-2-[[[1-[[(S)-6-amino-2-[(cyclobutylcarbonyl)amino]-1-oxohexyl]amino]pentyl]hydroxyphosphinyl]oxy]-1-oxohexyl]-L-proline, m.p. 200°–205° (dec.); $[\alpha]_D = -30.5°$ (c=0.55, water). TLC (silica gel; isopropanol:ammonia:water, 4:2:1) $R_f$=0.36.

Anal. calc'd. for $C_{27}H_{50}N_5O_8P \cdot 4.08\ H_2O$: C, 47.88; H, 8.66; N, 10.34; P, 4.57. Found: C, 47.88; H, 8.54; N, 10.30; P, 4.90.

EXAMPLE 9
1-[(S)-2-[[Hydroxy[1-(L-lysylamino)pentyl]phosphinyl]oxy]-1-oxopropyl]-L-proline

(a)
1-[(S)-2-[[[1-[[(S)-6-[[(Phenylmethoxy)carbonyl]amino]-2-[[(phenylmethoxy)carbonyl]amino]-1-oxohexyl]amino]pentyl]methoxyphosphinyl]oxy]-1-oxopropyl]-L-proline, methyl ester Following the procedure of Example 4 part (e), 1-[(S)-2-[[(1-amino)pentyl]methoxyphosphinyl]oxy-1-oxopropyl]-L-proline, methyl ester (385 mg., 0.78 mmole), N,N'-di-[(phenylmethoxy)carbonyl]-L-lysine (323 mg., 0.78 mmole), triethylamine (0.27 ml., 1.91 mmole), and pivaloyl chloride (0.11 ml.) are reacted in tetrahydrofuran (4 ml.) to give 501 mg. of 1-[(S)-2-[[[1-[[(S)-6-[[(phenylmethoxy)carbonyl]amino]-2-[[(phenylmethoxy)carbonyl]amino]-1-oxohexyl]amino]pentyl]methoxyphosphinyl]oxy]-1-oxopropyl]-L-proline, methyl ester.

(b)
1-[(S)-2-[[[1-[[(S)-6-[[(Phenylmethoxy)carbonyl]amino]-2-[[(phenylmethoxy)carbonyl]amino]-1-oxohexyl]amino]pentyl]hydroxyphosphinyl]oxy]-1-oxopropyl]-L-proline, methyl ester The methyl ester product from part (a) (501 mg., 0.56 mmole) in acetone (6 ml.) is treated with trimethylamine according to the procedure of Example 4 part (f) to give 558 mg. of 1-[(S)-2-[[[1-[[(S)-6-[[(phenylmethoxy)carbonyl]amino]-2-[[(phenylmethoxy)carbonyl]amino]-1-oxohexyl]amino]pentyl]hydroxyphosphinyl]oxy]-1-oxopropyl]-L-proline, methyl ester.

(c)
1-[(S)-2-[[[1-[[(S)-6-[(Phenylmethoxy)carbonyl]amino]-2-[[(phenylmethoxy)carbonyl]amino]-1-oxohexyl]amino]pentyl]hydroxyphosphinyl]oxy]-1-oxopropyl]-L-proline A solution of the methyl ester product from part (b) (558 mg., about 0.56 mmole) in dioxane (2 ml.) is treated with 1N lithium hydroxide (2 ml., 2 mmole) at room temperature under argon. The resulting mixture is stirred at room temperature overnight. The mixture is partitioned between ethyl acetate and 5% potassium bisulfate, dried over sodium sulfate, and filtered. The volatiles are evaporated to give 354 mg. of 1-[(S)-2-[[[1-[[(S)-6-[(phenylmethoxy)carbonyl]amino]-2-[[(phenylmethoxy)carbonyl]amino]-1-oxohexyl]amino]pentyl]hydroxyphosphinyl]oxy]-1-oxopropyl]-L-proline.

(d)
1-[(S)-2-[[Hydroxy[1-(L-lysylamino)pentyl]phosphinyl]oxy]-1-oxopropyl]-L-proline The L-proline product from part (c) (354 mg., 0.41 mmole) is dissolved in methanol (10 ml.) under argon. This solution is hydrogenated at room temperature and atmospheric pressure using 20% palladium hydroxide on carbon catalyst (65 mg.) for 3 hours. The mixture is filtered through Celite to remove catalyst and the crude material is purified by column chromatography (HP-20) eluting with a water-(1:1) acetonitrile/water gradient to give upon lyophilization 80 mg. of 1-[(S)-2[[hydroxy[1-(L-lysylamino)pentyl]- phosphinyl]oxy]-1-oxopropyl]-L-proline as a solid; m.p. 192°–197° (dec.); [α]$_D$= −24.1°, (c=0.41, water). TLC (silica gel; isopropanol:ammonia:water, 7:2:1) R$_f$=0.28.

Anal. calc'd. for C$_{19}$H$_{37}$N$_4$O$_7$P·2.74 H$_2$O: C, 44.41; H, 8.33; N, 10.90; P, 6.03. Found: C, 44.41; H, 8.28; N, 10.96; P, 5.90.

EXAMPLE 10

1-[(S)-2-[[[1-[[(S)-6-Amino-2-[(cyclobutylcarbonyl)amino]-1-oxohexyl]amino]pentyl]hydroxyphosphinyl]oxy]-1-oxopropyl]-L-proline (isomer B)

(a)

[1-[[(Phenylmethoxy)carbonyl)amino]pentyl]phosphinic acid (isomer B)

[1-[[(Phenylmethoxy)carbonyl]amino]pentyl]phosphinic acid, hydrochloride (24 g., 84 mmole) is dissolved in boiling ethanol (120 ml.) and filtered. A solution of (R)-(+)-α-methylbenzylamine (11.3 ml., 88 mmole, 10.6 g.) in ethanol (15 ml.) is added. The solution is removed from the heat, seeded, cooled to room temperature and refrigerated overnight. The precipitated needles are collected on a frit and air dried to give 13.24 g. of resolved product. Recrystallization from ethanol (3 times) gives 8.5 g. of solid; [α]$_D$= −30.0° (c=1.0, methanol). This solid (8.5 g., 20.9 mmole) is partitioned between ethyl acetate and 1N HCl. The ethyl acetate layer is dried over sodium sulfate and concentrated in vacuo to give 5.46 g. of white solid [1-[[(phenylmethoxy)carbonyl]amino]pentyl]phosphinic acid (isomer B); [α]$_D$= −51.5° (c=1.0, methanol).

(b)

1-[(S)-2-[[Hydroxy[1-[[(phenylmethoxy)carbonyl]amino]pentyl]phosphinyl]oxy]-1-oxopropyl]-L-proline, ethyl ester

[1-[[(Phenylmethoxy)carbonyl]amino]pentyl]phosphinic acid (isomer B) (4.021 g., 14.11 mmole) and 1-[(S)-2-hydroxy-1-oxopropyl]-L-proline, ethyl ester (2.76 g., 12.83 mmole) are suspended in methylene chloride (40 ml.) at room temperature under argon. Dicyclohexylcarbodiimide (3.44 g.) and dimethylaminopyridine (174 mg.) are added and the resulting mixture is stirred for 2.5 hours. The mixture is partitioned between ethyl acetate and 5% potassium bisulfate, and the organic layer is extracted once with aqueous sodium bicarbonate and once with brine. The organic layer is concentrated in vacuo and the residue is dissolved in p-dioxane (40 ml.). A solution of sodium metaperiodate (3.4 g., 15.94 mmole) in water (40 ml.) is added and the resulting mixture is stirred overnight. The mixture is partitioned between ethyl acetate and 5% potassium bisulfate and the organic layer is washed with aqueous sodium bicarbonate and brine. The organic layer is dried over sodium sulfate and filtered, and the volatiles are evaporated to yield 6.23 g. of 1-[(S)-2-[[hydroxy[1-[[(phenylmethoxy)carbonyl]amino]pentyl]phosphinyl]oxy]-1-oxopropyl]-L-proline, ethyl ester (isomer B). TLC (silica gel; methylene chloride:acetic acid:methanol, 20:1:1) R$_f$=0.24.

(c)

1-[(S)-2-[[Methoxy[1-[[(phenylmethoxy)carbonyl]amino]pentyl]phosphinyl]oxy]-1-oxopropyl]-L-proline, ethyl ester (isomer B)

The ethyl ester product from part (b) (6.23 g., 12.5 mmole) in ethyl acetate (150 ml.) is treated with diazomethane according to the procedure of Example 4, part (b). The crude residue is purified by column chromatography on silica gel (LPS-1) eluting with ethyl acetate to yield 4.86 g. of 1-[(S)-2-[[methoxy[1-[[(phenylmethoxy)carbonyl]amino]pentyl]phosphinyl]oxy]-1-oxopropyl]-L-proline, ethyl ester (isomer B). TLC (silica gel; methylene chloride:acetic acid:methanol, 20:1:1) R$_f$=0.56.

(d)

1-[(S)-2-[[[(1-Amino)pentyl]methoxyphosphinyl]oxy]-1-oxopropyl]-L-proline, ethyl ester (isomer B)

The ethyl ester product from part (c) (2.3 g., 4.49 mmole) is dissolved in methanol (60 ml.) under argon. The solution is hydrogenated at room temperature with 20% palladium hydroxide on carbon catalyst for 2.5 hours. The mixture is filtered through Celite to remove the catalyst and the volatiles are evaporated to give 1.69 g. of 1-[(S)-2-[[[(1-amino)pentyl]methoxyphosphinyl]oxy]-1-oxopropyl]-L-proline, ethyl ester (isomer B). TLC (silica gel; hexane:acetone, 1:1) R$_f$=0.13.

(e)

1-[(S)-2-[[[1-[[(S)-6-[[(Phenylmethoxy)carbonyl]amino]-2-[(cyclobutylcarbonyl)amino]-1-oxohexyl]amino]pentyl]methoxyphosphinyl]oxy]-1-oxopropyl]-L-proline, ethyl ester (isomer B)

N$^2$-(Cylobutylcarbonyl)-N$^6$-[(phenylmethoxy)carbonyl]-L-lysine (1.62 g., 4.47 mmole) is dissolved in tetrahydrofuran (28 ml.) at room temperature under argon. The mixture is cooled to 0° and treated with triethylamine (1.55 ml., 10.95 mmole) and pivaloyl chloride (0.63 ml.). After one hour at 0°, the reaction mixture is treated with a solution of 1-[(S)-2-[[[(1-amino)pentyl]methoxyphosphinyl]oxy]-1-oxopropyl]-L-proline, ethyl ester (isomer B) (1.69 g., 4.47 mmole) in tetrahydrofuran (25 ml.) according to the procedure of Example 4 part (e). The crude reaction mixture is purified by column chromatography (silica gel) eluting with 20% hexane/acetone to give 1.16 g. of 1-[(S)-2-[[[1-[[(S)-6-[[(phenylmethoxy)carbonyl]amino]-2-[(cyclobutylcarbonyl)amino]-1-oxohexyl]amino]pentyl]methoxyphosphinyl]oxy]-1-oxopropyl]-L-proline, ethyl ester (isomer B). TLC (silica gel; methylene chloride:acetic acid:methanol, 20:1:1) R$_f$=0.55.

(f)

1-[(S)-2-[[[1-[[(S)-6-[[(Phenylmethoxy)carbonyl]amino]-2-[(cyclobutylcarbonyl)amino]-1-oxohexyl]amino]pentyl]hydroxyphosphinyl]oxy]-1-oxopropyl]-L-proline, ethyl ester (isomer B)

Trimethylamine is bubbled into a solution of the ethyl ester product from part (e) (1.16 g., 1.61 mmole) in acetone (6 ml.) according to the procedure of Example 4 part (f) to give 1.02 g. of 1-[(S)-2-[[[1-[[(S)-6-[[(phenylmethoxy)carbonyl]amino]-2-[(cyclobutylcarbonyl)amino]-1-oxohexyl]amino]pentyl]hydroxyphosphinyl]oxy]-1-oxopropyl]-L-proline, ethyl ester (isomer B). TLC (silica gel; esopropanol:ammonia:water, 7:2:1) R$_f$=0.58.

(g)

1-[(S)-2-[[[1-[[(S)-6-[[(Phenylmethoxy)carbonyl]amino]-2-[(cyclobutylcarbonyl)amino]-1-oxohexyl]amino]pentyl]hydroxyphosphinyl]oxy]-1-oxopropyl]-L-proline (isomer B)

1N Lithium hydroxide (10 ml.) is added to a solution of the ethyl ester product from part (f) (1.02 g., 1.44 mmole) in p-dioxane (10 ml.) according to the procedure of Example 4 part (g) to give 880 mg. of 1-[(S)-2-[[[1-[[(S)-6-[[(phenylmethoxy)carbonyl]amino]-2-[(cyclobutylcarbonyl)amino]-1-oxohexyl]amino]pentyl]hydroxyphosphinyl]oxy]-1-oxopropyl]-L-proline (isomer B). TLC (silica gel; isopropanol:ammonia:water, 7:2:1) $R_f=0.65$.

(h)

1-[(S)-2-[[[1-[[(S)-6-Amino-2-[(cyclobutylcarbonyl)amino]-1-oxohexyl]amino]pentyl]hydroxyphosphinyl]oxy]-1-oxopropyl]-L-proline (Isomer B)

The L-proline product from part (g) (880 mg., 1.29 mmole) is dissolved in methanol (30 ml.) at room temperature under argon. The solution is hydrogenated at room temperature and atmospheric pressure with 20% palladium hydroxide on carbon catalyst (200 mg.) for 3 hours. The mixture is filtered through Celite to remove catalyst and the crude material is purified by column chromatography on HP-20 eluting with a water-(1:1) acetonitrile/water gradient to give upon lyophilization 370 mg. of 1-[(S)-2-[[[1-[[(S)-6-amino-2-[(cyclobutylcarbonyl)amino]-1-oxohexyl]amino]pentyl]hydroxyphosphinyl]oxy]-1-oxopropyl]-L-proline (isomer B); m.p. 140°-145° (dec.); $[\alpha]_D = -91.3°$ (c=0.4, water). TLC (silica gel; isopropanol:ammonia:water, 7:2:1) $R_f=0.21$.

Anal. calc'd. for $C_{24}H_{43}N_4O_8P\cdot 2\ H_2O$: C, 49.47; H, 8.39; N, 9.62; P, 5.32. Found: C, 49.26; H, 8.06; N, 9.41; P, 5.40.

EXAMPLE 11

1-[(S)-2-[[[1-[[N$^6$-Acetyl-N$^2$-(cyclobutylcarbonyl)-L-lysyl]amino]pentyl]hydroxyphosphinyl]oxy]-1-oxopropyl]-L-proline (isomer B)

The product from Example 10 (230 mg., 0.4 mmole) is dissolved in pyridine (0.48 ml., 6.0 mmole) at room temperature under argon. Acetic anhydride (0.49 ml., 5.2 mmole) is added, and the resulting mixture is stirred for 3.5 hours. The volatiles are evaporated and the residue is chased with toluene (3×25 ml.). The residue is purified by column chromatography (HP - 20) eluting with water-1:1 water/acetonitrile gradient to yield upon lyophilization 167 mg. of 1-[(S)-2-[[[1-[[N$^6$-acetyl-N$^2$-(cyclobutylcarbonyl)-L-lysyl]amino]pentyl]hydroxyphosphinyl]oxy]-1-oxopropyl]-L-proline (isomer B); m.p. 170°-175° (dec.); $[\alpha]_D = -90.2°$ (c=0.48, water). TLC (silica gel; isopropanol:ammonia:water, 7:2:1) $R_f=0.47$.

Anal. calc'd. for $C_{26}H_{45}N_4O_9P\cdot 1.72\ H_2O$: C, 50.40; H, 7.88; N, 9.04; P, 5.00. Found: C, 50.40; H, 7.80; N, 9.20; P, 5.01.

EXAMPLE 12

1-[(S)-2-[[[1-[[N$^6$-(Aminoiminomethyl)-N$^2$-(cyclobutylcarbonyl)-L-lysyl]amino]pentyl]hydroxyphosphinyl]oxy]-1-oxopropyl]-L-proline (isomer B), disodium salt Sodium bicarbonate (298 mg.) is added to a solution of the product from Example 10 (215 mg., 0.39 mmole) in water (2 ml.) at room temperature. 2-Methyl-2-thiopseudourea sulfate (165 mg., 0.59 mmole) is added, and the resulting mixture is stirred for 4 hours. The volatiles are evaporated, and the residue is purified by column chromatography (HP-20) eluting with water, 5% acetone/water, and 10% acetone/water to yield upon lyophilization 86 mg. of 1-[(S)-2-[[[1-[[N$^6$-(aminoiminomethyl)-N$^2$-(cyclobutylcarbonyl)-L-lysyl]amino]pentyl]hydroxyphosphinyl]oxy]-1-oxopropyl]-L-proline (isomer B), disodium salt; m.p. 200°-205° (dec.); $[\alpha]_D = -74.9°$ (c=0.35, water). TLC (silica gel; isopropanol:ammonia:water, 7:2:1) $R_f=0.39$.

Anal. calc'd. for $C_{25}H_{43}N_6O_8P\cdot 2Na\cdot 3.05\ H_2O$: C, 43.67; H, 7.20; N, 12.23; P, 4.50. Found: C, 43.51; H, 6.92; N, 12.20; P, 4.66.

EXAMPLE 13

1-[(S)-2-[[1-[[(S)-6-Amino-2-[(cyclopropylcarbonyl)amino]-1-oxohexyl]amino]pentyl]hydroxyphosphinyl]oxy]-1-oxopropyl]-L-proline (isomer B)

(a)

N$^2$-(Cyclopropylcarbonyl)-N$^6$-[(phenylmethoxy)carbonyl]-L-lysine

N$^6$-[(Phenylmethoxy)carbonyl]-L-lysine (3.54 g., 12.65 mmole) is dissolved in acetonitrile (37 ml.) at room temperature under argon. Bis(trimethylsilyl)trifluoroacetamide (14 ml.) is added and the resulting mixture is stirred for 1.5 hours. The mixture is cooled to 0° and a solution of cyclopropane carboxylic acid chloride (1.15 ml., 12.65 mmole) in tetrahydrofuran (7.5 ml.) is added dropwise according to the procedure of Example 4 part (d) to yield 3.8 g. of N$^2$-(cyclopropylcarbonyl)-N$^6$-[(phenylmethoxy)carbonyl]-L-lysine. TLC (silica gel; methylene chloride:acetic acid:methanol, 20:1:1) $R_f=0.45$.

(b)

1-[(S)-2-[[[1-[[(S)-6-[[(Phenylmethoxy)carbonyl]amino]-2-[(cyclopropylcarbonyl)amino]-1-oxohexyl]amino]pentyl]methoxyphosphinyl]oxy]-1-oxopropyl]-L-proline, ethyl ester, (isomer B)

N$^2$-(Cyclopropylcarbonyl)-N$^6$-[(phenylmethoxy)carbonyl]-L-lysine (588 mg., 1.69 mmole) is dissolved in tetrahydrofuran (9 ml.) at room temperature under argon. The mixture is cooled to 0° and treated with triethylamine (0.59 ml., 4.12 mmole) and pivaloyl chloride (0.25 ml.). After one hour at 0°, the reaction mixture is treated with a solution of 1-[(S)-2-[[[(1-amino)pentyl]methoxyphosphinyl]oxy]-1-oxopropyl]-L-proline, ethyl ester (isomer B) (840 mg., 1.69 mmole) in tetrahydrofuran (9 ml.) according to the procedure of Example 4 part (e) to give 870 mg. of 1-[(S)-2-[[[1-[[(S)-6-[[(phenylmethoxy)carbonyl]amino]-2-[(cyclopropylcarbonyl)amino]-1-oxohexyl]amino]pentyl]methoxyphosphinyl]oxy]-1-oxopropyl]-L-proline, ethyl ester (isomer B). TLC (silica gel; methylene chloride:methanol:acetic acid, 20:1:1) $R_f=0.49$.

(c)

1-[(S)-2-[[[1-[[(S)-6-[[(Phenylmethoxy)carbonyl]amino]-2-[(cyclopropylcarbonyl)amino]-1-oxohexyl]amino]pentyl]hydroxyphosphinyl]oxy]-1-oxopropyl]-L-proline, ethyl ester (isomer B)

Trimethylamine is bubbled into a solution of the diester product from part (b) (870 mg., 1.23 mmole) in acetone (5 ml.) according to the procedure of Example 4 part (f) to yield 800 mg. of 1-[(S)-2-[[[1-[[(S)-6-[[(phenylmethoxy)carbonyl]amino]-2-[(cyclopropylcarbonyl)amino]-1-oxohexyl]amino]pentyl]hydroxyphosphinyl]oxy]-1-oxopropyl]-L-proline, ethyl ester (isomer B). TLC (silica gel; isopropanol:ammonia:water, 7:2:1) $R_f=0.56$.

(d)
1-[(S)-2-[[[1-[[(S)-6-[[(Phenylmethoxy)carbonyl]amino]-2-[(cyclopropylcarbonyl)amino]-1-oxohexyl]amino]pentyl]hydroxyphosphinyl]oxy]-1-oxopropyl]-L-proline (isomer B)

1N Lithium hydroxide (10 ml.) is added to a solution of the ethyl ester product from part (c) (800 mg., 1.15 mmole) in p-dioxane (10 ml.) and the reaction mixture is worked up according to the procedure of Example 4 part (g) to yield 670 mg. of 1-[(S)-2-[[[1-[[(S)-6-[[(phenylmethoxy)carbonyl]amino]-2-[(cyclopropylcarbonyl)amino]-1-oxohexyl]amino]pentyl]hydroxyphosphinyl]oxy]-1-oxopropyl]-L-proline (isomer B). TLC (silica gel; isopropanol:ammonia:water, 7:2:1) $R_f=0.43$.

(e)
1-[(S)-2-[[[1-[[(S)-6-Amino-2-[(cyclopropylcarbonyl)amino]-1-oxohexyl]amino]pentyl]hydroxyphosphinyl]oxy]-1-oxopropyl]-L-proline (isomer B)

The product from part (d) (670 mg., 1.01 mmole) is dissolved in methanol (25 ml.) at room temperature under argon. The solution is hydrogenated with 20% palladium hydroxide on carbon catalyst (150 mg.) for 2.5 hours. The reaction mixture is filtered through Celite to remove the catalyst, and the volatiles are evaporated. Purification by column chromatography on HP-20 eluting with a water-1:1 acetonitrile/water gradient yields upon lyophilization 275 mg. of 1-[(S)-2-[[[1-[[(S)-6-amino-2-[(cyclopropylcarbonyl)amino]-1-oxohexyl]amino]pentyl]hydroxyphosphinyl]oxy]-1-oxopropyl]-L-proline (isomer B); 155°–165° (dec.); $[\alpha]_D=-92.1°$ (c=0.48, water). TLC (silica gel; isopropanol:ammonia:water, 7:2:1) $R_f=0.25$.

Anal. calc'd. for $C_{23}H_{41}N_4O_8P\cdot1.68\ H_2O$: C, 49.07; H, 7.95; N, 9.95; P, 5.50. Found: C, 49.07; H, 7.51; N, 9.82; P, 5.20.

EXAMPLE 14

1-[(S)-2-[[[1-[[(S)-6-Amino-2-[(cyclopentylcarbonyl)amino]-1-oxohexyl]amino]pentyl]hydroxyphosphinyl]oxy]-1-oxopropyl]-L-proline (isomer B)

(a)
$N^2$-(Cyclopentylcarbonyl)-$N^6$-[(phenylmethoxy)carbonyl]-L-lysine $N^6$-[(Phenylmethoxy)carbonyl]-L-lysine (3.54 g., 12.65 mmole) is dissolved in acetonitrile (37 ml.) at room temperature under argon. Bis(trimethylsilyl)trifluoroacetamide (14 ml.) is added and the resulting mixture is stirred for 2 hours. The mixture is cooled to 0° and a solution of cyclopentane carboxylic acid chloride (12.65 mmole) in tetrahydrofuran (8 ml.) is added. The mixture is allowed to warm to room temperature and is stirred overnight. The mixture is partitioned between ethyl acetate and water, the organic layer is dried over sodium sulfate, and the volatiles are evaporated. The residue is purified by column chromatography (LPS-1 silica) eluting with 10% methanol/methylene chloride to give the desired product contaminated with trifluoroacetamide. The product is partitioned between ether and saturated sodium bicarbonate, the aqueous layer is acidified to pH of 1 with concentrated HCl, and extracted (3×) with ethyl acetate. The organics are dried over sodium sulfate, filtered, and the volatiles are evaporated to give 1.2 g. of $N^2$-(cyclopentylcarbonyl)-$N^6$-[(phenylmethoxy)carbonyl]-L-lysine. TLC (silica gel; methylene chloride:methanol:acetic acid) $R_f=0.59$.

(b)
1-[(S)-2-[[[1-[[(S)-6-[[(Phenylmethoxy)carbonyl]amino]-2-[(cyclopentylcarbonyl)amino]-1-oxohexyl]amino]pentyl]methoxyphosphinyl]oxy]-1-oxopropyl]-L-proline, ethyl ester(isomer B)

$N^2$-(Cyclopentylcarbonyl)-$N^6$-[(phenylmethoxy)carbonyl]-L-lysine (827 mg., 2.20 mmole) is dissolved in tetrahydrofuran (12 ml.) at room temperature under argon. The mixture is cooled to 0° and treated with triethylamine (0.77 ml., 5.4 mmole) and pivaloyl chloride (0.33 ml.). After one hour at 0° the reaction mixture is treated with a solution of 1-[(S)-2-[[[(1-amino)pentyl]methoxyphosphinyl]oxy]-1-oxopropyl]-L-proline, ethyl ester (isomer B) (830 mg., 2.20 mmole) in tetrahydrofuran (12 ml.) according to the procedure of Example 4 part (e) to give 930 mg. of 1-[(S)-2-[[[1-[[(S)-6-[[(phenylmethoxy)carbonyl]amino]-2-[(cyclopentylcarbonyl)amino]-1-oxohexyl]amino]pentyl]methoxyphosphinyl]oxy]-1-oxopropyl]-L-proline, ethyl ester (isomer B). TLC (silica gel; methylene chloride:methanol:acetic acid, 20:1:1) $R_f=0.52$.

(c)
1-[(S)-2-[[[1-[[(S)-6-[[(Phenylmethoxy)carbonyl]amino]-2-[(cyclopentylcarbonyl)amino]-1-oxohexyl]amino]pentyl]hydroxyphosphinyl]oxy]-1-oxopropyl]-L-proline, ethyl ester (isomer B)

Trimethylamine is bubbled into a solution of the diester product from part (b) (930 mg., 1.26 mmole) in acetone (6 ml.) according to the procedure of Example 4 part (f) to yield 750 mg. of 1-[(S)-2-[[[1-[[(S)-6-[[(phenylmethoxy)carbonyl]amino]-2-[(cyclopentylcarbonyl)amino]-1-oxohexyl]amino]pentyl]hydroxyphosphinyl]oxy]-1-oxopropyl]-L-proline, ethyl ester (isomer B). TLC (silica gel; isopropanol:ammonia:water, 7:2:1) $R_f=0.58$.

(d)
1-[(S)-2-[[[1-[[(S)-6-[[(Phenylmethoxy)carbonyl]amino]-2-[(cyclopentylcarbonyl)amino]-1-oxohexyl]amino]pentyl]hydroxyphosphinyl]oxy]-1-oxopropyl]-L-proline (isomer B)

1N Lithium hydroxide (10 ml.) is added to a solution of the ethyl ester product from part (c) (750 mg., 1.04 mmole) in p-dioxane (10 ml.) and the reaction mixture is worked up according to the procedure of Example 4 part (g) to yield 620 mg. of 1-[(S)-2-[[[1-[[(S)-6-[[(phenylmethoxy)carbonyl]amino]-2-[(cyclopentylcarbonyl)amino]-1-oxohexyl]amino]pentyl]hydroxyphosphinyl]oxy]-1-oxopropyl]-L-proline (isomer B). TLC (silica gel; isopropanol:ammonia:water, 7:2:1) $R_f=0.50$.

(e)
1-[(S)-2-[[[1-[[(S)-6-Amino-2-[(cyclopentylcarbonyl)amino]-1-oxohexyl]amino]pentyl]hydroxyphosphinyl]oxy]-1-oxopropyl]-L-proline (isomer B)

The product from part (d) (615 mg., 0.89 mmole) is dissolved in methanol (25 ml.) at room temperature under argon. The solution is hydrogenated with 20% palladium hydroxide on carbon catalyst (150 mg.) for 2.5 hours. The reaction mixture is filtered through Celite to remove the catalyst, and the volatiles are evaporated. Purification by column chromatography on HP-20 eluting with a water -1:1 acetonitrile/water gradient yields upon lyophilization 250 mg. of 1-[(S)-2-[[[1-[[(S)-6-amino-2-[(cyclopentylcarbonyl)amino]-1-oxohexyl]amino]pentyl]hydroxyphosphinyl]oxy]-1- oxopropyl]-L-proline (isomer B); 160°–165° (dec.); [α]$_D$= −89.8° (c=0.40, water). TLC (silica gel isopropanol:ammonia:water, 7:2:1) R$_f$=0.29.

Anal. calc'd. for C$_{25}$H$_{45}$N$_4$O$_8$P·1.56 H$_2$O: C, 51.00; H, 8.24; N, 9.52; P, 5.26. Found: C, 51.00; H, 7.84; N, 9.49; P, 4.98.

EXAMPLE 15

1-[(S)-2-[[[1-[(N$^2$-Benzoyl-L-lysyl)amino]pentyl]hydroxyphosphinyl]oxy]-1-oxopropyl]-L-proline (isomer B)

(a)

N$^2$-Benzoyl-N$^6$-[(phenylmethoxy)carbonyl]-L-lysine

N$^6$-[(Phenylmethoxy)carbonyl]-L-lysine (3.54 g., 12.65 mmole) is dissolved in acetonitrile (37 ml.) at room temperature under argon. Bis(trimethylsilyl)trifluoroacetamide (14 ml.) is added and the resulting mixture is stirred for 1.5 hours. The mixture is cooled to 0° and a solution of benzoyl chloride (1.47 ml., 12.65 mmole) in tetrahydrofuran (8 ml.) is added according to the procedure of Example 4 part (d). The reaction mixture is partitioned between ethyl acetate and water, and the organic layer is dried over sodium sulfate and filtered. The volatiles are evaporated and the crude residue is purified by chromatography (LPS-1 silica) eluting with 10% methanol/methylene chloride to yield 4.73 g. of N$^2$-benzoyl-N$^6$-[(phenylmethoxy)carbonyl]-L-lysine. TLC (silica gel; methylene chloride:methanol:acetic acid, 20:1:1) R$_f$=0.50.

(b)

1-[(S)-2-[[[1-[[(S)-6-[[(Phenylmethoxy)carbonyl]amino]-2-[(benzoyl)amino]-1-oxohexyl]amino]pentyl]methoxyphosphinyl]oxy]-1-oxopropyl]-L-proline, ethyl ester (isomer B)

N$^2$-(Benzoyl)-N$^6$-[(phenylmethoxy)carbonyl]-L-lysine (438 mg., 1.14 mmole) is dissolved in tetrahydrofuran (6 ml.) at room temperature under argon. The mixture is cooled to 0° and treated with triethylamine (0.4 ml., 2.78 mmole) and pivaloyl chloride (0.17 ml.). After one hour at 0°, the reaction mixture is treated with a solution of 1-[(S)-2-[[[(1-amino)pentyl]methoxyphosphinyl]oxy]-1-oxopropyl]-L-proline, ethyl ester (isomer B) (430 mg., 1.14 mmole) in tetrahydrofuran (6 ml.) according to the procedure of Example 4 part (e) to give 480 mg. of 1-[(S)-2-[[[1-[[(S)-6-[[(phenylmethoxy)carbonyl]amino]-2-[(benzoyl)amino]-1-oxohexyl]amino]pentyl]methoxyphosphinyl]oxy]-1-oxopropyl]-L-proline, ethyl ester (isomer B). TLC (silica gel; methylene chloride:methanol:acetic acid, 20:1:1) R$_f$=0.66.

(c)

1-[(S)-2-[[[1-[[(S)-6-[[(Phenylmethoxy)carbonyl]amino]-2-[(benzoyl)amino]-1-oxohexyl]amino]pentyl]hydroxyphosphinyl]oxy]-1-oxopropyl]-L-proline, ethyl ester (isomer B)

Trimethylamine is bubbled into a solution of the diester product from part (b) (480 mg., 0.65 mmole) in acetone (6 ml.) according to the procedure of Example 4 part (f) to yield 430 mg. of 1-[(S)-2-[[[1-[[(S)-6-[[(phenylmethoxy)carbonyl]amino]-2-[(benzoyl)amino]-1-oxohexyl]amino]pentyl]hydroxyphosphinyl]oxy]-1-oxopropyl]-L-proline, ethyl ester (isomer B). TLC (silica gel; isopropanol:ammonia:water, 7:2:1) R$_f$=0.68.

(d)

1-[(S)-2-[[[1-[[(S)-6-[[(Phenylmethoxy)carbonyl]amino]-2-[(benzoyl)amino]-1oxohexyl]amino]pentyl]hydroxyphosphinyl]oxy]-1-oxopropyl]-L-proline (isomer B)

1N Lithium hydroxide (6 ml.) is added to a solution of the ethyl ester product from part (c) (430 mg., 0.59 mmole) in p-dioxane (6 ml.) and the reaction mixture is worked up according to the procedure of Example 4 part (g) to yield 360 mg. of 1-[(S)-2-[[[1-[[(S)-6-[[(phenylmethoxy)carbonyl]amino]-2-[(benzoyl)amino]-1-oxohexyl]amino]pentyl]hydroxyphosphinyl]oxy]-1-oxopropyl]-L-proline (isomer B). TLC (silica gel; isopropanol:ammonia:water, 7:2:1) R$_f$=0.50.

(e)

1-[(S)-2-[[[1-[(N$^2$-Benzoyl-L-lysyl)amino]pentyl[hydroxyphosphinyl]oxy]-1-oxopropyl]-L-proline (isomer B)

The product from part (d) (360 mg., 0.51 mmole) is dissolved in methanol (15 ml.) at room temperature under argon. The solution is hydrogenated with 20% palladium hydroxide on carbon catalyst (90 mg.) for 2 hours. The reaction mixture is filtered through Celite to remove the catalyst, and the volatiles are evaporated. Purification by column chromatography on HP-20 eluting with a water-1:1 acetonitrile/water gradient yields upon lyophilization 143 mg. of 1-[(S)-2-[[[1-[(N$^2$-benzoylL-lysyl]amino]pentyl]hydroxyphosphinyl]oxy]-1-oxopropyl]-L-proline (isomer B); m.p. 165°–170° (dec.); [α]$_D$= −76.9° (c=0.35, water). TLC (silica gel; isopropanol:ammonia:water, 7:2:1) R$_f$=0.20.

Anal. calc'd. for C$_{26}$H$_{41}$N$_4$O$_8$P·3.0 H$_2$O: C, 50.09; H, 7.60; N, 8.99; P, 5.00. Found: C, 50.09; H, 7.54; N, 8.88; P, 5.24.

EXAMPLE 16

1-[(S)-2-[[[1-[[(S)-2-Amino-1-oxohexyl]amino]pentyl]-hydroxyphosphinyl]oxy]-1-oxopropyl]-L-proline(isomer B), dilithium salt.

(a)

1-[(S)-2-[[[1-[[(S)-2-[[(1,1,-Dimethylethoxy)carbonyl]amino]-1-oxohexyl]amino]pentyl]methoxyphosphinyl]oxy-1-oxopropyl]-L-proline, ethyl ester (isomer B)

N-[(1,1-Demethylethoxy)carbonyl]-L-norleucine (432 mg., 1.87 mmole) is dissolved in tetrahydrofuran (10 ml.) at room temperature under argon. The mixture is cooled to 0° and treated with triethylamine (0.66 ml., 4.56 mmole) and pivaloyl chloride (0.28 ml.). After one hour at 0°, the reaction mixture is treated with a solution of 1-[(S)-2-[[[(1-amino)pentyl]methoxyphosphinyl]oxy]-1-oxopropyl]-L-proline, ethyl ester (isomer B) (706 mg., 1.87 mmole) in tetrahydrofuran (10 ml.) according to the procedure of Example 4 part (e) to give 759 mg. of 1-[(S)-2-[[[1-[[(S)-2-[[(1,1-dimethylethoxy)carbonyl]amino]-1-oxohexyl]amino]pentyl]methoxyphosphinyl]oxy]-1-oxopropyl]-L-proline, ethyl ester (isomer B). TLC (silica gel; methylene chloride:methanol:acetic acid, 20:1:1) R$_f$=0.74.

(b)

1-[(S)-2-[[[1-[[(S)-2-[[(1,1-Dimethylethoxy)carbonyl]amino]-1-oxohexyl]amino]pentyl]hydroxyphosphinyl]oxy]]-1-oxopropyl]-L-proline, ethyl ester (isomer B)

Trimethylamine is bubbled into a solution of the diester product from part (a) (483 mg., 0.86 mmole) in acetone (6 ml.) according to the procedure of Example 4 part (f) to yield 432 mg. of 1-[(S)-2-[[[1-[[(S)-2-[[(1,1-dimethylethoxycarbonyl]amino]-1-oxohexyl]amino]-pentyl]hydroxyphosphinyl]oxy]-1-oxopropyl]-L-proline, ethyl ester (isomer B). TLC (silica gel; isopropanol:ammonia:water, 7:2:1) $R_f$=0.60.

(c)

1-[(S)-2-[[[1-[[(S)-2-Amino-1-oxohexyl]amino]pentyl]-hydroxyphosphinyl]oxy]-1-oxopropyl]-L-proline, ethyl ester (isomer B)

The ethyl ester product from part (b) (210 mg., 0.38 mmole) is dissolved in methylene chloride (1 ml.) at room temperature under argon. The reaction mixture is cooled to 0° and trifluoroacetic acid (1 ml.) is added. After 35 minutes, the volatiles are evaporated, and the residue is dried in vacuo to yield 210 mg. of 1-[(S)-2-[[[1-[[(S)-2-amino-1-oxohexyl]amino]pentyl]hydroxyphosphinyl]oxy]-1-oxopropyl]-L-proline, ethyl ester (isomer B).

(d)

1-[(S)-2-[[[1-[[(S)-2-Amino-1-oxohexyl]amino]pentyl]-hydroxyphosphinyl]oxy]-1-oxopropyl]-L-proline (isomer B), dilithium salt The ethyl ester product from part (c) (210 mg., 0.38 mmole) is dissolved in p-dioxane (1.2 ml.) at room temperature under argon. 1N Lithium hydroxide (1.14 ml., 1.14 mmole) is added and the resulting mixture is stirred for 2 hours. The volatiles are evaporated and the residue is purified by column chromatography on HP-20 eluting with a water-1:1 water/acetonitrile gradient to yield upon lyophilization 124 mg. of 1-[(S)-2-[[[1-[[(S)-2-amino-1-oxohexyl]amino]pentyl]hydroxyphosphinyl]oxy]-1-oxopropyl]-L-proline (isomer B), dilithium salt, m.p. 195°-200° (dec.); $[\alpha]_D$= −78.5°.
(c=0.46, water). TLC (silica gel; isopropanol:ammonia:water, 7:2:1) $R_f$=0.38.

EXAMPLE 17

1-[(S)-2-[[[1-[[(S)-2-[[(1,1-Dimethylethoxy)carbonyl]amino]-1-oxohexyl]amino]pentyl]hydroxyphosphinyl]oxy]-1-oxopropyl]-L-proline (isomer B), dilithium salt 1-[(S)-2-[[[1-[[(S)-2-[[(1,1-dimethylethoxy)-carbonyl]amino]-1-oxohexyl]amino]pentyl]hydroxyphosphinyl]oxy]-1-oxopropyl]-L-proline, ethyl ester (isomer B) [222 mg., 0.40 mmole, prepared as set forth in Example 16(b)] is dissolved in p-dioxane (1 ml.) at room temperature under argon. 1N Lithium hydroxide (0.8 ml., 0.8 mmole) is added, and the resulting mixture is stirred overnight. The volatiles are evaporated, and the residue is purified by column chromatography on HP-20 eluting with water -1:1 water/acetonitrile gradient to yield upon lyphilozation 171 mg. of 1-[(S)-2-[[[1-[[(S)-2-[[(1,1-dimethylethoxy)carbonyl]amino]-1-oxohexyl]amino]-pentyl]hydroxyphosphinyl]oxy]-1-oxopropyl]-L-proline (isomer B), dilithium salt; m.p. 200°-207° (dec.); $[\alpha]_D$= −75.4° (c=0.48, water). TLC (silica gel; isopropanol:ammonia:water, 7:2:1) $R_f$=0.45.

Anal. calc'd. for $C_{24}H_{42}N_3O_9P \cdot 2Li \cdot 2.35\ H_2O$: C, 47.74; H, 7.80; N, 6.96; P, 5.13. Found: C, 47.84; H, 8.05; N, 7.16; P, 5.13.

EXAMPLE 18

[1(R*)]-1-[2-[[[1-(L-Alanylamino)pentyl]hydroxyphosphinyl]oxy]-1-oxopropyl]-L-proline (isomer B), dilithium salt (a)

1-[(S)-2[[[1-[[(S)-2-[[1,1-Dimethylethoxy)carbonyl]amino]-1-oxopropyl]amino]pentyl]methoxyphosphinyl]oxy]-1-oxopropyl]-L-proline, ethyl ester (isomer B)

N-[(1,1-Dimethylethoxy)carbonyl]-L-alanine (410 mg., 2.17 mmole) is dissolved in tetrahydrofuran (12 ml.) at room temperature under argon. The mixture is cooled to 0° and treated with triethylamine (0.76 ml., 5.32 mmole) and pivaloyl chloride (0.31 ml.). After one hour at 0°, the reaction mixture is treated with a solution of 1-[(S)-2[[[(1-amino) pentyl]methoxyphosphinyl]oxy]-1-oxopropyl]-L-proline, ethyl ester (isomer B) (820 mg., 2.17 mmole) is tetrahydrofuran (12 ml.) according to the procedure of Example 4 part (e) to give 695 mg. of 1-[(S)-2-[[[1-[[(S)-2-[[(1,1-dimethylethoxy)carbonyl]amino]-1-oxopropyl]amino]pentyl]methoxyphosphinyl]oxy]-1-L-proline, ethyl ester (isomer B). TLC (silica gel; methylene chloride:methanol:acetic acid, 20:1:1) $R_f$=0.65.

(b)

1-[(S)-2-[[[1-[[(S)-2-[[(Dimethylethoxy)carbonyl]amino]-1-oxopropyl]amino]pentyl]hydroxyphosphinyl]oxy]-1-oxopropyl]-L-proline, ethyl ester (isomer B)

Trimethylamine is bubbled into a solution of the diester product from part (a) (695 mg., 1.27 mmole) in acetone (6 ml.) according to the procedure of Example 4 part (f) to yield 650 mg. of 1-[(S)-2-[[[1-[[(S)-2-[[(1,1-dimethylethoxy)carbonyl]amino]-1-oxopropyl]amino]pentyl]hydroxyphosphinyl]oxy]-1-oxopropyl]-L-proline, ethyl ester (isomer B). TLC (silica gel; isopropanol:ammonia:water, 7:2:1) $R_f$=0.65.

(c)

[1(R)*]-1-[2-[[[1-(L-Alanylamino)pentyl]hydroxyphosphinyl]oxy]-1-oxopropyl]-L-proline, ethyl ester (isomer B)

The ethyl ester product from part (b) (650 mg., 1.22 mmole) is dissolved in methylene chloride (3.5 ml.) at room temperature under argon. The mixture is cooled to 0° and trifluoroacetic acid (3.5 ml.) is added. After 30 minutes, toluene is added, and the volatiles are evaporated. The residue is chased with toluene (2×25 ml.) and evacuated to yield 710 mg. of [1(R)*]-1-[2-[[[1-(L-alanylamino)pentyl]hydroxyphosphinyl]oxy]-1-oxopropyl]-L-proline, ethyl ester (isomer B). TLC (silica gel; isopropanol:ammonia:water, 7:2:1) $R_f$=0.41.

(d)

[1(R)*]-1-[2-[[[1-(L-Alanylamino)pentyl]hydroxyphosphinyl]oxy]-1-oxopropyl]-L-proline (isomer B), dilithium salt The ethyl ester product from part (c) (710 mg., 1.22 mmole) is dissolved in p-dioxane (3.7 ml.) at room temperature under argon. 1N Lithium hydroxide (7.4 ml.) is added, and the resulting mixture is stirred for 18 hours. The volatiles are evaporated, and the residue is purified by column chromatography on HP-20 eluting with water-1:1 water/acetonitrile gradient to yield upon lyophilization 320 mg. of [1(R)*]-1-[2-[[[1-[L- alanylamino)pentyl]hydroxyphosphinyl]oxy]-1-oxopropyl]-L-proline (isomer B), dilithium salt; m.p. 185°–192° (dec.); $[\alpha]_D = -77.5°$ (c=0.55, water). TLC (silica gel; isopropanol:ammonia:water, 7:2:1) $R_f=0.41$.

Anal. calc'd. for $C_{16}H_{28}N_3O_7P \cdot 2Li \cdot 2.30\ H_2O$: C, 41.71; H, 7.13; N, 9.12; P, 6.72. Found: C, 42,11; H, 7.19; N, 8.85; P, 6.80.

EXAMPLE 19

[1(R*)]1-[2-[[[1-L-Lysylamino)pentyl]hydroxyphosphinyl]oxy]-1-oxopropyl]-L-proline (isomer B)

(a)

1-[(S)-2-[[[1-[[N²,N⁶-Bis[(phenylmethoxy)carbonyl]-L-lysyl]amino]pentyl]methoxyphosphinyl]oxy]-1-oxopropyl]-L-proline, ethyl ester (isomer B)

N²,N⁶-Bis[(phenylmethoxy)carbonyl]-L-lysine (845 mg., 2.04 mmole) is dissolved in tetrahydrofuran (11 ml.) at room temperature under argon. The mixture is cooled to 0° and treated with triethylamine (0.71 ml., 5.0 mmole) and pivaloyl chloride (0.29 ml.). After one hour at 0°, the reaction mixture is treated with a solution of 1-[(S)-2-[[[(1-amino)pentyl]methoxyphosphinyl]oxy]-1-oxopropyl]-L-proline, ethyl ester (isomer B) (770 mg., 2.04 mmole) in tetrahydrofuran (11 ml.) according to the procedue of Example 4 part (e) to give 845 mg. of 1-[(S)-2-[[[1-[[N²,N⁶-bis[(-phenylmethoxy)carbonyl]-L-lysyl]amino]pentyl]methoxyphosphinyl]oxy]-1-oxopropyl]-L-proline, ethyl ester (isomer B). TLC (silica gel; methylene chloride:methanol:acetic acid, 7:2:1) $R_f=0.54$.

(b)

1-[(S)-2-[[[1-[[N²,N⁶-Bis[(phenylmethoxy)carbonyl]-L-lysyl]amino]pentyl]hydroxyphosphinyl]oxy]-1-oxopropyl]-L-proline, ethyl ester (isomer B)

Trimethylamine is bubbled into a solution of the diester product from part (a) (1.14 g., 1.48 mmole) in acetone (6 ml.) according to the procedure of Example 4 part (f) to yield 1.0 g. of 1-[(S)-2-[[[1-[[N²,N⁶-bis[(-phenylmethoxy)carbonyl]-L-lysyl]amino]pentyl]hydroxyphosphinyl]oxy]-1-oxopropyl]-L-proline, ethyl ester (isomer B). TLC (silica gel; isopropanol:ammonia:water, 7:2:1) $R_f=0.63$.

(c)

1-[(S)-2-[[[1-[N²,N⁶-Bis[(phenylmethoxy)carbonyl]L-lysyl]amino]pentyl]hydroxyphosphinyl]oxy]-1-oxopropyl]-L-proline (isomer B)

1N Lithium hydroxide (5 ml.) is added to a solution of the ethyl ester product from part (b) (1.08 g., 1.42 mmole) in p-dioxane (5 ml.) and the reaction mixture is worked up according to the procedure of Example 4 part (g) to yield 979 mg. of 1-[(S)-2-[[[1-[N²,N⁶-bis[(-phenylmethoxy)carbonyl]-L-lysyl]amino]pentyl]hydroxyphosphinyl]oxy]-1-oxopropyl]-L-proline (isomer B). TLC (silica gel; isopropanol:ammonia:water, 7:2:1) $R_f=0.49$.

(d)

[1(R*)]-1-[2-[[[-(L-Lysylamino)pentyl]hydroxyphosphinyl]oxy]-1-oxopropyl]-L-proline (isomer B)

The product from part (c) (979 mg., 1.34 mmole) is dissolved in methanol (42 ml.) at room temperature under argon. The solution is hydrogenated with 20% palladium hydroxide on carbon catalyst (250 mg.) for 3 hours. The reaction mixture is filtered through Celite to remove the catalyst, and the volatiles are evaporated. Purification by column chromatography on HP-20 eluting with water, 5% acetone/water, 10% acetone/water, and 15% acetone/water yields upon lyophilization 160 mg. of [1(R*)]-1-[2-[[[1-(L-lysylamino)pentyl]hydroxyphosphinyl]oxy]-1-oxopropyl]-L-proline (isomer B); m.p. 190°–195° (dec.); $[\alpha]_D = -50.2°$ (c=0.48, water). TLC (silica gel; isopropanol:ammonia:water, 7:2:1) $R_f=0.26$.

Anal. calc'd. for $C_{19}H_{37}N_4O_7P \cdot 3.85\ H_2O$: C, 42.74; H, 8.44; N, 10.50; P, 5.80. Found: C, 42,88; H, 8.73; N, 10.62; P, 6.11.

EXAMPLE 20

1-[(S)-2-[[[1-[[N²-(Cyclobutylcarbonyl)-L-lysyl]amino]-2-phenylethyl]hydroxyphosphinyl]oxy]-1-oxopropyl]-L-proline (isomer B)

(a)

[1-[[(Phenylmethoxy)carbonyl]amino]-2-phenylethyl]phosphinic acid (isomer B)

[1-[[(Phenylmethoxy)carbonyl]amino]-2-phenylethyl]phosphinic acid (50 g., 156.7 mmole) is dissolved in boiling ethanol (625 ml.) and filtered. A solution of (R)-(+)-α-methylbenzylamine (20.2 ml., 163 mmole) in ethanol (63 ml.) is added. The resulting mixture is removed from the heat, allowed to cool to room temperature, and refrigerated overnight. The white, precipitatead crystals are collected on a glass frit and air dried to give 37.5 g. of resolved product. Recrystallization from ethanol (3 times) gives 12.11 g. of solid; $[\alpha]_D = -59.3°$ (c=0.59, 9:1 dimethylformamide/water). This solid (12.11 g., 27.5 mmole) is partitioned between ethyl acetate and 1N HCl. The ethyl acetate layer is dried over sodium sulfate, filtered, and the volatiles are evaporated to give 8.81 g. of [1-[[(phenylmethoxy)carbonyl]amino]-2-phenylethyl]phosphinic acid (isomer B); $[\alpha]_D = -68.8°$ (c=0.59, methanol).

(b)

1-[(S)-2-[[Hydroxy[1-[[phenylmethoxy)carbonyl]amino]-2-phenylethyl]phosphinyl]oxy]-1-oxopropyl]-L-proline, ethyl ester.

[1-[[(Phenylmethoxy)carbonyl]amino]-2- phenylethyl]phosphinic acid (isomer B) (4.31 g., 13.5 mmole) and 1-[(S)-2-hydroxy-1-oxopropyl]-L-proline, ethyl ester (2.54 g., 12.3 mmole) are suspended in methylene chloride (60 ml.) at room temperature under argon. Dicyclohexylcarbodiimide (3.29 g., 16.0 mmole) and dimethylaminopyridine (170 mg.) are added and the resulting mixture is stirred for 3 hours. The mixture is partitioned between ethyl acetate and 5% potassium bisulfate, and the organic layer is extracted once with aqueous sodium bicarbonate and once with brine. The volatiles are evaporated, and the residue is dissolved in p-dioxane (60 ml.). A solution of sodium metaperiodate (3.27 g., 15.28 mmole) in water (60 ml.) is added, and the resulting mixture is stirred overnight. The volatiles are evaporated, and the residue is partitioned between ethyl acetate and 5% potassium bisulfate. The organic layer is washed with aqueous sodium sulfite and brine. The organic layer is dried over sodium sulfate and filtered, and the volatiles are evaporated to yield 6.13 g. of 1-[(S)-2-[[hydroxy[1-[[(phenylmethoxy)carbonyl]amino]-2-phenylethyl]phosphinyl]oxy]-1-oxopropyl]-L-proline, ethyl ester (isomer B). TLC (silica gel; methylene chloride:acetic acid:methanol, 20:1:1) $R_f$ 0.14.

(c)
1-[(S)-2-[[Methoxy[1-[[(phenylmethoxy)carbonyl-]amino]-2-phenylethyl]phosphinyl]oxy]-1-oxopropyl]-L-proline, ethyl ester (isomer B)

The ethyl ester product from part (b) (6.13 g., 11.5 mmole) in ethyl acetate (120 ml.) is treated with diazomethane according to the procedure of Example 4 part (b). The crude residue is purified by column chromatography on silica gel (LPS-1) eluting with ethyl acetate to yield 4.66 g. 1-[(S)-2-[[methoxy[1-[[(phenylmethoxy)-carbonyl]amino]-2- phenylethyl]phosphinyl]oxy]-1-oxopropyl]-L-proline, ethyl ester (isomer B). TLC (silica gel; methylene chloride:acetic acid:methanol, 20:1:1) $R_f=0.72$.

(d)
1-[(S)-2[[[(1-Amino)-2-phenylethyl]methoxyphos-phinyl]oxy]-1-oxopropyl]-L-proline, ethyl ester (isomer B)

The ethyl ester from part (c) (2.03 g., 3.7 mmole) is dissolved in methanol (60 ml.) under argon. The solution is hydrogenated at room temperature with 20% palladium hydroxide on carbon catalyst (460 mg.) for 2 hours. The mixture is filtered through Celite to remove the catalyst and the volatiles are evaporated to give 1.5 g. of 1-[(S)-2-[[[(1-amino)-2-phenylethyl]methoxyphosphinyl]oxy]-1-oxopropyl]-L-proline, ethyl ester (isomer B). TLC (silica gel; methlene chloride:acetic acid:methanol, 20:1:1) $R_f=0.2$.

(e)
1-[(S)-2-[[[1-[[(S)-6-[[(Phenylmethoxy)carbonyl]amino]-2-[(cyclobutylcarbonyl)amino]-1-oxohexyl]amino]-2-phenylethyl]methoxyphosphinyl]oxy]-1-oxopropyl]-L-proline, ethyl ester (isomer B)

$N^2$-(Cyclobutylcarbonyl)-$N^6$-[(phenylmethoxy)carbonyl]-L-lysine (650 mg., 1.8 mmole) is dissolved in tetrahydrofuran (10 ml.) at room temperature under argon. The mixture is cooled to 0° and treated with triethylamine (0.62 ml., 4.41 mmole) and pivaloyl chloride (0.25 ml.). After one hour at 0° the reaction mixture is treated with a solution of 1-[(S)-2-[[[(1-amino)-2-phenylethyl]methoxyphosphinyl]oxy]-1-oxopropyl]-L-proline, ethyl ester (isomer B) (742 mg., 1.8 mmole) in tetrahydrofuran (10 ml.) according to the procedure of Example 4 part (e). The crude reaction is purified by column chromatography (silica gel) eluting with 20% hexane/acetone to give 628 mg. of 1-[(S)-2-[[[1-[[(S)-6-[[(phenylmethoxy)carbonyl]amino]-2-[(cyclobutylcarbonyl)amino]-1-oxohexyl]amino]-2-phenylethyl]methoxyphosphinyl]oxy]-1-oxopropyl]-L-proline, ethyl ester (isomer B). TLC(silica gel; methylene chloride:acetic acid:methanol, 20:1:1) $R_f=0.57$.

(f)
1-[(S)-2-[[[1-[[(S)-6-[[(Phenylmethoxy)carbonyl]amino]-2-[(cyclobutylcarbonyl)amino-1-oxohexyl]amino]2-phenylethyl]hydroxyphosphinyl]oxy]-1-oxopropyl]-L-proline, ethyl ester (isomer B)

Trimethylamine is bubbled into a solution of the ethyl ester product from part (e) (628 mg., 0.83 mmole) in acetone (6 ml.) according to the procedure of Example 4 part (f) to give 569 mg. of 1-[(S)-2-[[[1-[[(S)-6-[[(phenylmethoxy)carbonyl]amino]-2-phenylethyl]hydroxyphosphinyl]oxy]-1-oxopropyl]-L-proline, ethyl ester (isomer B).

(g)
1-[(S)-2-[[[1-[[(S)-6-[[(Phenylmethoxy)carbonyl]amino]-2-[(cyclobutylcarbonyl)amino]-1-oxohexyl]amino]-2-phenylethyl]hydroxyphosphinyl]oxy]-1-oxopropyl]-L-proline (isomer B)

1N Lithium hydroxide (8 ml.) is added to a solution of the ethyl ester product from part (f) (569 mg., 0.77 mmole) in p-dioxane (8 ml.) according to the procedure of Example 4 part (g) to give 460 mg. of 1-[(S)-2-[[[1-[[(S)-6-[[(phenylmethoxy)carbonyl]amino]-2-[(cyclobutylcarbonyl)amino]-1-oxohexyl]amino] 2-phenylethyl]hydroxyphosphinyl]oxy]-1-oxopropyl]-L-proline (isomer B). TLC (silica gel; isopropanol:ammonia:water, 7:2:1) $R_f=0.54$.

(h)
1-[(S)-2-[[[1-[[$N^2$-(Cyclobutylcarbonyl)-L-lysyl]amino]-2-phenylethyl]hydroxyphosphinyl]oxy]-1-oxopropyl]--proline (isomer B)

The L-proline product from part (g) (460 mg., 0.64 mmole) is dissolved in methanol (25 ml.) at room temperature under argon. The solution is hydrogenated at room temperature and atmosphereic pressure with 20% palladium hydroxide on carbon catalyst (116 mg.) for 2 hours. The mixture is filtered through Celite to remove the catalyst and the crude material is purified by column chromatography on HP-20 eluting with a water-(1:1) acetonitrile/water gradient to give upon lyophilization 151 mg. of 1-[(S)-2-[[[1-[[$N^2$-(cyclobutylcarbonyl)-L-lysyl]amino]-2-phenylethyl]hydroxyphosphinyl]oxy]-1-oxopropyl]-L-proline (isomer B); m.p. 170°–175° (dec.); $[\alpha]_D=-95.6°$ (c=0.59, water). TLC (silica gel; isopropanol:ammonia:water, 7:2:1) $R_f=0.23$.

Anal. cald'd. for $C_{27}H_{41}N_4O_8P \cdot 2.06 H_2O$: C, 52.50; H, 7.36; N, 9.07; P, 5.01. Found: C, 52.71; H, 7.26; N, 9.04; P, 5.16.

EXAMPLE 21

1-[(S)-2-[[Hydroxyl[1-(L-lysylamino)-2-phenylethyl]-phosphinyl]oxy]-1-oxopropyl]-L-proline (isomer B)

(a) 1-[(S)-2-[[[1-[[$N^2$,$N^6$-Bis [(phenylmethoxy)carbonyl]-L-lysyl]amino]-2-phenylethyl]methoxyphosphinyl]oxy]-1-oxopropyl]-L-proline, ethyl ester (isomer B)

$N^2$,$N^6$-Bis[(phenylmethoxy)carbonyl]-L-lysine (788 mg., 1.9 mmole) is dissolved in tetrahydrofuran (11 ml.) at room temperature under argon. The mixture is cooled to 0° and treated with triethylamine (0.71 ml., 5.0 mmole) and pivaloyl chloride (0.27 ml.). After one hour at 0°, the reaction mixture is treated with a solution of 1-[(S)-2-[[[(1-amino)-2-phenylethyl]methoxyphosphinyl]oxy]-1-oxopropyl]-L-proline, ethyl ester (isomer B) (785 mg., 1.9 mmole) in tetrahydrofuran (11 ml.) according to the procedure of Example 4 part (e) to give 1.1 g. of 1-[(S)-2-[[[1-[[$N^2$,$N^6$-bis[(phenylmethoxy)-carbonyl]-L-lysyl]amino]-2-phenylethyl]methoxyphosphinyl]oxy]-1-oxopropyl]-L-proline, ethyl ester (isomer B). TLC (silica gel; methylene chloride:methanol:acetic acid, 20:1:1) $R_f=0.62$.

(b)
1-[(S)-2-[[[1-[[$N^2$,$N^6$-Bis[(phenylmethoxy)carbonyl]-L-lysyl]amino]-2-phenylethyl]hydroxyphosphinyl]oxy]-1-oxopropyl]-L-proline, ethyl ester (isomer B)

Trimethylamine is bubbled into a solution of the diester product from part (a) (1:1 g., 1.36 mmole) in acetone (6 ml.) according to the procedure of Example 4 part (f) to yield 1.03 g. of 1-[(S)-2-[[[1-[[N$^2$,N$^6$-bis[(phenylmethoxy)carbonyl]-L-lysyl]amino]-2-phenylethyl]hydroxyphosphinyl]oxy]1-oxopropyl]-L-proline, ethyl ester (isomer B). TLC (silica gel; isopropanol:ammonia:water, 7:2:1) R$_f$=0.67.

(c)

1-[(S)-2-[[[1-[N$^2$,N$^6$-Bis[(phenylmethoxy)carbonyl]L-lysyl]amino]-2-phenylethyl]hydroxyphosphinyl]oxy]1-oxopropyl]-L-proline (isomer B)

1N Lithium hydroxide (13 ml.) is added to a solution of the ethyl ester product from part (b) (1.03 g., 1.29 mmole) in p-dioxane (13 ml.) and the reaction mixture is worked up according to the procedure of Example 4 part (g) to yield 827 mg. of 1-[(S)-2-[[[1-[N$^2$,N$^6$-bis[(-phenylmethoxy)carbonyl]-L-lysyl]amino]-2-phenylethyl]hydroxyphosphinyl]oxy]-1oxopropyl]-L-proline (isomer B). TLC (silica gel; isporopanol:ammonia:water, 7:2:1) R$_f$=0.52.

(d)

1-[(S)-2-[[Hydroxyl[1-(L-lysylamino)-2-phenylethyl]-phosphinyl]oxy]-1-oxopropyl]-L-proline (isomer B)

The product from part (c) (807 mg., 1.05 mmole) is dissolved in methanol (45 ml.) at room temperature under argon. The solution is hydrogenated with 20% palladium hydroxide on carbon catalyst (210 mg.) for 2.5 hours. The reaction mixture is filtered through Celite to remove the catalyst, and the volatiles are evaporated. Purification by column chromatography on HP-20 eluting with a water-25% methanol/water gradient yields upon lyophilization 105 mg. of 1-[(S)-2-[[hydroxy[1-(L-lysylamino)-2-phenylethyl]phosphinyl]oxy]-1-oxopropyl]-L-proline (isomer B); m.p. 193°–198° (dec.); [α]$_D$= −55.1° (c=0.68, water). TLC (silica gel; isopropanol:ammonia:water, 7:2:1) R$_f$=0.14.

Anal. calc'd. for C$_{22}$H$_{35}$N$_4$O$_7$P·2.24 H$_2$O: C, 49.03; H, 7.38; N, 10.40; P, 5.75. Found: C, 49.04; H, 7.47; N, 10.43; P, 5.79.

EXAMPLE 22

1-[(S)-2-[[Hydroxy[1-[[N$^2$-(4-morpholinycarbonyl)-L-lysyl]amino]pentyl]phosphinyl]oxy]-1-oxopropyl]-L-proline (isomer B)

(a)

N$^2$-[(1,1-Dimethylethoxy)carbonyl]-N$^6$-[(phenylmethoxy)carbonyl]-L-lysine, ethyl ester N$^2$-[(1,1-Dimethylethoxy)carbonyl]-N$^6$-[(phenylmethoxy)carbonyl]-L-lysine (5.48 g., 14.4 mmole) is dissolved in ethyl acetate (130 ml.). Diazomethane is added until a yellow color persists. Acetic acid is added to quench the excess diazomethane, and the volatiles are evaporated. The residue is partitioned between ethyl acetate and saturated sodium bicarbonate, the organic layer is dried over sodium sulfate, filtered, and then the volatiles are evaporated. Purification of the residue by column chromatography on LPS-1 silica eluting with 30% ethyl acetate/hexane yields 4.0 g. of N$^2$-[(1,1-dimethylethoxy)carbonyl]-N$^6$-[(phenylmethoxy)carbonyl]-L-lysine, methyl ester. TLC (silica gel; hexane:acetone, 1:1) R$_f$=0.69.

(b) N$^6$-[(Phenylmethoxy)carbonyl]-L-lysine, methyl ester, trifluoroacetate

The methyl ester product from part (a) (4.0 g., 10.15 mmole) is dissolved in methylene chloride (30 ml.) at room temperature under argon. The mixture is cooled to 0°, trifluoroacetic acid (30 ml.) is added, and the resulting mixture is stirred for 30 minutes. Toluene is added, and the volatiles are evaporated. The residue is washed with toluene (2×) and evacuated thoroughly to yield 4.0 g. of N$^6$-[(phenylmethoxy)carbonyl]-L-lysine, methyl ester, trifluoroacetate. TLC (silica gel; hexane:acetone, 1:1) R$_f$=0.10.

(c)

N$^2$-[(4-Morpholinyl)carbonyl]-N$^6$-[(phenylmethoxy)carbonyl]-L-lysine, methyl ester Methylene chloride (20 ml.) is added to a 1.93M solution of phosgene in toluene (12.62 ml., 24.36 mmol) at room temperature under argon. The mixture is cooled to −35°, and a solution containing morpholine (1.06 ml., 12.18 mmole), N-methylmorpholine (3.0 ml., 26.8 mmole), and methylene chloride (75 ml.) is added dropwise over about 25 minutes. The mixture is warmed to room temperature and is stirred for an additonal 30 minutes. The volatiles are evaporated, methylene chloride (20 ml.) is added, and the volatiles are evaporated again. A solution containing N$^6$-[(phenylmethoxy)carbonyl]-L-lysine, methyl ester, trifluoroacetate (4.0 g., 10.15 mmole), N-methylmorpholine (2.46 ml., 22.3 mmole), and methylene chloride (100 ml.) is added, and the resulting mixture is stirred at room temperature under argon overnight. The volatiles are evaporated, and the residue is partitioned between ethyl acetate and water. The aqueous layer is extracted wtih ethyl acetate (twice) and the combined organic layers are extracted with water, 10% HCl, saturated aqueous sodium bicarbonate and brine, the organic layer is dried over sodium sulfate, filtered, and the volatiles are evaporated. The residue is purified by column chromatography (LPS-1 silica) eluting with 30% acetone/hexane and 1:1 acetone/hexane to give 1.8 g. of N$^2$-[(4-morpholinyl)carbonyl]-N$^6$-[(phenylmethoxy)carbonyl]-L-lysine, methyl ester. TLC (silica gel; hexane:acetone, 1:1) R$_f$=0.31.

(d)

N$^2$-[(4-Morpholinyl)carbonyl]-N$^6$-[(phenylmethoxycarbonyl]-L-lysine

1N Lithium hydroxide (35 ml.) is added to a solution of the methyl ester product from part (c) (1.8 g., 4.42 mmole) in p-dioxane (35 ml.) at room temperature under argon. The resulting mixture is stirred overnight, and then the volatiles are evaporated. The residue is partitioned between ethyl acetate and 5% potassium bisulfate. The organic layer is dried over sodium sulfate, and the volatiles are evaporated to give 1.5 g. of N$^2$-[(4-morpholinyl)carbonyl]-N$^6$-[(phenylmethoxy)carbonyl]-L-lysine. TLC (silica gel; methylene chloride:acetic acid:methanol; 20:1:1) R$_f$=0.20.

(e)

1-[(S)-2-[[[1-[[(S)-6-[[(Phenylmethoxy)carbonyl]amino]-2-[(4-morpholinylcarbonyl)amino]-1-oxohexyl]amino]-pentyl]methoxyphosphinyl]oxy]-1-oxopropyl]-L-proline, ethyl ester (isomer B)

N$^2$-[(4-Morpholinyl)carbonyl]-N$^6$-[(phenylmethoxy)carbonyl]-L-lysine (672 mg., 1.71 mmole) is dissolved in tetrahydrofuran (10 ml.) at room temperature under argon. The mixture is cooled to 0° and treated with triethylamine (0.6 ml., 4.19 mmole) and pivaloyl chloride (0.24 ml.). After one hour at 0°, the reaction mixture is treated with a solution of 1-[(S)-2-[[[(1-amino)-pentyl]methoxyphosphinyl]oxy]-1-oxopropyl]-L-proline, ethyl ester (isomer B) (547 mg., 1.71 mmole) is tetrahydrofuran (10 ml.) according to the procedure of Example 4 part (e) to give 860 mg. of 1-[(S)-2-[[[1-[[(S)-6-[[(phenylmethoxy)carbonyl]amino]-2-[(4-morpholinylcarbonyl)amino]-1-oxohexyl]amino]pentyl]methoxyphosphinyl]oxy]-1-oxopropyl]-L-proline, ethyl ester (isomer B). TLC (silica gel; methylene chloride:acetic acid:methanol, 20:1:1) $R_f=0.56$.

(f)

1-[(S)-2-[[[1-[[(S)-6-[[(Phenylmethoxy)carbonyl]amino]-2-[(4morpholinylcarbonyl)amino]-1-oxohexyl]amino]-pentyl]hydroxyphosphinyl]oxy]-1-oxopropyl]-L-proline, ethyl ester (isomer B)

Trimethylamine is bubbled into a solution of the diester product from part (e) (860 mg., 1.14 mmole) in acetone (6 ml.) according to the procedure of Example 4 part (f) to yield 814 mg. of 1-[(S)-2-[[[1-[[(S)-6-[[(phenylmethoxy)carbonyl]amino]-2-[(4-morpholinycarbonyl)amino]-1-oxohexyl]amino]pentyl]hydroxyphosphinyl]oxy]-1-oxopropyl]-L-proline, ethyl ester (isomer B). TLC (silica gel; isopropanol: ammonia:water, 7:2:1) $R_f=0.65$.

(g)

1-[(S)-2-[[[1-[[(S)-6-[[(Phenylmethoxy)carbonyl]amino]-2-[(4-morpholinylcarbonyl)amino]-1-oxohexyl]amino]-pentyl]hydroxyphosphinyl]oxy]-1-oxopropyl]-L-proline (isomer B)

1N Lithium hydroxide (13 ml.) is added to a solution of the ethyl ester product from part (f) (814 mg., 1.10 mmole) in p-dioxane (13 ml.) and the reaction mixture is worked up according to the procedure of Example 4 part (g) to yield 474 mg. of 1-[(S)-2-[[[1-[[(S)-6[[(phenylmethoxy)carbonyl]amino]-2-[(4-morpholinylcarbonyl)amino]-1-oxohexyl]amino]pentyl]hydroxyphosphinyl]oxy]-1-oxopropyl]-L-proline (isomer B). TLC (silica gel; isopropanol:ammonia; water, 7:2:1) $R_f=0.55$.

(h)

1-[(S)-2-[[Hydroxy[1-[[N²-(4-morpholinylcarbonyl)L-lysyl]amino]pentyl]phosphinyl]oxy]-1-oxopropyl]-L-proline (isomer B)

The product from part (g) (474 mg., 0.67 mmole) is dissolved in methanol (30 ml.) at room temperature under argon. The solution is hydrogenated with 20% palladium hydroxide on carbon catalyst (125 mg.) for 2.5 hours. The reaction mixture is filtered through Celite to remove the catalyst, and the volatiles are evaporated. Purification of the residue by chromatography on HP-20 eluting with a water - 1:1 acetonitrile/water gradient yields upon lyophilization 245 mg. of 1-[(S)-2-[[hydroxy[1-[[N²-(4-morpholinylcarbonyl)-L-lysyl-]amino]pentyl]phosphinyl]oxy]-1-oxopropyl]-L-proline (isomer B); m.p. 165°–170°; $[\alpha]_D = -55°$ (c=0.64, water). TLC (silica gel; isopropanol:ammonia:water, 7:2:1) $R_f=0.48$.

Anal. calc'd. for $C_{24}H_{44}N_5O_9P \cdot 1.6 H_2O$: C, 47.53; H, 7.84; N, 11.55; P, 5.11. Found: C, 47.57; H, 7.62; N, 11.53; P, 5.18.

EXAMPLE 23

1-[(S)-2-[[[1-[(S)-6-Amino-2-[(4-morpholinylcarbonyl)oxy]-1-oxohexyl]amino]pentyl]hydroxyphosphinyl]oxy]-1-oxopropyl]-L-proline (isomer B)

(a)

(S)-6-[[(Phenylmethoxy)carbonyl]amino]-2-hydroxyhexanoic acid, methyl ester

Diazomethane is added to a solution of (S)-6-[(phenylmethoxy)carbonyl]amino]-2-hydroxyhexanoic acid (3.37 g., 12 mmole) in ethyl acetate (150 ml.) until a yellow color persists. Acetic acid is added to quench the excess diazomethane, and the volatiles are evaporated. The residue is partitioned between ethyl acetate and saturated aqueous sodium bicarbonate. The organic layer is dried over sodium sulfate and filtered, and the volatiles are evaporated to yield 3.55 g. (S)-6-[[(phenylmethoxy)carbonyl]amino]-2-hydroxyhexanoic acid, methyl ester. TLC (silica gel; hexane:ethyl acetate, 1:1) $R_f=0.44$.

(b)

(S)-2-[(4-Morpholinylcarbonyl)oxy]-6-[[(phenylmethoxy)carbonyl]amino]hexanoic acid, methyl ester Methylene chloride (20 ml.) is added to a 1.93M solution of phosgene in toluene (12.4 ml., 24 mmole) ar room temperature under argon. The mixture is cooled to −35°, and a solution of (S)-6-[[(phenylmethoxy)carbonyl]amino]-2-hydroxyhexanoic acid, methyl ester (3.55 g., 12 mmole) and N-methylmorpholine (2.96 ml., 26.4 mmole) in methylene chloride (75 ml.) is added dropwise over about 25 minutes. The mixture is stirred at −35° for 30 minutes and then at room temperature for an additional 30 minutes. The volatiles are evaporated, methylene chloride (20 ml.) is added to the residue, and the volatiles are evaporated once again. A solution of morpholine (10.14 ml., 12 mmole) and N-methylmorpholine (2.7 ml. 24 mmole) in methylene chloride (100 ml.) is added, and the resulting mixture is stirred at room temperature overnight. The volatiles are evaporated, and the residue is partitioned between ethyl acetate and water. The aqueous layer is extracted with ethyl acetate (twice), and then the combined organic layers are washed with water, 10% HCl, saturated aqueous sodium bicarbonate, and brine. The organic layer is dried over sodium sulfate, filtered, and the volatiles evaporated. The residue is purified by column chromatography (LPS-1 silica) eluting with 1:1 hexane/acetone to yield 3.48 g. of (S)-2-[(4-morpholinylcarbonyl)oxy]-6-[[(phenylmethoxy)carbonyl]amino]hexanoic acid, methyl ester. TLC (silica gel; hexane:acetic acid, 1:1) $R_f=0.36$.

(c)

(S)-2-[(4-Morpholinylcarbonyl)oxy]-6-[[(phenylmethoxy)carbonyl]amino]hexanoic acid 1N Lithium hydroxide (70 ml.) is added to a solution of the methyl ester product from part (b) (3.43 g., 8.41 mmole) in p-dioxane (70 ml.) at room temperature under argon. The resulting mixture is stirred overnight, and then the volatiles are evaporated. The residue is partitioned between ethyl acetate and 5% potassium bisulfate. The organic layer is dried over sodium sulfate and the volatiles are evaporated to give 3.82 g. of (S)-2-[(4-morpholinylcarbonyl)oxy]-6-[[(phenylmethoxy)carbonyl]amino]hexanoic acid. TLC (silica gel; methylene chloride:acetic acid:methanol, 20:1:1) $R_f=0.23$.

(d)
1-[(S)-2-[[[1-[[(S)-6-[[(phenylmethoxy)carbonyl]amino]-2-[(4-morpholinylcarbonyl)oxy]-1-oxohexyl]amino]pentyl]methoxyphosphinyl]oxy]-1-oxopropyl]-L-proline, ethyl ester (isomer B)

(S)-2-[(4-Morpholinylcarbonyl)oxy]-6-[[(phenylmethoxy)carbonyl]amino]hexanoic acid (993 mg., 2.52 mmole) is dissolved in tetrahydrofuran (15 ml.) at room temperature under argon. The mixture is cooled to 0° and treated with triethylamine (0.88 ml., 6.17 mmole) and pivaloyl chloride (0.35 ml.). After one hour at 0°, the reaction mixture is treated with a solution of 1-[(S)-2-[[[(1-amino)pentyl]methoxyphosphinyl]oxy]-1-oxopropyl]-L-proline, ethyl ester (isomer B) (951 mg., 2.52 mmole) in tetrahydrofuran (15 ml.) according to the procedure of Example 4 part (e) to give 670 mg. of 1-[(S)-2-[[[1-[[(S)-6-[[(phenylmethoxy)carbonyl]amino]-2-[(4-morpholinylcarbonyl)oxy]-1-oxohexyl]amino]pentyl]methoxyphosphinyl]oxy]-1-oxopropyl]-L-proline, ethyl ester (isomer B). TLC (silica gel; methylene chloride:acetic acid:methanol, 20:1:1) $R_f$=0.60.

(e)
1-[(S)-2-[[[1-[[(S)-6-[[(phenylmethoxy)carbonyl]amino]-2-[(4-morpholinylcarbonyl)oxy]-1-oxohexyl]amino]pentyl]hydroxyphosphinyl]oxy]-1-oxopropyl]-L-proline, ethyl ester (isomer B)

Trimethylamine is bubbled into a solution of the diester product from part (d) (670 mg., 089 mmole) in acetone (6 ml.) according to the procedure of Example 4 part (f) to yield 700 mg. of 1-[(S)-2-[[[1-[[(S)-6-[[phenylmethoxy)carbonyl]amino]-2-[(4-morpholinylcarbonyl)oxy]-1-oxohexyl]amino]pentyl]hydroxyphosphinyl]oxy]-1-oxopropyl]-L-proline, ethyl ester (isomer B). TLC (silica gel; isopropanol:ammonia:water, 7:2:1) $R_f$=0.65.

(f)
1-[(S)-2-[[[1-[[(S)-6-[[(phenylmethoxy)carbonyl]amino]-2-[(4-morpholinylcarbonyl)oxy]-1-oxohexyl]amino]pentyl]hydroxyphosphinyl]oxy]-1-oxopropyl]-L-proline (isomer B)

1N Lithium hydroxide (11 ml) is added to a solution of the ethyl ester product from part (e) (700 mg., 0.89 mmole) in p-dioxane (11 ml.) and the reaction mixture is worked up according to the procedure of Example 4 part (g) to yield 300 mg. of 1-[(S)-2-[[[1-[[(S)-6-[[(phenylmethoxy)carbonyl]amino]-2-[(4-morpholinylcarbonyl)oxy]-1-oxohexyl] amino]pentyl]hydroxyphosphinyl]oxy]-1-oxopropyl]L-proline (isomer B). TLC (silica gel; isopropanol:ammonia:water, 7:2:1) $R_f$=0.47.

(g) 1-[(S)-2-[[[1-[(S)-6-Amino-2-[(4-morpholinylcarbonyl)oxy]-1-oxohexyl]amino]pentyl]hydroxyphosphinyl]oxy]-1-oxopropyl]-L-proline (isomer B)

The product from part (f) (300 mg., 0.42 mmole) is dissolved in methanol (20 ml.) at room temperature under argon. The solution is hydrogenated with 20% palladium hydroxide on carbon catalyst (125 mg.) for 2 hours. The reaction mixture is filtered through Celite to remove the catalyst, and the volatiles are evaporated. Purification of the residue by chromatography on HP-20 eluting with a water-1:1 acetonitrile/water gradient yields upon lyophilization 210 mg. of 1-[(S)-2-[[[1-[(S)-6-amino-2-[(4-morpholinylcarbonyl)oxy]-1-oxohexyl]amino]pentyl]hydroxyphosphinyl]oxy]-1-oxopropyl]-L-proline (isomer B); m.p. 145°–150° (dec.); $[\alpha]_D$= −58.5° (c=0.41, water). TLC (silica gel; isopropanol:ammonia:water, 7:2:1) $R_f$=0.31.

Anal. calc'd. for $C_{24}H_{43}N_4O_{10}P \cdot 1.34 H_2O$: C, 47.82; H, 7.64; N, 9.30; P, 5.14. Found: C, 48.00; H, 7.33; N, 9.23; P, 5.16.

EXAMPLE 24

1-[(S)-2-[[[2(S)-[[(S)-6-Amino-2-[(cyclobutylcarbonyl)amino]-1-oxohexyl]amino]hexyl]hydroxyphosphinyl]oxy]-1-oxopropyl]-L-proline (a) (S)-2-[[(4-Methylphenyl)sulfonyl]amino]-1-hexanol, 4-methylbenzenesulfonate ester A suspension of L-norleucine (6.5 g., 49.5 mmole) in absolute ethanol (70 ml.) is cooled to 0° (ice bath) and saturated with HCl gas. The mixture is allowed to warm to room temperature and stirred overnight. A stream of nitrogen is then passed through the solution to remove the bulk of the HCl and the mixture is evaporated to dryness. The solid residue is triturated with isopropyl ether, filtered, and dried to give 9.10 g. of L-norleucine, methyl ester, monohydrochloride as a fluffy white solid; m.p. 131°–132°; $[\alpha]_D$= +15.4° (c=1.10, methanol). TLC (silica gel; methylene chloride:acetic acid:methanol, 8:1:1) $R_f$=0.51.

A solution of L-norleucine, methyl ester, monohydrochloride (8.60 g., 43.9 mmole) is 50% aqueous ethanol (120 ml.) is added dropwise to a solution of sodium borohydride (7.8 g., 206 mmole) in 50% aqueous ethanol (120 ml.) at room temperature. After the addiiton is complete, the mixture is refluxed for 5 hours and then allowed to stand at room temperature overnight. The ethanol and most of the water are evaporated off and the residue is partitioned between ethyl acetate and water (75 ml. each). The ethyl acetate phase is separated and the aqueous phase is re-extracted with ethyl acetate. The combined extracts are washed with saturated sodium chloride, dried over sodium sulfate, and evaporated to give 3.85 g. of crude amino alcohol.

This crude amino alcohol (3.8 g., 32.8 mmole) is taken up in dry pyridine (30 ml.), cooled in an ice-bath under argon, and treated with p-toluenesulfonyl chloride (12.6 g., 66 mmole) in small portions over a 15 minute period. The mixture is allowed to slowly warm to room temperature. After 3 hours, the mixture is partitioned between ethyl acetate-1N HCl. The ethyl acetate phase is washed successively with 1N HCl, saturated sodium bicarbonate, and saturated sodium chloride, dried over sodium sulfate, and evaporated. The orange residue is filtered through a pad of silia gel (75 g.) eluting with methylene chloride. Evaporation of the methylene chloride and trituration of the residue with diisopropyl ether gives 10.55 g. of (S)-2-[[(4-methylphenyl)sulfonyl]amino]-1-hexanol, 4-methylbenzenesulfonate ester; m.p. 93°–94°. An analytical sample is recrystallized from ethyl acetate-hexane; m.p. 93°–94°; $[\alpha]_D$= −48.3° (c=1.0, methanol). TLC (silica gel; ethyl acetate;hexane, 1:2) $R_f$=0.42.

(b)
(S)-[2-[[(4-Methylphenyl)sulfonyl]amino]hexyl]phosphonic acid, diethyl ester Diethyl phosphite (8.9 ml., 69 mmole) is dissolved in dry tetrahydrofuran (125 ml.) under argon in a 250 ml. round-bottomed flask equipped with a condenser. Sodium hydride (2.4 g.) is added in small portions with frothing and bubbling. When the evolution of hydrogen ceases, the reaction mixture is heated to reflux for 45 minutes. It is then cooled to room temperature, and a solution of (S)-2-[[(4-methylphenyl)sulfonyl]amino]-1-hexanol, 4-methylbenzenesulfonate ester (18.1 mmole) is added dropwise over 5 minutes. A white solid precipitates. The mixture is then heated to reflux for 3.5 hours. It is cooled and partitioned between ethyl acetate and 5% potassium bisulfate. The ethyl acetate layer is washed with 5% potassium bisulfate, saturated sodium bicarbonate, and brine, and then concentrated in vacuo. The resulting gum is triturated with hexane to give 6.45 g. of beige solid (S)-[2-[[(4-methylphenl)sulfonyl]amino]hexyl]phosphonic acid, diethyl ester.

(c) (S)-[2-[[(Phenylmethoxy)carbonyl]amino]hexyl]phosphonic acid

The diethyl ester product from part (b) (6.45 g., 17.1 mmole) is dissolved in 48% hydrogen bromide (130 ml.) with phenol (10.4 g.) and refluxed for 6 hours. The mixture is cooled, diluted with water, and washed with ethyl acetate. The aqueous layer is concentrated to an orange syrup chasing with water to remove hydrogen bromide and give (S)-2-(aminohexyl)phosphonic acid as an oil.

This oil is dissolved in water (30 ml.) and cooled to 0°. Benzyl chloroformate (1.4 ml.) is added and the pH is adjusted to 9.5 with sodium hydroxide. The reaction mixture is stirred overnight at room temperature. The aqueous solution is washed with ethyl acetate, acidified to pH 2, and extracted with ethyl acetate. The ethyl acetate extract is washed with brine and concentrated to give 950 mg. of orange solid (S)-[2-[[(phenylmethoxy)carbonyl]amino]hexyl]phosphonic acid.

(d) (S)-[2-[[(Phenylmethoxy)carbonyl]amino]hexyl]phosphonic acid, monomethyl ester The phosphonic acid product from part (c) (1.29 g., 4.1 mmole) is dissolved in ethy acetate (50 ml.) and treated with excess diazomethane. A few drops of acetic acid are added to the ethyl acetate solution to decolorize, and the solution is then washed with saturated bicarbonate and brine, and concentrated to give 1.38 g. of (S)-[2-[[(phenylmethoxy)carbonyl]amino]hexyl]phosphonic acid, dimethyl ester.

This dimethyl ester (1.38 g., 4.01 mmole) is stirred under argon with dioxane (4 ml.) and 1N lithium hydroxide (4 ml.). The reaction proceeds very slowly, so the solution is heated to 50° overnight. The basic reaction mixture is washed twice with ethyl acetate, then acidified and extracted with ethyl acetate once more. The latter ethyl acetate layer is concentrated to give 800 mg. of (S)-[2-[[(phenylmethoxy)carbonyl]amino]hexyl]phosphonic acid, monomethyl ester. TLC (silica gel; methylene chloride:methanol:acetic acid, 20:1:1) $R_f=0.21$.

(e) 1-[(S)-2-[[Methoxy[(S)-2-[[(phenylmethoxy)carbonyl]amino]hexyl]phosphinyl]oxy]-1-oxopropyl]-L-proline, ethyl ester Phosphorus pentachloride (0.54 g., 2.6 mmole) is suspended in methylene chloride (4 ml.) and cooled to −10°. A solution of (S)-[2-[[(phenylmethoxy)carbonyl]amino]hexyl]phosphonic acid, monomethyl ester (750 mg., 2.27 mmole) is methylene chloride (4 ml.) is added. The mixture is warmed to room temperature and stirred for 1.5 hours. The solvent is removed in vacuo, chasing with benzene, to give a yellow oil. This oil is dissolved in methylene chloride and cooled to −78°. A solution of 1-[(S)-2-hydroxyl-1-oxopropyl]-L-proline, ethyl ester (513 mg., 2.6 mmole) in methylene chloride (5 ml.) is added followed by triethylamine (0.5 ml.) and dimethylaminopyridine (100 mg.). The reaction mixture is gradually warmed to room temperature and stirred for 2 hours. It is then partitioned between 5% potassium bisulfate and ethyl acetate. The ethyl acetate solution is washed with saturated sodium bicarbonate and brine, and concentratead in vacuo to give 1:22 g. of an oil. This oil is chromotographed in silica (LPS-1) eluting with ethyl acetate to give 700 mg. of 1-[(S)-2-[[methoxy[(S)-2-[[(phenylmethoxy)carbonyl]amino]hexyl]phosphinyl]oxy]-1-oxopropyl]-L-proline, ethyl ester. TLC (silica gel; methylene chloride:methanol:acetic acid, 20:1:1) $R_f=0.79$.

(f) 1-[(S)-2-[[(S)-2-(Aminohexyl)methoxyphosphinyl]oxy]-1-oxopropyl]-L-proline, ethyl ester The diester product from part (e) (700 mg., 1.33 mmole) is dissolved in methanol (50 ml.) and hydrogenated with 20% palladium on carbon catalyst (120 mg.). After the reaction is completed, the solution is filtered and concentrated to give 520 mg. of 1-[(S)-2-[[(S)-2-(aminohexyl)methoxyphosphinyl]oxy]-1-oxopropyl]-L-proline, ethyl ester. TLC (silica gel; methylene chloride:methanol:acetic acid, 20:1:1) $R_f=0.07$.

(g) 1-[(S)-2-[[[2(S)-[[(S)-6-[[(Phenylmethoxy)carbonyl]amino]-2-]-2-[(cyclobutylcarbonyl)amino]-1-oxohexyl]amino]hexyl]methoxyphosphinyl]oxy]-1-oxopropyl]-L-proline, ethyl ester $N^2$-(Cyclobutylcarbonyl)-$N^6$-[(phenylmthoxy)carbonyl]-L-lysine (481 mg., 1.33 mmole) is dissolved in tetrahydrofuran (5 ml.) under argon and cooled to 9°. Triethylamine (0.45 ml.) is added followed by pivaloyl chloride (0.18 ml., 0.176 g., 1.46 mmole). The resulting suspension is stirred for one hour at 0°. A solution of 1-[(S)-2-[[(S)-2-(aminohexyl)methoxyphosphinyl]oxy]-1-1-oxopropyl]-L-proline, ethyl ester (520 mg., 1.32 mmole) is added. The reaction mixture is allowed to warm to room temperature and stirred overnight. It is partitioned between ethyl acetate and 5% potassium bisulfate. The ethyl acetate solution is washed with 5% potassium bisulfate, saturated sodium bicarbonate, and brine, and then concentrated to give 1.07 of a crude oil. This is chromatographed on silica (LPS-1) eluting with 10% hexane in acetone. The product containing fractions are combined to give 700 mg. of 1-[(S)-2-[[[2(S)-[[(S)-6-[[(phenylmethoxy)carbonyl]amino]-2-[(cyclobutylcarbonyl)amino]-1-oxohexyl]amino]hexyl]methoxyphosphinyl]oxy]-1-oxopropyl]-L-proline, ethyl ester. (h) 1-[(S)-2-[[[2(S)-[[(S)-6-[[(Phenylmethoxy)carbonyl]amino]-2-[(cyclobutylcarbonyl)amino]-1-oxohexyl]amino]hexyl]hydroxyphosphinyl]oxy]-1-oxopropyl]-L-proline, ethyl ester The diester product from part (g) (700 mg., 0.95 mmole) is dissolved in acetone (10 ml.). The solution is saturated with trimethylamine and then heated at 95° in a sealed tube. The mixture is partitioned between ethyl acetate and 5% potassium bisulfate. The water layer is acidified with concentrated HCl and extracted with ethyl acetate. The combined ethyl acetate solutions are washed with 5% potassium bisulfate and brine, and saturated in vacuo to give 1-[(S)-2-[[[2(S)-[[(S)-6-[[(phenylmethoxy)carbonyl]amino]-2-[(cyclobutylcarbonyl- )amino]-1-oxohexyl]amino]hexyl]hydroxyphosphinyl]oxy]-1-oxopropyl]-L-proline, ethyl ester. TLC (silica gel; methylene chloride:methanol:acetic acid; 20:1:1) $R_f = 0.25$.

(i)

1-[(S)-2-[[[2(S)-[[(S)-6-[[(Phenylmethoxy)carbonyl]amino]-2-[(cyclobutylcarbonyl)amino]-1-oxohexyl]amino]hexyl]hydroxyphosphinyl]oxy]-1-oxopropyl]-L-proline The ethyl ester product from part (h) is dissolved in dioxane (3 ml.) with 1N lithium hydroxide (3 ml.) and stirred overnight under argon. The reaction mixture is partitioned between ethyl acetate and 5% potassium bisulfate. The ethyl acetate layer is washed with 5% potassium bisulfate and brine, and concentrated to give 1-[(S)-2-[[[2(S)-6-[[(phenylmethoxy)carbonyl]amino]-2-[(cyclobutylcarbonyl)amino]-1-oxohexyl]amino]hexyl]hydroxyphosphinyl]oxy]-1-oxopropyl]-L-proline as an oil. TLC (silica gel; isopropanol:ammonia:water, 7:2:1) $R_f = 0.65$.

(j)

1-[(S)-2-[[[2(S)-[[(S)-6-Amino-2-[(cyclobutylcarbonyl)amino]-1-oxohexyl]amino]hexyl]hydroxyphosphinyl]oxy]-1-oxopropyl]-L-proline The product from part (i) is dissolved in methanol (500 ml.) and stirred overnight under atmospheric hydrogen with 20% palladium hydroxide on carbon catalyst (50 mg.). The solution is filtered and concentrated to give an oil that is purified chromatographically on HP-20 eluting with a 1:1 water:acetonitrile gradient. The product containing fraction is concentratead, dissolved in water, millipore filtered, frozen, and lyophilized to give 55 mg. of solid 1-[(S)-2-[[[2(S)-[[(S)-6-amino-2-[(cyclobutylcarbonyl)amino]-1-oxohexyl]amino]hexyl]hydroxyphosphinyl]oxy]-1-oxopropyl]L-proline; forms glass at 140°; $[\alpha]_D = -37.2°$ (c=0.50, methanol). TLC (silica gel; isopropanol:ammonia:water, 7:2:1) $R_f = 0.45$.

Anal. calc'd. for $C_{25}H_{48}N_4O_8P \cdot 1.55 H_2O$ C, 51.01; H, 8.24; N, 9.52; P, 5.26. Found: C, 51.01; H, 8.40; N, 9.56; P, 5.28.

Similarly, the following compounds of the formula

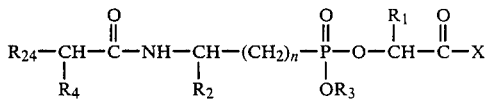

can be obtained.

| Example | R24 | R4 | R2 | R3 | n | R1 | X |
|---|---|---|---|---|---|---|---|
| 25 | 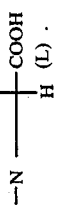 | —H | —C4H9 | —H | zero | —CH3 |  |
| 26 | 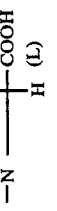 | —(CH2)4—NH2 | —C4H9 | —H | zero | —CH3 | 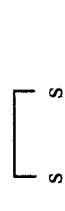 |
| 27 |  | —(CH2)4—NH2 | —C4H9 | —H | zero | —CH3 | 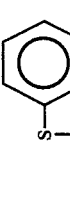 |
| 28 | 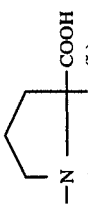 | —(CH2)4—NH2 | —C4H9 | —H | one | —CH3 | 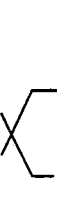 |
| 29 | 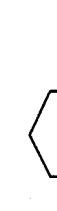 | —(CH2)4—NH2 | —C4H9 | —H | zero | —CH3 | 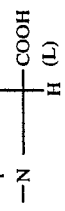 |
| 30 |  | —CH3 | —C4H9 | —H | one | —(CH2)4—NH2 | |

-continued

| Example | R24 | R4 | R2 | R3 | n | R1 | X |
|---|---|---|---|---|---|---|---|
| 31 | piperidine-N-C(=O)-NH- | -(CH2)4-NH-C(=NH)NH2 | -CH2-C6H5 | -H | zero | -CH3 | -N(cyclohexylmethyl-CH2-)-CH(COOH)-H (L) |
| 32 | thiophene-2-C(=O)-NH- | -(CH2)5-NH2 | -C4H9 | -H | zero | -CH3 | -N(2-benzyl-C6H4-CH2-)-CH(COOH)-H (L) |
| 33 | pyridine-2-C(=O)-O- | -(CH2)4-NH2 | -C4H9 | -H | one | -CH3 | -N(fused benzo)-CH(COOH)-H (L) |
| 34 | (H3C)2N-C(=O)-NH- | -CH2-C6H5 | -C4H9 | -H | zero | -(CH2)4-NH-C(=NH)NH2 | -N(2-cyclohexylmethyl-cyclohexyl)-CH(COOH)-H (L) |
| 35 | 4-Cl-C6H4-C(=O)-NH- | -(CH2)4-NH2 | -(CH2)2-C6H5 | -H | zero | -CH3 | -N(fused cyclohexyl)-CH(COOH)-H (L) |

-continued

| Example | R24 | R4 | R2 | R3 | n | R1 | X |
|---|---|---|---|---|---|---|---|
| 36 | C6H5-CH2-O-C(=O)-NH- | -(CH2)4-NH2 | -C4H9 | -H | one | -CH3 | proline-like: N-CH(COOH)-H (L) (pyrrolidine ring) |
| 37 | H3C-N(piperazine)-C(=O)-O- | -(CH2)4-NH2 | -C4H9 | -H | one | -CH3 | proline-like: N-CH(COOH)-H (L) (pyrrolidine ring) |
| 38 | cyclohexyl-C(=O)-NH- | -(CH2)4-NH2 | -C4H9 | -H | zero | -CH3 | -NH-CH2-COOH |
| 39 | cyclohexyl-CH2-C(=O)-O- | -CH3 | -CH2-C6H5 | -H | zero | -(CH2)4-NH2 | -NH-CH(CH3)-COOH (L) |
| 40 | C6H5-C(=O)-NH- | -CH2-S-CH3 | -C4H9 | -H | zero | -CH3 | -NH2-CH(CH2-C6H5)-COOH (L) |
| 41 | cyclobutyl-CH2-C(=O)-NH- | -(CH2)2-C6H5 | -CH3 | -H | zero | -CH3 | -NH2-CH(CH2-indolyl)-COOH (L) |
| 42 | cyclopentyl-(CH2)2-C(=O)-NH- | -CH3 | -C4H9 | -H | one | -CH3 | -NH2-CH(CH2-imidazolyl)-COOH (L) |

-continued

| Example | R24 | R4 | R2 | R3 | n | R1 | X |
|---------|-----|-----|-----|-----|---|-----|---|
| 43 | phenyl-C(=O)-NH- | -(CH2)4-NH2 | -C2H5 | -H | zero | -CH3 | -N(3,4-dimethoxyphenyl)-CH2-COOH |
| 44 | cyclobutyl-C(=O)-NH- | -(CH2)4-NH2 | -C4H9 | -CH(OC(=O)OC2H5)-CH(CH3)2 | zero | -CH3 | piperidine ring with -CH2-CH(cyclohexyl)-CH(COOH)(H) (L) attached to N |
| 45 | cyclohexyl-C(=O)-NH- | -CH2-phenyl | -CH2-phenyl | -CH(OC(=O)OC2H5)-CH2-cyclohexyl | one | -CH3 | piperidine ring with -CH(COOH)(H) (L) attached to N |
| 46 | cyclobutyl-C(=O)-NH- | -(CH2)4-NH2 | -C4H9 | -H | zero | -CH3 | piperidine ring with -CH(C(=O)-O-CH(CH(CH3)2)-O-C(=O)-O-C2H5)(H) (L) attached to N |
| 47 | cyclohexyl-C(=O)-NH- | -(CH2)4-NH2 | -C4H9 | -H | one | -CH3 | piperidine ring with -CH(C(=O)-O-CH(cyclohexyl)-O-C(=O)-O-C2H5)(H) (L) attached to N |

EXAMPLE 48

1000 tablets each containing the following ingredients:

| | |
|---|---|
| 1-[(S)-2-[[[1-[[(S)-6-Amino-2-[(cyclobutylcarbonyl)amino]-1-oxohexyl]amino]pentyl]-hydroxyphosphinyl]oxy]-1-oxo-propyl]-L—proline | 100 mg. |
| Cornstarch | 50 mg. |
| Gelatin | 7.5 mg. |
| Avicel (Microcrystalline cellulose) | 25 mg. |
| Magnesium stearate | 2.5 mg. |
| | 185 mg. | are prepared from sufficient bulk quantities by mixing the product of Example 1 and cornstarch with an aqueous solution of the gelatin. The mixture is dried and ground to a powder. The Avicel and then the magnesium stearate are admixed with granulation. This mixture is then compressed in a tablet press to form 1000 tablets each containing 100 mg. of active ingredient. This same procedure can be employed to prepare tablets containing 50 mg. of active ingredient.

Similarly, tablets containing 100 mg. of the product of any of Examples 2 to 47 can be prepared.

EXAMPLE 49

Two piece #1 gelatin capsules are filled with a mixture of the following ingredients:

| | |
|---|---|
| 1-[(S)-6-Amino-2-[[[1-[[(S)-6-amino-2-[(cyclobutylcarbonyl)-amino]-1-oxohexyl]amino]-2-phenylethyl]hydroxyphosphinyl]oxy]-1-oxohexyl]-L—proline | 100 mg. |
| Magnesium stearate | 7 mg. |
| Lactose | 193 mg. |
| | 300 mg. |

In a similar manner, capsules containing 100 mg. of the product of any of Examples 1 and 3 to 47 can be prepared.

EXAMPLE 50

An injectable solution is prepared as follows:

| | |
|---|---|
| 1-[(S)-2-[[[1-[[(S)-6-Amino-2-[(cyclobutylcarbonyl)amino]-1-oxohexyl]amino]-2-phenylethyl]-hydroxyphosphinyl]oxy]-1-oxo-propyl]-L—proline | 500 g. |
| Methyl paraben | 5 g. |
| Propyl paraben | 1 g. |
| Sodium chloride | 25 g. |
| Water for injection | 5 l. |

The active substance, preservatives and sodium chloride are dissolved in 3 liters of water for injection and then the volume is brought up to 5 liters. The solution is filtered through a sterile filter and aseptically filled into presterilized rubber closures. Each vial contains 5 ml. of solution in a concentration of 100 mg. of active ingredient per ml. of solution for injection.

In a similar manner, an injectable solution containing 100 mg. of active ingredient per ml. of solution can be prepared for the product of any of Examples 1, 2, and 4 to 47.

EXAMPLES 51

1000 tablets each containing the following ingredients:

| | |
|---|---|
| 1-[(S)-2-[[[1-[[(S)-6-Amino-2-[(cyclobutylcarbonyl)amino]-1-oxohexyl]amino]pentyl]hydroxyphosphinyl]oxy]-1-oxopropyl]-L—proline | 100 mg. |
| Avicel | 100 mg. |
| Hydrochlorothiazide | 12.5 mg. |
| Lactose | 113 mg. |
| Cornstarch | 17.5 mg. |
| Stearic acid | 7 mg. |
| | 350 mg. | are prepared from sufficient bulk quantities by slugging the product of Example 1, Avicel, and a portion of the stearic acid. The slugs are ground and passed through a #2 screen, then mixed with the hydrochlorothiazide, lactose, cornstarch, and the remainder of the stearic acid. The mixture is compressed into 350 mg. capsule shaped tablets in a tablet press. The tablets are scored for dividing in half.

In a similar manner, tablets can be prepared containing 100 mg. of the products of any of Examples 2 to 47.

What is claimed is:

1. A compound of the formula $$R_{24}-CH(R_4)-\overset{O}{\underset{\|}{C}}-NH-CH(R_2)-\overset{O}{\underset{\|}{P}}(OR_3)-O-CH(R_1)-\overset{O}{\underset{\|}{C}}-N\begin{pmatrix}H_2C-CH_2\\ \diagdown\hspace{-3pt}\diagup\\ C\end{pmatrix}-COOR_6 \quad (L)$$

including a pharmaceutically acceptable salt thereof wherein:

$R_1$ is methyl or $-(CH_2)_4-NH_2$;

$R_2$ is methyl, n-butyl, or benzyl;

$R_3$ is hydrogen, sodium ion, potassium ion, calcium ion, or lithium ion;

$R_4$ is methyl, n-butyl, $-(CH_2)_4-NH_2$, $-(CH_2)_4-NH-\overset{O}{\underset{\|}{C}}-CH_3$, or $-(CH_2)_4-NH-\overset{NH}{\underset{NH_2}{C}}$;

and
$R_{24}$ is $-NH_2$, $-NH-\overset{O}{\underset{\|}{C}}-cyclopropyl$, $-NH-\overset{O}{\underset{\|}{C}}-cyclobutyl$, $NH-\overset{O}{\underset{\|}{C}}-cyclophenyl$, $-NH-\overset{O}{\underset{\|}{C}}-cycloheptyl$, $-NH-\overset{O}{\underset{\|}{C}}-cyclohexyl$, $-NH-\overset{O}{\underset{\|}{C}}-\bigcirc$, $-NH-\overset{O}{\underset{\|}{C}}-N\bigcirc O$, $-NH-\overset{O}{\underset{\|}{C}}-O-C(CH_3)_3$, or -continued

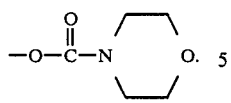

2. The compound of claim 1 wherein:
$R_{24}$ is $NH_2$.
3. The compound of claim 2 wherein:
$R_1$ is —$CH_3$;
$R_2$ is n-butyl;
$R_3$ and $R_6$ are both hydrogen; and
$R_4$ is —$CH_3$.
4. The compound of claim 2 wherein:
$R_1$ is —$CH_3$;
$R_2$ is n-butyl;
$R_3$ and $R_6$ are both hydrogen; and
$R_4$ is —$(CH_2)_4$—$NH_2$.
5. The compound of claim 2 wherein:
$R_1$ is —$CH_3$;
$R_2$ is benzyl;
$R_3$ and $R_6$ are both hydrogen; and
$R_4$ is —$(CH_2)_4$—$NH_2$.
6. The compound of claim 2 wherein:
$R_1$ is —$CH_3$;
$R_2$ is n-butyl;
$R_3$ and $R_6$ are both hydrogen; and
$R_4$ is n-butyl.
7. A compound of claim 1 wherein $R_{24}$ is

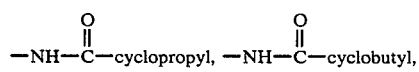

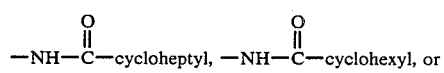

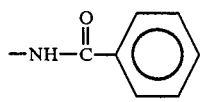

8. The compound of claim 7 wherein
$R_1$ is —$CH_3$;
$R_2$ is n-butyl;
$R_3$ and $R_6$ are both hydrogen;
$R_4$ is —$(CH_2)_4$—$NH_2$; and
$R_{24}$ is

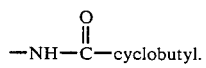

9. The compound of claim 7 wherein:
$R_1$ is —$(CH_2)_4$—$NH_2$;
$R_2$ is benzyl;
$R_3$ and $R_6$ are both hydrogen;
$R_4$ is —$(CH_2)_4$—$NH_2$; and
$R_{24}$ is

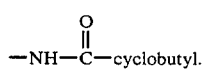

10. The compound of claim 7 wherein:
$R_1$ is —$CH_3$;
$R_2$ is benzyl;
$R_3$ and $R_6$ are both hydrogen;
$R_4$ is —$(CH_2)_4$—$NH_2$; and
$R_{24}$ is

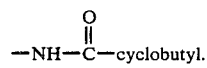

11. The compound of claim 7 wherein:
$R_1$ is —$CH_3$;
$R_2$ is n-butyl;
$R_3$ and $R_6$ are both lithium;
$R_4$ is —$CH_3$; and
$R_{24}$ is

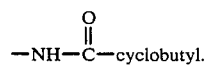

12. The compound of claim 7 wherein:
$R_1$ is —$CH_3$;
$R_2$ is n-butyl;
$R_3$ and $R_6$ are both lithium;
$R_4$ is n-butyl; and $R_{24}$ is

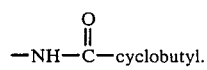

13. The compound of claim 7 wherein:
$R_1$ is —$(CH_2)_4$—$NH_2$;
$R_2$ is n-butyl;
$R_3$ and $R_6$ are both hydrogen;
$R_4$ is —$(CH_2)_4$—$NH_2$; and $R_{24}$ is

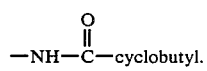

14. The compound of claim 7 wherein:
$R_1$ is —$CH_3$;
$R_2$ is n-butyl;
$R_3$ and $R_6$ are both hydrogen;
$R_4$ is

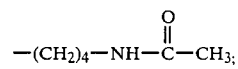

and
$R_{24}$ is

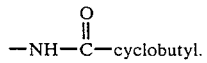

15. The compound of claim 7 wherein:
$R_1$ is —$CH_3$;
$R_2$ is n-butyl;
$R_3$ and $R_6$ are both hydrogen;
$R_4$ is

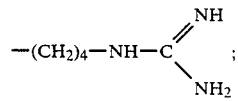

and
$R_{24}$ is

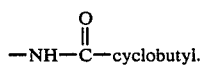

16. The compound of claim 7 wherein;
R₁ is —CH₃;
R₂ is n-butyl;
R₃ and R₆ are both hydrogen;
R₄ is —(CH₂)₄—NH₂; and R₂₄ is

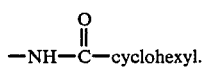

17. The compound of claim 7 wherein:
R₁ is —CH₃;
R₂ is n-butyl;
R₃ and R₆ are both hydrogen;
R₄ is —(CH₂)₄—NH₂; and
R₂₄ is

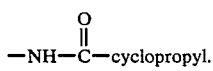

18. The compound of claim 7 wherein:
R₁ is —CH₃ ;
R₂ is n-butyl;
R₃ and R₆ are both hydrogen;
R₄ is —(CH₂)₄—NH₂; and
R₂₄ is

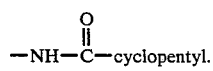

19. The compound of claim 7 wherein:
R₁ is —CH₃;
R₂ is n-butyl;
R₃ and R₆ are both hydrogen;
R₄ is —(CH₂)₄—NH₂; and
R₂₄ is

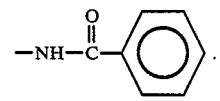

20. A compound of claim 1 wherein R₂₄ is

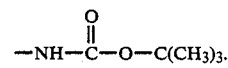

21. The compound of claim 20 wherein:
R₁ is —CH₃;
R₂ is n-butyl;
R₃ and R₆ are both lithium; and
R₄ is n-butyl.

22. A compound of claim 1 wherein:
R₂₄ is

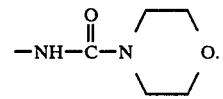

23. The compound of claim 22 wherein:
R₁ is —CH₃;
R₂ is n-butyl;
R₃ and R₆ are both hydrogen; and
R₄ is —(CH₂)₄—NH₂.

24. A compound of claim 1 wherein R₂₄ is

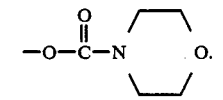

25. The compound of claim 24 wherein:
R₁ is —CH₃;
R₂ is n-butyl;
R₃ and R₆ are both hydrogen; and
R₄ is —(CH₂)₄—NH₂.

26. A pharmaceutical composition useful for treating hypertension in a mammalian species comprising a pharmaceutically acceptable carrier and an anti-hypertensive effective amount of a compound of claim 1.

27. The method of treating hypertension in a mammalian host which comprises administering an effective amount of the composition of claim 6.

* * * * *

UNITED STATES PATENT AND TRADEMARK OFFICE
CERTIFICATE OF CORRECTION

PATENT NO. : 4,849,414
DATED : July 18, 1989
INVENTOR(S) : Melanie J. Loots et al.

It is certified that error appears in the above-identified patent and that said Letters Patent is hereby corrected as shown below:

Claim 1, Col. 74, line 58 " $NH-\overset{\overset{O}{\|}}{C}-cyclophenyl,$ "

should read -- $-NH-\overset{\overset{O}{\|}}{C}-cyclopentyl,$ --- .

Claim 1, Col. 75, line 5 after the formula should be inserted
--- $R_6$ is hydrogen, lower alkyl, benzyl, benzhydryl, alkaline metal salt ion or alkaline earth metal salt ion. --

Signed and Sealed this

Fifth Day of February, 1991

*Attest:*

HARRY F. MANBECK, JR.

*Attesting Officer*   *Commissioner of Patents and Trademarks*